(12) United States Patent
Abdolahad et al.

(10) Patent No.: US 11,806,140 B2
(45) Date of Patent: *Nov. 7, 2023

(54) MEASURING AN ELECTROCHEMICAL RESPONSE FROM A THREE-ELECTRODE ARRAY

(71) Applicants: Mohammad Abdolahad, Tehran (IR); Naser Namdar Habashi, Tabriz (IR); Zohreh Sadat Miripour, Tehran (IR)

(72) Inventors: Mohammad Abdolahad, Tehran (IR); Naser Namdar Habashi, Tabriz (IR); Zohreh Sadat Miripour, Tehran (IR)

(73) Assignee: Mohammad Abdolahad, Tehran (IR)

(*) Notice: Subject to any disclaimer, the term of this patent is extended or adjusted under 35 U.S.C. 154(b) by 114 days.

This patent is subject to a terminal disclaimer.

(21) Appl. No.: 17/207,615

(22) Filed: Mar. 20, 2021

(65) Prior Publication Data

US 2021/0204839 A1 Jul. 8, 2021

Related U.S. Application Data

(63) Continuation of application No. 17/034,067, filed on Sep. 28, 2020, now Pat. No. 11,179,077, which is a (Continued)

(51) Int. Cl.
*G01N 27/327* (2006.01)
*A61B 5/1473* (2006.01)
(Continued)

(52) U.S. Cl.
CPC .......... *A61B 5/1473* (2013.01); *A61B 5/6848* (2013.01); *G01N 27/308* (2013.01); *G01N 27/3273* (2013.01); *G01N 27/3278* (2013.01)

(58) Field of Classification Search
CPC ............ G01N 27/308; G01N 27/3278; G01N 27/3273

See application file for complete search history.

(56) References Cited

U.S. PATENT DOCUMENTS 7,939,734 B1 5/2011 Li
9,689,046 B2 6/2017 Mayall
(Continued)

OTHER PUBLICATIONS

Wikipedia contributors. "Cyclic voltammetry." Wikipedia, The Free Encyclopedia, https://web.archive.org/web/20071022182012/https://en.wikipedia.org/wiki/Cyclic_voltammetry, Oct. 22, 2007. Accessed Nov. 25, 2020 (Year: 2007).

(Continued)

*Primary Examiner* — Andrey Shostak
(74) *Attorney, Agent, or Firm* — Bajwa IP Law Firm; Haris Zaheer Bajwa

(57) ABSTRACT

An apparatus for in-vivo measuring $H_2O_2$ oxidation within a living tissue. The apparatus includes an electrochemical probe and an electrochemical stimulator-analyzer. The electrochemical probe includes a sensing part and a handle. The sensing part includes a working electrode, a counter electrode, and a reference electrode. The working electrode includes a first biocompatible conductive needle coated with a layer of vertically aligned multi-walled carbon nanotubes. The counter electrode includes a second biocompatible conductive needle. The reference electrode includes a third biocompatible conductive needle. The electrochemical stimulator-analyzer is configured to generate a set of electrical currents in a portion of the living tissue.

13 Claims, 79 Drawing Sheets

Related U.S. Application Data continuation-in-part of application No. 16/857,428, filed on Apr. 24, 2020, now Pat. No. 10,786,188, which is a continuation-in-part of application No. 16/010,510, filed on Jun. 17, 2018, now Pat. No. 11,181,499.

(60) Provisional application No. 62/563,673, filed on Sep. 27, 2017, provisional application No. 62/522,115, filed on Jun. 20, 2017.

(51) Int. Cl.
*A61B 5/00* (2006.01)
*G01N 27/30* (2006.01)

(56) References Cited

U.S. PATENT DOCUMENTS

| | | | |
|---|---|---|---|
| 2005/0158787 A1* | 7/2005 | Hongo | G01N 33/5438 435/287.2 |
| 2009/0061451 A1 | 3/2009 | Achim | |
| 2009/0076496 A1 | 3/2009 | Azure | |
| 2010/0066378 A1* | 3/2010 | Ahmadi | G01N 27/3273 324/429 |
| 2013/0102027 A1 | 4/2013 | Mohajerzadeh et al. | |
| 2014/0072308 A1* | 3/2014 | Jain | A61B 5/14503 398/43 |
| 2015/0005788 A1 | 1/2015 | Sniffin | |
| 2015/0268207 A1 | 9/2015 | Motayed | |
| 2016/0095585 A1 | 4/2016 | Zergiebel | |
| 2016/0258899 A1 | 9/2016 | Patolsky et al. | |
| 2018/0059054 A1* | 3/2018 | Nishida | G01N 27/416 |
| 2019/0227028 A1 | 7/2019 | Patolsky et al. | |

OTHER PUBLICATIONS

Wikipedia contributors. "American wire gauge." Wikipedia, The Free Encyclopedia, https://web.archive.org/web/20071103232133/ http://en.Wikipedia.org:80/wiki/American_wire_gauge#Table_of_ AWGs_and_approximate_corresponding_sizes, Nov. 3, 2007. Accessed Oct. 29, 2020 (Year: 2007).

* cited by examiner

MEASURING AN ELECTROCHEMICAL RESPONSE FROM A THREE-ELECTRODE ARRAY

CROSS-REFERENCE TO RELATED APPLICATION

This application is a continuation of patent application Ser. No. 17/034,067, filed Sep. 28, 2020, and entitled "REAL-TIME AND LABEL FREE ANALYZER FOR IN-VITRO AND IN-VIVO DETECTING THE SUSPICIOUS REGIONS TO CANCER", which is a continuation-in-part of U.S. patent application Ser. No. 16/857,428, filed Apr. 24, 2020, and entitled "REAL-TIME AND LABEL FREE ANALYZER FOR IN-VITRO AND IN-VIVO DETECTING THE SUSPICIOUS REGIONS TO CANCER," which is a continuation-in-part of U.S. patent application Ser. No. 16/010,510, filed Jun. 17, 2018, and entitled "REAL-TIME AND LABEL FREE ANALYZER FOR IN-VITRO AND IN-VIVO DETECTING THE SUSPICIOUS REGIONS TO CANCER", which takes priority from U.S. Provisional Patent Application Ser. No. 62/522,115 filed on Jun. 20, 2017, and entitled "DIAGNOSIS OF CANCER TUMORS IN BIOPSY BREAST TISSUES" and U.S. Provisional Patent Application Ser. No. 62/563,673 filed on Sep. 27, 2017, and entitled "CANCER DIAGNOSTIC PROBE", which are all incorporated herein by reference in their entirety.

TECHNICAL FIELD

The present disclosure generally relates to cancer diagnosis, and particularly, to a system, sensor, and method for diagnosing cancerous regions before and during surgery via a real-time and label free approach.

BACKGROUND

Glycolysis is the intracellular biochemical conversion of one molecule of glucose into two molecules of pyruvate, which can be used to attain cellular energy. With the assistance of sufficient oxygen, pyruvate could be converted by pyruvate dehydrogenase (PDH) into acetylCoA which is crucial in a metabolizing process to produce ATP in an oxidative way. A physiological concentration of pyruvate in human normal epithelial tissue has been reported to 0.7 mmol/g. Also the lactate-to-pyruvate ratio (L/P ratio) as a reflection of cell's redox state, illustrates the balance between NAD+ and NADH+H+, depending on the interconversion of lactate and pyruvate via lactate dehydrogenase (LDH). The UP ratio in normal epithelial tissues is less than 20:1. Markers and assays have been developed to trace the LADH, P, or UP in the patients' specimen as diagnostic or prognostic factors which reveal the interests on lactate based cancer research. Moreover some methods have been developed to trace pyruvate by electrochemical methods with the assistance of chemically labelled working electrodes. However, there is still no substitutive label free methods and/or devices to replace expensive, complicated, and late-responsive clinical methods and devices such as pathology assays.

Hence, there is a need for cost-effective, label free and real-time methods and devices, especially sensors and method to use thereof to detect cancer in suspicious regions especially during cancer surgery like mastectomy to remove involved regions with precise margins to reduce resection of normal sites.

SUMMARY

This summary is intended to provide an overview of the subject matter of the present disclosure, and is not intended to identify essential elements or key elements of the subject matter, nor is it intended to be used to determine the scope of the claimed implementations. The proper scope of the present disclosure may be ascertained from the claims set forth below in view of the detailed description below and the drawings.

In one general aspect, the present disclosure describes an exemplary apparatus for in-vivo measuring $H_2O_2$ oxidation within a living tissue. An exemplary apparatus may include an electrochemical probe and an electrochemical stimulator-analyzer. An exemplary electrochemical probe may include a sensing part and a handle. An exemplary sensing part may include a working electrode, a counter electrode, and a reference electrode. An exemplary working electrode may include a first biocompatible conductive needle coated with a layer of vertically aligned multi-walled carbon nanotubes (VAMWCNTs). An exemplary counter electrode may include a second biocompatible conductive needle. An exemplary reference electrode may include a third biocompatible conductive needle.

An exemplary handle may include an insertion part and a releasing button. In an exemplary embodiment, the insertion pan may be attached to the sensing part. In an exemplary embodiment, the insertion part may be configured to be inserted into a portion of the living tissue. In an exemplary embodiment, the releasing button may be configured to release the sensing part for replacing the sensing part.

In an exemplary embodiment, the electrochemical stimulator-analyzer may be configured to generate a set of electrical currents in the portion of the living tissue by applying a set of electrical potentials to the electrochemical probe and record the set of electrical currents by measuring an electric current flowing from the counter electrode to the working electrode.

In an exemplary embodiment, the electrochemical stimulator-analyzer may be further configured to apply the set of electrical potentials by applying a sweeping range of electrical potentials between $-1$ V and 1 V to the working electrode and measure the electric currents at the working electrode after applying each electrical potential in the sweeping range.

An exemplary electrochemical stimulator-analyzer may include a potentiostat circuit. An exemplary potentiostat circuit may include a control amplifier, a transimpedance amplifier, a peak detector circuit, a feedback network, a periodic wave generator, and a comparator circuit. An exemplary control amplifier may include a first control input, a second control input coupled to the reference electrode, and a control output coupled to the counter electrode. In an exemplary embodiment, the control amplifier may be configured to generate a control voltage at the control output by amplifying a voltage difference between the first control input and the second control input. An exemplary control amplifier may include an operational amplifier (op-amp).

An exemplary transimpedance amplifier may include a transimpedance output and a transimpedance input connected to the working electrode. In an exemplary embodiment, the transimpedance amplifier may be configured to generate a transimpedance voltage at the transimpedance output by amplifying a voltage of the transimpedance input. An exemplary peak detector circuit may include a detector output and a detector input coupled to the transimpedance output. In an exemplary embodiment, the peak detector circuit may be configured to detect a maximum voltage at the detector input in a given period of time and transmit the maximum voltage to the detector output. An exemplary transimpedance amplifier may include an op-amp.

In an exemplary embodiment, the periodic wave generator may be configured to generate a periodic ware at the first control input responsive to becoming active. In an exemplary embodiment, the periodic wave generator may be further configured to couple the first control input to ground responsive to becoming inactive. An exemplary periodic wave generator may include a pulse wave generator, an op-amp that may be coupled to the pulse wave generator, an RC circuit that may be connected between the op-amp output and the negative input, and a field effect transistor (FET). An exemplary pulse wave generator may be configured to generate a periodic rectangular wave. An exemplary op-amp may include a positive input, a negative input, and an op-amp output. In an exemplary embodiment, the positive input may be connected to ground, the negative input may be coupled to an output of the pulse wave generator, and the op-amp output may be connected to the first control input. An exemplary RC circuit may include a first resistor and a first capacitor that may be connected in parallel.

An exemplary periodic wave generator may further include a second resistor and a third resistor. In an exemplary embodiment, the second resistor may be connected to the negative input and the third resistor may be connected between the second resistor and the output of the pulse wave generator. An exemplary FET may include a source, a drain, and a gate. An exemplary source may be connected to ground. In an exemplary embodiment, the drain may be connected between the second resistor and the third resistor, and the gate may be connected to the activation input.

In an exemplary embodiment, the comparator circuit may be configured to activate the periodic wave generator by providing an activation voltage to an activation input of the periodic wave generator responsive to a voltage of the detector output being smaller than a reference voltage. In an exemplary embodiment, the comparator circuit may be further configured to deactivate the periodic wave generator by providing a deactivation voltage to the activation input responsive to a voltage of the detector output being equal to or larger than the reference voltage.

An exemplary comparator circuit may include a first comparator input, a second comparator input, and a comparator output. An exemplary first comparator input may be connected to the detector output and an exemplary comparator output may be connected to the activation input. In an exemplary embodiment, the second comparator input may include the reference voltage. An exemplary second comparator input may be coupled to a DC voltage supply that may include a DC voltage. In an exemplary embodiment, the second comparator input may be coupled to the DC voltage supply via a variable resistor. An exemplary variable resistor may be configured to provide the reference voltage to the second comparator input by transmitting a fraction of the DC voltage to the second comparator input.

In an exemplary embodiment, the comparator circuit may be configured to provide the activation voltage to the comparator output responsive to a voltage of the first comparator input being smaller than a voltage of the second comparator input and provide the deactivation voltage to the comparator output responsive to the voltage of the first comparator input being equal to or larger than the voltage of the second comparator input.

In an exemplary embodiment, the feedback network may be connected between the detector input and the transimpedance input. An exemplary feedback network may include a feedback resistor. In an exemplary embodiment, a resistance $R_f$ of the feedback resistor may be equal to $$\frac{V_{ref}}{I_{max}},$$

where $V_{ref}$ is the reference voltage and $I_{max}$ is an upper limit of an electric current flowing through the detector input.

In an exemplary embodiment, the potentiostat circuit may further include a unity gain amplifier that may be connected between the reference electrode and the second control input. An exemplary unity gain amplifier may include a first unity gain input, a unity gain output, and a second unity gain input. In an exemplary embodiment, the first unity gain input may be connected to the reference electrode, the unity gain output may be connected to the second control input, and the second unity gain input may be connected to the unity gain output. In an exemplary embodiment, the unity gain amplifier may be configured to transmit a voltage at the reference electrode to the unity gain output by amplifying a voltage difference between the first unity gain input and the second unity gain input. An exemplary unity gain amplifier may include an op-amp.

In an exemplary embodiment, the potentiostat circuit may further include a first current buffer amplifier (CBA) that may be connected between the control amplifier and the counter electrode. An exemplary first CBA may be configured to transfer an electric current flowing through the control output to the counter electrode. In an exemplary embodiment, the potentiostat circuit may further include a second CBA that may be connected between the transimpedance amplifier and the peak detector circuit. An exemplary second CBA may be configured to transfer an electric current flowing through the transimpedance output to the detector input.

In an exemplary embodiment, the potentiostat circuit may further include a first analog compensator that may be connected between the counter electrode and the first control input. An exemplary first analog compensator may be configured to compensate voltage variations at the counter electrode responsive to voltage variations at the first control input. An exemplary first analog compensator may include a first compensation capacitor. In an exemplary embodiment, the potentiostat circuit may further include a second analog compensator that may be connected between the second control input and ground. An exemplary second analog compensator may be configured to compensate voltage variations at the second control input. An exemplary second analog compensator may include a second compensation capacitor and a compensation resistor that may be connected in series.

In an exemplary embodiment, each of the first biocompatible conductive needle, the second biocompatible conductive needle, and the third biocompatible conductive needle may include a respective sensing tip coated with a layer of VAMWCNTs. In an exemplary embodiment, each of the working electrode, the counter electrode, and the reference electrode may include a respective sensing tip with a diameter between 100 µm and 200 µm, and a length between 0.1 cm and 1 cm. In an exemplary embodiment, the working electrode, the counter electrode, and the reference electrode may be attached to the insertion part at one end of the handle apart from each other with a distance between 1 mm and 5 mm.

In an exemplary embodiment, the sensing part may further include an electrode holder encompassing the working electrode, the counter electrode, and the reference electrode. In an exemplary embodiment, the handle may further include a handle head and a switch located on the handle head. In an exemplary implementation, the switch may be configured to connect the electrochemical probe to an electrochemical stimulator-analyzer device, and disconnect the electrochemical probe from the electrochemical stimulator-analyzer device.

Other exemplary systems, methods, features and advantages of the implementations will be, or will become, apparent to one of ordinary skill in the art upon examination of the following figures and detailed description. It is intended that all such additional systems, methods, features and advantages be included within this description and this summary, be within the scope of the implementations, and be protected by the claims herein.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

Figure 1A:
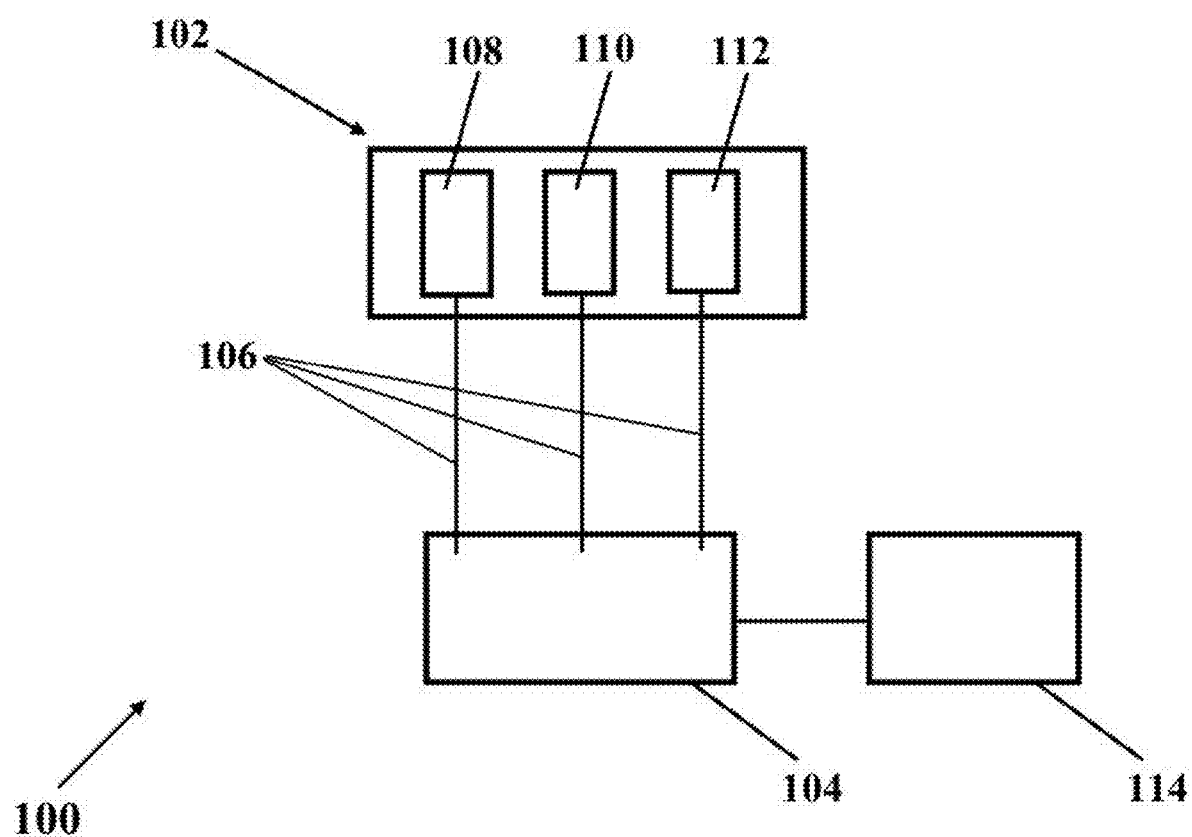
FIG. 1A illustrates a schematic view of an exemplary electrochemical system for cancer diagnosis, consistent with one or more exemplary embodiments of the present disclosure.

In the following detailed description, numerous specific details are set forth by way of examples in order to provide a thorough understanding of the relevant teachings. However, it should be apparent that the present teachings may be practiced without such details. In other instances, well known methods, procedures, components, and/or circuitry have been described at a relatively high-level, without detail, in order to avoid unnecessarily obscuring aspects of the present teachings. The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown, but is to be accorded the widest possible scope consistent with the principles and features disclosed herein.

A number of current methods utilize lactate and/or pyruvate as cancer markers. However, herein the oxidation of Hydrogen Peroxide ($H_2O_2$) molecules measured by carbon nanotubes (CNTs) based electrodes is utilized to detect cancer and especially distinguish cancerous regions from healthy regions in a suspicious tissue. The main consequence of pyruvate formation from lactate is release of $H_2O_2$ molecules as the main byproduct of hypoxia glycolysis. An abnormal redox state appears in cancer cells based on modulation of hypoxia with increased pyruvate concentration and lactate-to-pyruvate ratio (L/P ratio) which results in increasing the concentration of $H_2O_2$ in interstitial fluid (stroma). So, determination of $H_2O_2$ molecules would be an indication for the presence of cancer cells in a tissue. As $H_2O_2$ is an active and non-stable molecule it would turn to $O_2$, $H^+$ and release electrons which are great target charges for electrochemical sensation.

Herein, an electrochemical approach based on multi-walled carbon nanotubes (MWCNTs) electrodes is disclosed for fast tracking of hypoxia glycolysis in the interstitial fluid of biopsied tissues suspicious to cancer, such as breast tissues. Electrochemical reduction of $H_2O_2$ molecules, produced in lactate to pyruvate transformation, on the electrodes of disclosed system may present a significant quantitate response signal in correlation with the presence of cancer cells in a suspicious sample. Here, a cancer diagnostic probe (CDP) based on vertically aligned multi-walled carbon nanotubes (VAMWCNTs) arrays as sensing electrode with direct and selective electron transfer abilities in interaction with $H_2O_2$ may be utilized.

Disclosed herein may include a label free method for diagnosis of the presence of cancer in suspicious regions based on determination of the hypoxia glycolysis in a quantitative manner. The method may be based on measuring the oxidative currents released during glycolysis from the tissue. A matched diagram between an electrochemical response measured from a suspicious sample and cancerous state curves may be utilized for a final diagnostic result. Over expression of glycolysis assisted mRNAs in cancerous samples may be observed as an indicator of a presence of cancer in a sample. Exemplary method may be applied as an alternative for frozen pathology during the surgery with faster and more precise efficiency. Furthermore, a label free system including an electrochemical sensor with integrated three CNT based electrodes is disclosed for tracking hypoxia glycolysis via detecting electrochemical reduction of $H_2O_2$ molecules, which may be produced in Lactate to pyruvate transformation in cancer cells. Exemplary simple and label free electrochemical assay may also be used for measuring the drug resistance of the tumors as a pre therapeutic prediction (as a new prognostic factor) to increase the survival rate in future.

In some implementations, exemplary electrochemical sensor may include an integrated sensor on the needles, named herein as a cancer diagnostic probe (CDP). Exemplary CDP may be fabricated and utilized in real-time on the suspicious regions to cancer before and during surgery in patients (In vivo). The domain of suspicious regions with a resolution of about 3 mm may be detected using exemplary method and CDP. The significant specification of CDP rather than recently reported real-time diagnostic methods, such as mass-spec, may allow the CDP to track the cancer involved regions before surgery by squeezing exemplary CDP to suspicious regions through the skin with the tracking resolution of 3 mm. In conventional diagnostic protocols, to precisely remove the cancer regions during surgery, a frozen sample from each suspicious region may need to be sent for pathologists. The pathology results may be available after about 15 minutes with the false negative response ratio of about 10%. Whereas, a cancer region may be distinguished in-situ utilizing exemplary CDP in less than about 10 seconds or even instantaneously before or during surgery and without any need for resecting and freezing a sample from a patient. The diagnostic information obtained by exemplary CDP may be used to detect cancer in marginally suspicious regions with rare distributions of cancer cells filtrated between normal stroma in less than about 20 seconds during the surgery or biopsy of live animal or human models without any requirement of tissue resection and preparation for frozen pathology. Exemplary CDP may be also utilized to detect an accurate location of cancer involved regions before surgery in superficial tumors.

Moreover, exemplary sensor may include a CNT based electrochemical chip for in vitro cancer diagnosis in suspicious samples. Exemplary CNT based electrochemical chip may include an array of electrodes of VAMWCNTs used in electrochemical assays. Both liquid and solid suspicious samples may be analyzed using exemplary CNT based electrochemical chip to detect a cancer presence within the suspicious samples.

FIG. 1A shows a schematic view of an electrochemical system 100 for cancer diagnosis, consistent with one or more exemplary embodiments of the present disclosure. Exemplary electrochemical system 100 may include an exemplary sensor 102, an electrochemical stimulator-analyzer 104, and an array of electrically conductive connectors 106. Exemplary sensor 102 may be configured to put in contact with a suspicious sample for cancer. Exemplary sensor 102 may include an integrated three-electrodes array, which may include the working electrode 108, the counter electrode 110, and the reference electrode 112. Each of the working electrode 108, the counter electrode 110 and the reference electrode 112 may include an array of vertically aligned multi-walled carbon nanotubes (VAMWCNTs). The electrochemical stimulator-analyzer 104 may be configured to measure electrochemical responses from the working electrode 108 and sensor 102 may be connected to the electrochemical stimulator-analyzer 104 via the army of electrically conductive connectors 106.

In an exemplary implementation, exemplary electrochemical system 100 may be configured to detect a cancerous state via measuring $H_2O_2$ during hypoxia glycolysis in the suspicious sample for cancer. Exemplary electrochemical system 100 may be utilized by an exemplary method for cancer diagnosis described herein below.

In an exemplary embodiment, electrochemical stimulator-analyzer 104 may include a device that may be capable of measuring cyclic voltammetry (CV) based diagrams. In an exemplary embodiment, electrochemical stimulator-analyzer 104 may include a potentiostat.

In an exemplary implementation, electrochemical system 100 may further include a processor 114 that may be utilized for recording and analyzing electrochemical measurements that may be measured by electrochemical stimulator-analyzer 104. Processor 114 may also be used for controlling electrochemical stimulations that may be carried out by electrochemical stimulator-analyzer 1064. In an exemplary embodiment, processor 114 may include an EVIUM readout system.

Figure 1B:
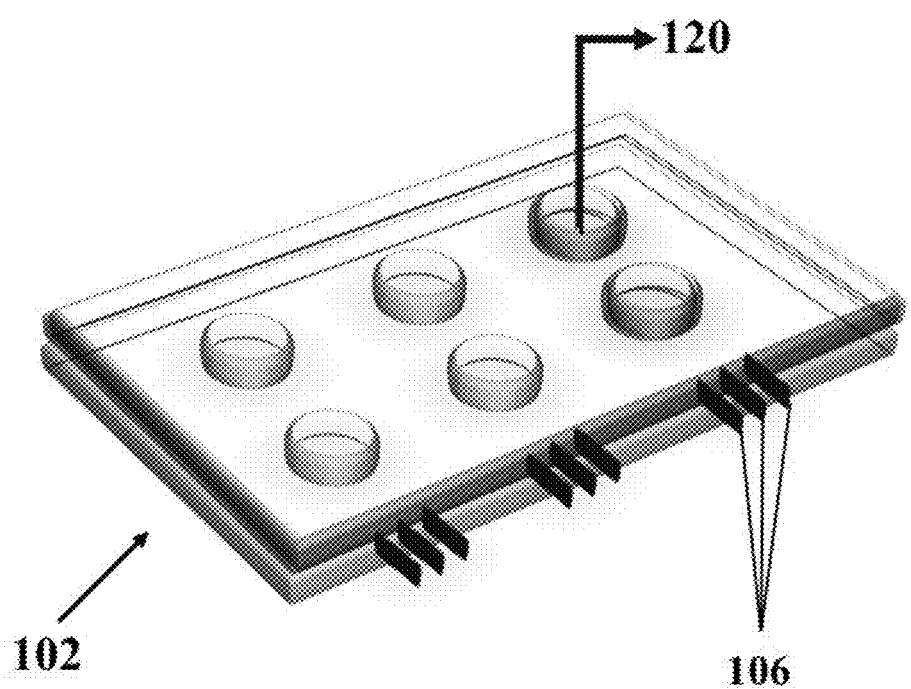
FIG. 1B illustrates a schematic view of an exemplary CNT based electrochemical chip, consistent with one or more exemplary embodiments of the present disclosure.
Figure 1C:
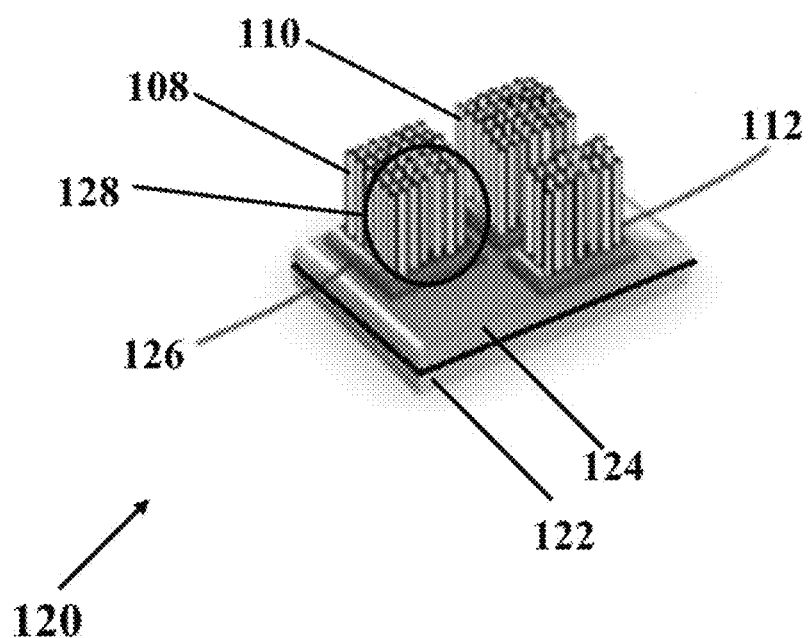
FIG. 1C illustrates a schematic view of an exemplary sensing well, consistent with one or more exemplary embodiments of the present disclosure.

In an exemplary implementation, sensor 102 may include a CNT based electrochemical chip that may be configured to conduct in vitro cancer diagnosis assays. FIG. 1B shows a schematic view of exemplary CNT based electrochemical chip 102, consistent with one or more exemplary embodiments of the present disclosure. Exemplary CNT based electrochemical chip 102 may include at least one sensing well 120 and one army of electrically conductive connectors 106. FIG. 1C shows a schematic view of exemplary sensing well 120, consistent with one or more exemplary embodiments of the present disclosure. Each sensing well 120 may include a substrate 122, a passivation layer 124 that may be grown on substrate 122, a catalyst layer 126 that may be coated or deposited and subsequently patterned on the passivation layer 124, and three arrays of VAMWCNTs that may be grown on the catalyst layer 126. Three arrays of VAMWCNTs may include the working electrode 108, the counter electrode 110, and the reference electrode 112.

In an exemplary embodiment, substrate 122 may include a silicon chip or wafer. Passivation layer 124 may include a layer of $SiO_2$ with a thickness of less than about 500 nm that may be grown by wet oxidation furnace on the surface of on substrate 122. Catalyst layer 126 may include a layer of Nickel (Ni) with a thickness of less than about 10 nm that may be coated on passivation layer 124 by an E-beam evaporation system at a temperature of about 120° C. with depositing rate of about 0.1 Angstroms/s. Three arrays of VAMWCNTs (the working electrode IN, the counter electrode 110, and the reference electrode 112) may be grown on catalyst layer 126 using a direct current plasma enhanced chemical vapor deposition (DC-PECVD) system. The growth process of VAMWCNTs may include three steps of firstly, annealing at a temperature of about 680° C. in an $H_2$ environment with a flow rate of about 35 standard cubic centimeters per minute (scm) for about 30 minutes; secondly, graining, including plasma hydrogenation of surface for about 5 minutes with the intensity of about 5.5 $W \cdot cm^{-2}$ that may result in the catalyst layer 126 graining and formation of Ni nano-sized islands, and finally, growth of VAMWCNTs by introducing a plasma of $C_2H_2$ and $H_2$ mixture with flow rates of about 5 sccm and about 35 sccm to the chamber for about 15 minutes. Each of the VAMWCNTs may have a length between about 0.5 μm and about 5 μm and a diameter between about 20 nm and about 100 nm. The working electrode 108 may be grown on an area of about 1 cm×1 cm, the counter electrode 110 may be grown on an area of about 1 cm×1 cm, and the reference electrode 112 may be grown on an area of about 0.5 cm×0.5 cm.

Figure 1D:
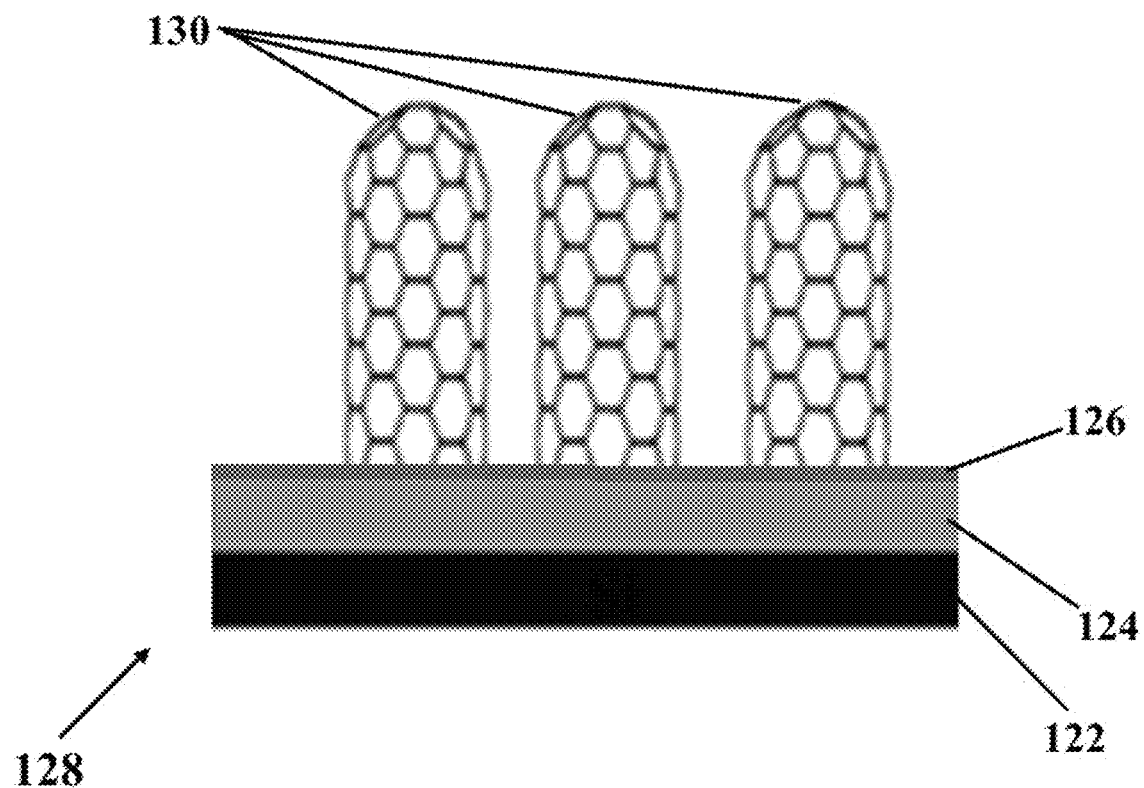
FIG. 1D illustrates a schematic view of an exemplary magnified portion of exemplary working electrode within exemplary sensing well of FIG. 1C, consistent with one or more exemplary embodiments of the present disclosure.

FIG. 1D shows a schematic view of an exemplary magnified portion 128 of exemplary working electrode 103 within exemplary sensing well 120 of FIG. 1C, consistent with one or more exemplary embodiments of the present disclosure. Exemplary VAMWCNTs 130 of an array of VAMWCNTs of working electrode IN may be grown vertically on catalyst layer 126. Catalyst layer 126 may be coated or deposited and subsequently patterned on the passivation layer 124, where passivation layer 124 may be grown on substrate 122.

Figure 1E:
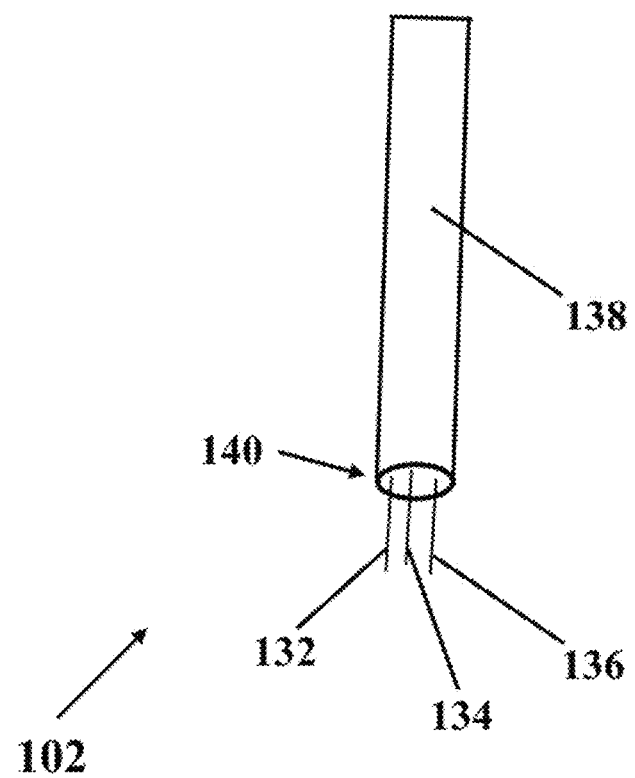
FIG. 1E illustrates a schematic view of an exemplary cancer diagnosis probe (CDP), consistent with one or more exemplary embodiments of the present disclosure.

In an exemplary implementation, sensor 102 may include a cancer diagnosis probe (CDP) that may be configured to conduct in vivo cancer diagnosis assays. FIG. 1E shows a schematic view of exemplary cancer diagnosis probe (CDP) 102, consistent with one or more exemplary embodiments of the present disclosure. Exemplary cancer diagnosis probe (CDP) may include three needle electrodes 132, 134, and 136 as exemplary implementations of the working electrode 108, the counter electrode 110, and the reference electrode 112, respectively. Moreover, CDP 102 may include a holding member 138 that may be configured to hold three needle electrodes 132, 134, and 136. Three needle electrodes 132, 134, and 136 may be fixed on one end 146 of the holding member 138.

Figure 1F:
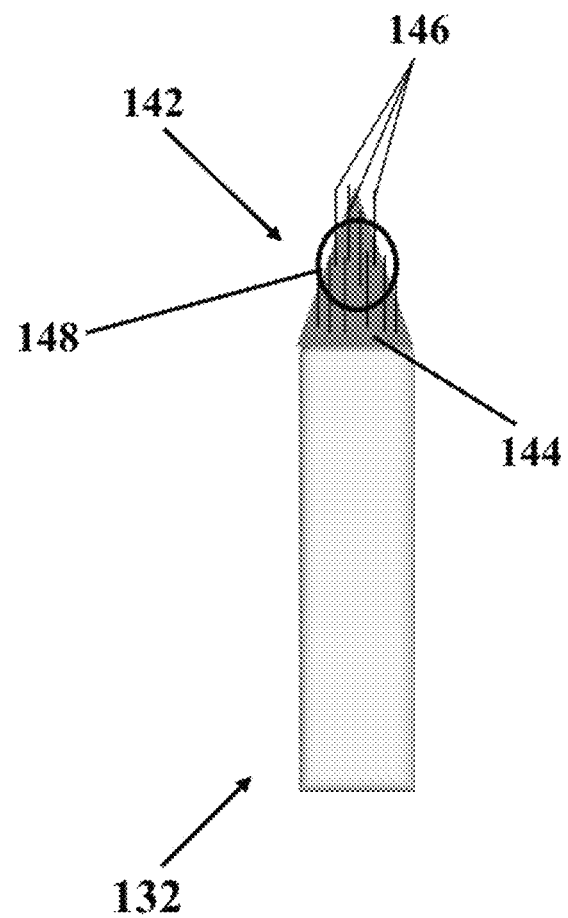
FIG. 1F illustrates a schematic view of an exemplary needle electrode of exemplary CDP corresponding to the working electrode, consistent with one or more exemplary embodiments of the present disclosure.

FIG. 1F shows a schematic view of an exemplary needle electrode 132 corresponding to the working electrode 108, consistent with one or more exemplary embodiments of the present disclosure. Referring to FIG. 1F, each needle electrode of three needles electrodes 132, 134, and 138 may include a tip 142. Each needle electrode of the three needles electrodes 132, 134, and 136 may include a catalyst layer 144 that may be deposited on tips 142 of three needles electrodes 132, 134, and 136 and an array of VAMWCNTs 146 that may be grown on catalyst layer 144 on tip 142 of each needle electrode of three needles electrodes 132, 134, and 138.

In an exemplary embodiment, each needle electrode of three needles electrodes 132, 134, and 138 may include a steel needle with a diameter between about 100 μm and about 200 μm, and a length between about 0.1 cm and about 1 cm. Three needle electrodes 132, 134, and 138 may be fixed on the end 140 of the holding member 138 apart from each other with a distance (interspace) between each other in a range of about 1 mm to about 5 mm.

In an exemplary embodiment, catalyst layer 144 may include a layer of Nickel (Ni) with a thickness of less than about 10 nm that may be coated on tip 142 of each needle electrode by an E-beam evaporation system at a temperature of about 120° C. with a depositing rate of about 0.1 Angstroms/s. Three arrays of VAMWCNTs (the working electrode 108, the counter electrode 110, and the reference electrode 112) may be grown on catalyst layer 144 using a direct current plasma enhanced chemical vapor deposition (DC-PECVD) system as described herein above.

Figure 1G:
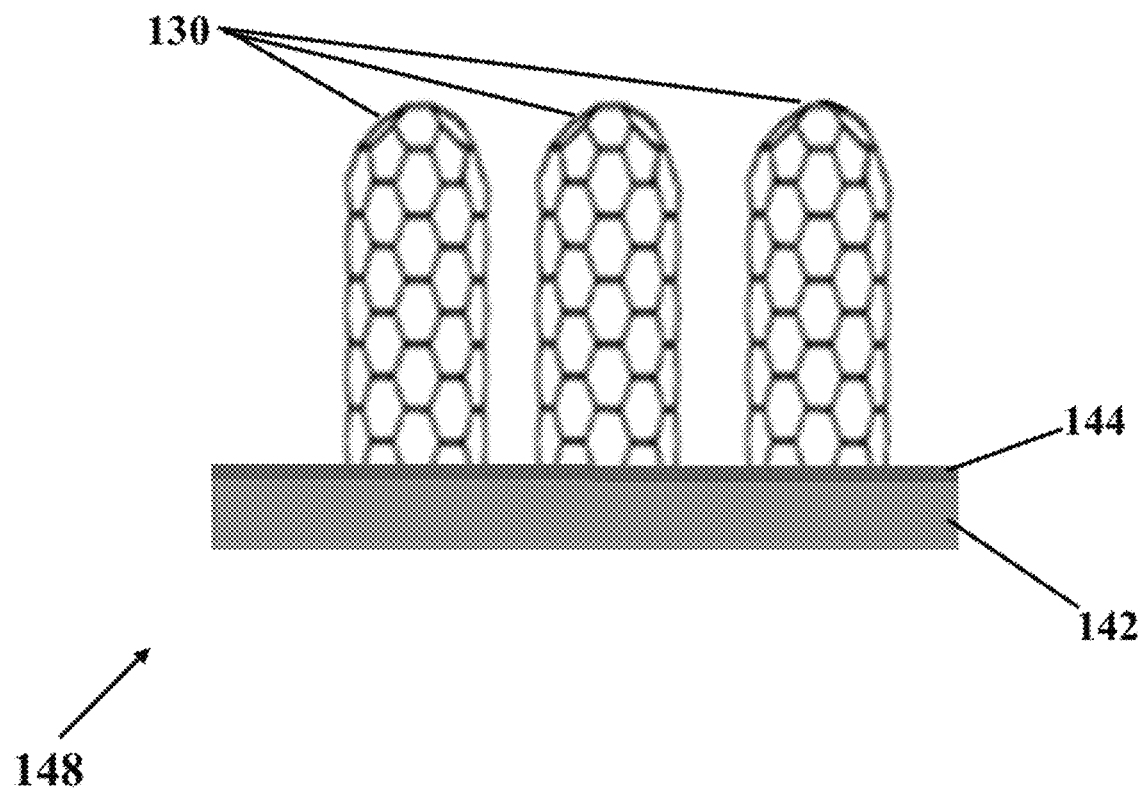
FIG. 1G illustrates a schematic view of an exemplary magnified portion of a tip of exemplary needle electrode of FIG. 1C, consistent with one or more exemplary embodiments of the present disclosure.

FIG. 1G shows a schematic view of an exemplary magnified portion 148 of tip 142 of exemplary needle electrode 132 shown in FIG. 1F, consistent with one or more exemplary embodiments of the present disclosure. Exemplary VAMWCNTs 130 of an array of VAMWCNTs 146 may be grown vertically on catalyst layer 144. Catalyst layer 144 may be coated or deposited on a surface of tip 142.

Figure 1H:
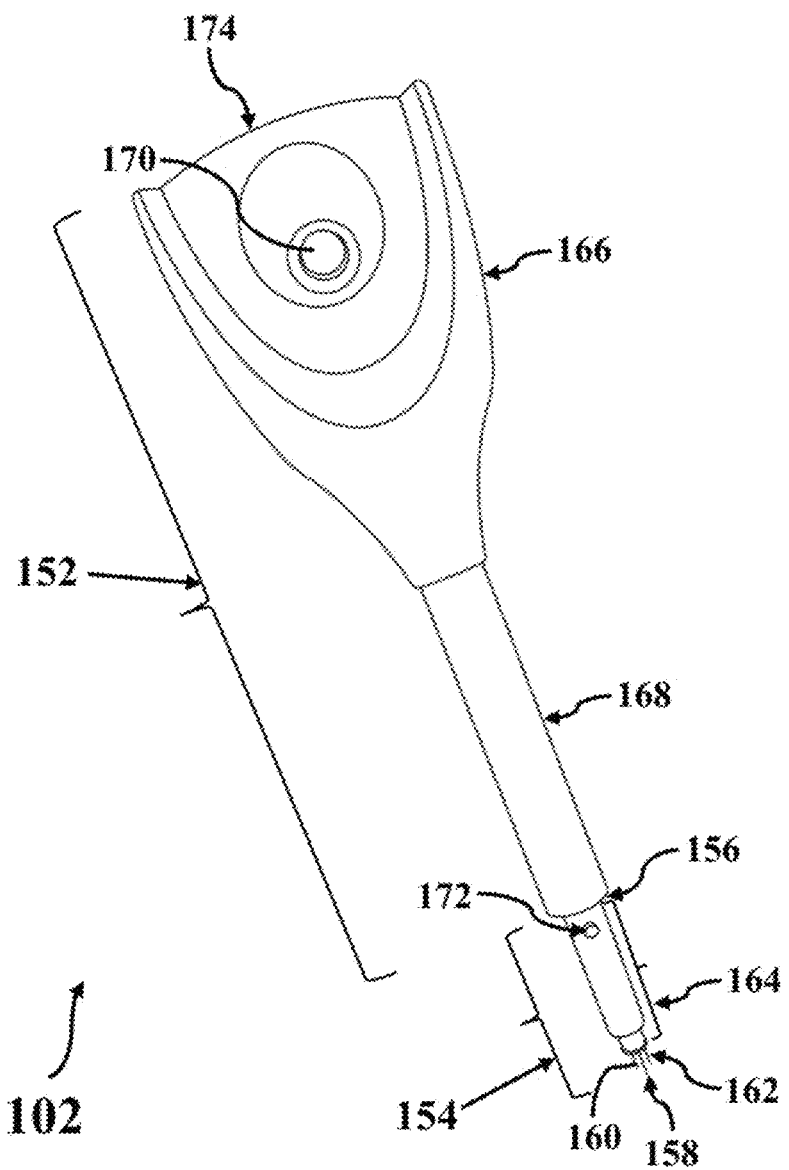
FIG. 1H illustrates a schematic view of another implementation of an exemplary cancer diagnosis probe (CDP) for in-vivo measurement of $H_2O_2$ oxidation in a living tissue, consistent with one or more exemplary embodiments of the present disclosure.

Exemplary cancer diagnosis probe (CDP) 102 may have various implementations. Exemplary cancer diagnosis probe (CDP) 102 may include an electrochemical probe with three integrated needle-shaped electrodes for in-vivo electrochemical measurements and diagnosis operations, such as cancer diagnostic techniques or methods. FIG. 1H shows a schematic view of another implementation of exemplary cancer diagnosis probe (CDP) 102 for in-vivo measurement of $H_2O_2$ oxidation in a living tissue, consistent with one or more exemplary embodiments of the present disclosure. Exemplary CDP 102 may be utilized for in-vivo measurement of $H_2O_2$ oxidation in a living tissue; thereby, allowing for detecting a cancerous state within the living tissue. Exemplary CDP 102 may include a handle 152 and a sensing part 154, where sensing part 154 may be attached to a first end 156 of handle 152. Exemplary sensing part 154 may include an exemplary working electrode 158, an exemplary counter electrode 160, and an exemplary reference electrode 162. Exemplary sensing part 154 may further include an electrode holder 164. In an exemplary embodiment, each of exemplary working electrode 15, counter electrode 160, and reference electrode 162 may be attached to electrode holder 164.

In an exemplary embodiment, handle 152 may include a handle head 166, an insertion part 168, a switch 170, and a releasing button 172. Exemplary insertion part 168 may allow for inserting CDP 102 into a biological sample, for example, an exemplary living tissue in a patient's body, a tumor in a patient's body, or a biopsied sample from a patient who may involve with cancer. Exemplary switch 170 may be located on head 166 and switch 170 may be configured to connect CDP 102 to an electrochemical stimulator-analyzer device and/or disconnect CDP 102 from the electrochemical stimulator-analyzer device. In an exemplary embodiment, the electrochemical stimulator-analyzer device may include a potentiostat device or an electrochemical workstation.

In an exemplary embodiment, CDP 102 may be connected to an electrochemical stimulator-analyzer device through an electrical connector, for example, an electrical wire, that may be connected to a second end 174 of handle 152. In another exemplary embodiment, CDP 102 may be connected to the electrochemical stimulator-analyzer device utilizing a wireless connection between CDP 102 and the electrochemical stimulator-analyzer device without any needs to connecting wires. For example, CDP 102 may be connected to the electrochemical stimulator-analyzer device via Bluetooth devices or Bluetooth modules that may be embedded in CDP 102 and the electrochemical stimulator-analyzer device. The wireless connection may allow for simplifying utilizing CDP 102 in a surgery room by a surgeon, removing redundant wires that may require to sanitize iteratively, etc.

Figure 1I:
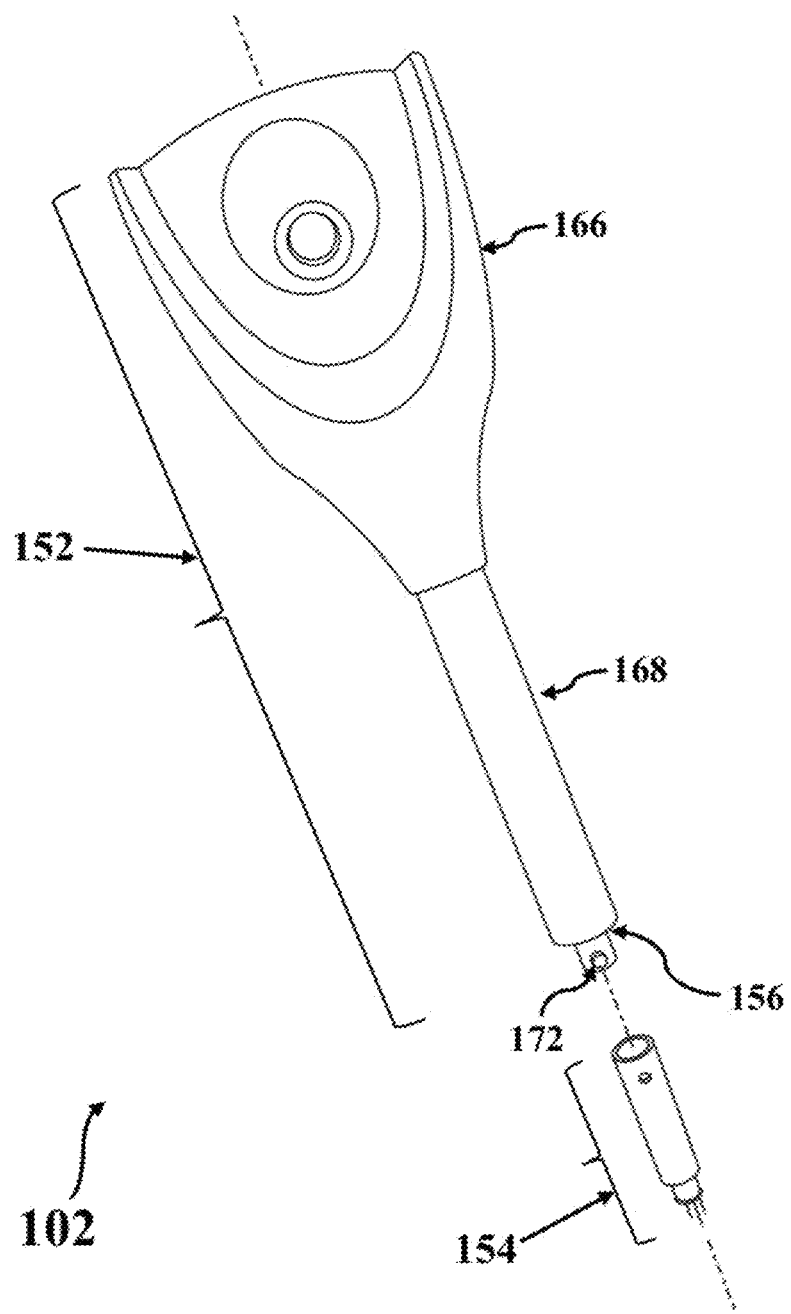
FIG. 1I illustrates a schematic view of an exemplary scenario in which an exemplary sensing part has been separated from an exemplary handle of an exemplary CDP, consistent with one or more exemplary embodiments of the present disclosure.

In an exemplary embodiment, sensing part 154 may be replaceable by releasing from handle 152 using releasing button 172. Although electrochemical measurements that may be carried out utilizing CDP 102 may be repeatable, sensing part 154 may be replaced by another sensing part 154 (a fresh/new sensing part 154) for each insertion into each part of the biological sample, which may be an obligation regarding medical ethics. Such obligations may be mandatory to avoid transferring cancer cells from one part of the biological sample to another part of the biological sample; i.e., from one part of a patient's body to another part of a patient's body. In an exemplary embodiment, sensing part 154 may be attached to insertion part 163 at the first end 156 of handle 152. Furthermore, releasing button 172 may be located on insertion part 16g in proximity to the first end 156 of handle 152. Exemplary sensing part 154 may be separated from handle 152 by pressing releasing button 172. FIG. 1I shows a schematic view of an exemplary scenario in which sensing part 154 has been separated from handle 152 of exemplary CDP 102, consistent with one or more exemplary embodiments of the present disclosure.

Referring to FIG. 1H, exemplary CDP 102 may include three exemplary electrodes including working electrode 158, counter electrode 160, and reference electrode 162. In an exemplary embodiment, working electrode 15 may comprise of a first needle coated with a layer of VAMWCNTs (an array of VAMWCNTs). VAMWCNTs may be great sensitive agents for sensing and measuring $H_2O_2$ as well as high electrically conductive agents for accurate electrochemical measurements. Exemplary counter electrode 160 may comprise of a second needle, and exemplary reference electrode 162 may comprise of a third needle. In an exemplary embodiment, the second needle may be coated with a layer of VAMWCNTs (an array of VAMWCNTs). In another exemplary embodiment, the third needle may be coated with a layer of VAMWCNTs (an array of VAMWCNTs).

In an exemplary embodiment, working electrode 158, counter electrode 160, and reference electrode 162 may be located apart from each other with a distance between each two respective electrodes of between about 1 mm and about 5 mm. In an exemplary embodiment, the distance between each two respective electrodes may be more than about 5 mm. It should be noted that the distance between each two respective electrodes may be selected depending on size of a sample, in which exemplary CDP 102 may be inserted. The distance between each two respective electrodes may be selected less than about 5 mm in order to obtain high-accurate electrochemical responses (i.e., CV diagrams) from the sample. In addition, the distance between each two respective electrodes should not be selected may be selected more than about 1 mm in order to avoid electrical noise in electrochemical measurements.

In an exemplary embodiment, each of the first needle, the second needle, and the third needle may include a biocompatible conductive needle with a diameter between about 100 µm and about 200 µm, and a length between about 0.1 cm and about 1 cm. In one embodiment, each of the first needle, the second needle, and the third needle may include a biocompatible metallic needle, for example, a steel needle. In one example, each of the first needle, the second needle, and the third needle may include an acupuncture needle.

In an exemplary embodiment, each of the first needle, the second needle, and the third needle may comprise a biocompatible conductive needle with a sensing tip. The sensing tip may have a diameter between about 100 µm and about 200 µm, and a length between about 0.1 cm and about 1 cm. In an exemplary embodiment, a layer (an array) of CNTs, for example, VAMWCNTs may be coated on each sensing tip of the first needle, the second needle, and the third needle.

Figure 1J:
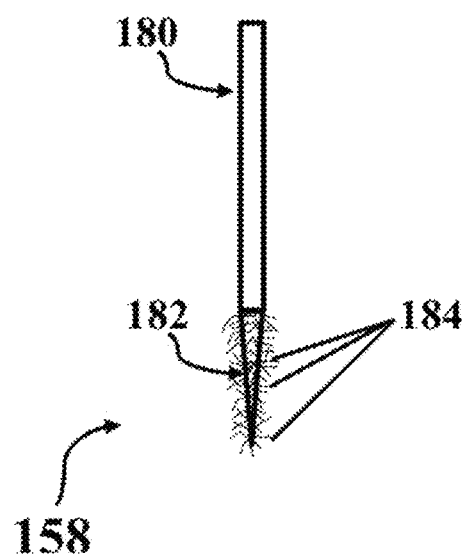
FIG. 1J illustrates a schematic view of an exemplary working electrode, consistent with one or more exemplary embodiments of the present disclosure.

FIG. 1J shows a schematic view of exemplary working electrode 158, consistent with one or more exemplary embodiments of the present disclosure. Each of the exemplary counter electrode 160 and exemplary reference electrode 162 may be similar to exemplary working electrode 158 shown in FIG. J. Exemplary working electrode 158 may include exemplary first needle 180 with sensing tip 182. In an exemplary embodiment, sensing tip 182 may be coated with an array of VAMWCNTs 184.

In an exemplary embodiment, a catalyst layer may be deposited on sensing tip 182. The catalyst layer may include a layer of Nickel (Ni) with a thickness of less than about 10 nm that may be coated on sensing tip 182 by an E-beam evaporation system at a temperature of about 120° C. with a depositing rate of about 0.1 Angstroms/s. Exemplary array of VAMWCNTs 184 may be grown on the catalyst layer using a direct current plasma enhanced chemical vapor deposition (DC-PECVD) system as described herein above.

Referring again to FIG. 1A, in an exemplary embodiment, electrochemical stimulator-analyzer 104 may include a potentiostat circuit. An exemplary potentiostat circuit may be configured to measure electrochemical responses from working electrode 106 by applying a periodic input signal to reference electrode 112 and measuring an electric current flowing from counter electrode 110 to working electrode 16. In an exemplary embodiment, an electric voltage at working electrode 108 may be amplified by a series of low noise amplifiers (LNAs) to measure a respective electrochemical response. Different electrochemical responses may be obtained for different frequencies by varying a frequency of the input signal. However, an output signal of the potentiostat circuit may tend to overshoot at high frequencies, leading to instability of measurements. In an exemplary embodiment, to prevent an excessive increase of the output signal, the output signal amplitude may be compared with a reference value utilizing a comparator circuit, and an output of the comparator circuit may be utilized to adjust an input signal amplitude so that the output signal may not exceed the reference value. In an exemplary embodiment, current buffer amplifiers (CBAs) and compensators may also utilized in the potentiostat circuit to further stabilize the output signal by lowering the impact of input signal variations on the output signal amplitude.

Figure 1K:
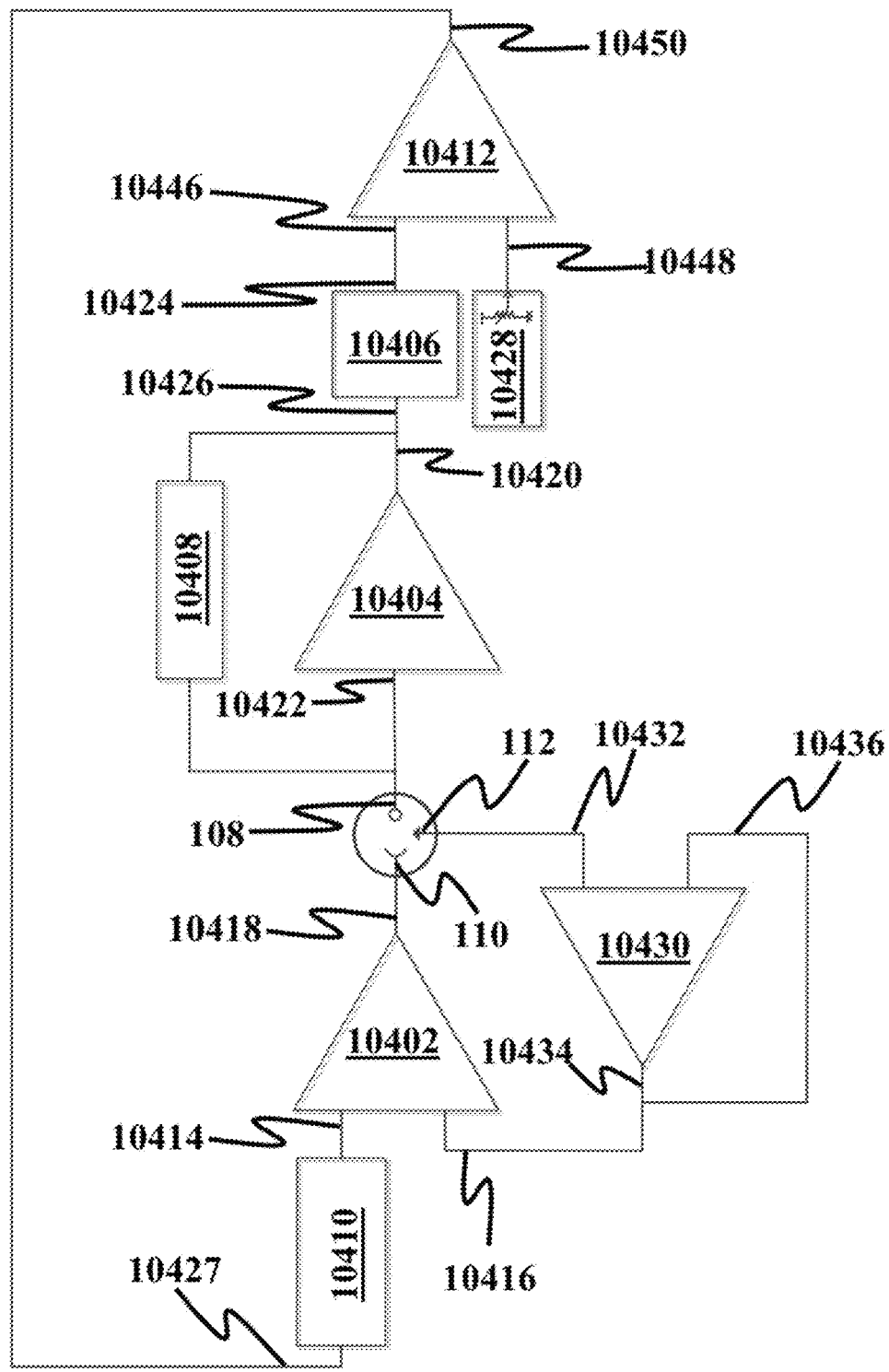
FIG. 1K shows a schematic of a first implementation of a potentiostat circuit, consistent with one or more exemplary embodiments of the present disclosure.

FIG. 1K shows a schematic of a first implementation of a potentiostat circuit, consistent with one or more exemplary embodiments of the present disclosure. In an exemplary embodiment, electrochemical stimulator-analyzer 104 may include a potentiostat circuit 104A. In an exemplary embodiment, potentiostat circuit 104A may include a control amplifier 10402, a transimpedance amplifier 10404, a peak detector circuit 10406, a feedback network 10408, a periodic wave generator 10410, and a comparator circuit 10412.

In an exemplary embodiment, control amplifier 10402 may include a first control input 10414, a second control input 10416 that may be coupled to reference electrode 112, and a control output 1041 that may be coupled to counter electrode 110. In an exemplary embodiment, control amplifier 10402 may be configured to generate a control voltage at control output 10418 by amplifying a voltage difference between first control input 10414 and second control input 10416. In an exemplary embodiment, control amplifier 10402 may include a differential amplifier. An exemplary differential amplifier may include a first input node that may be connected to first control input 10414 and a second input node connected to second control input 10416. Therefore, an exemplary differential amplifier may obtain the voltage difference between first control input 10414 and second control input 10416 by measuring a voltage difference between the first input node and the second input node. In an exemplary embodiment, the voltage difference may then multiplied by again of the differential amplifier to generate the control voltage at control output 1041. In exemplary embodiment, control amplifier 10402 may include an operational amplifier (op-amp). As a result, in exemplary embodiment, an electric potential at first control input 10414 may be transmitted to reference electrode 112 through second control input 10416 (since electric potentials at op-amp inputs may be approximately equal). Therefore, in exemplary embodiment, a voltage at reference electrode 112 may be adjusted by adjusting a voltage of first control input 10414. In an exemplary embodiment, periodic wave generator 10410 may be utilized to adjust the voltage of first control input 10414, as described below. In exemplary embodiment, exciting reference electrode 112 with an electric potential may cause a flow of an electric current from working electrode 108 to control output 10418 through counter electrode 110.

In exemplary embodiment, transimpedance amplifier 10404 may include a transimpedance output 10420 and a transimpedance input 10422. In an exemplary embodiment, transimpedance input 10422 may be connected to working electrode 108. In an exemplary embodiment, transimpedance amplifier 10404 may be configured to generate a transimpedance voltage at transimpedance output 10420 by amplifying a voltage of transimpedance input 10422. In an exemplary embodiment, the voltage of transimpedance input 10422 may be multiplied by again of the transimpedance amplifier to generate an amplified voltage at transimpedance output 10420. In exemplary embodiment, transimpedance amplifier 10404 may include an op-amp. In exemplary embodiment, transimpedance input 10422 may be connected to a negative input of an exemplary op-amp, whereas a positive input of an exemplary op-amp may be connected to ground (negative and positive inputs are not shown in FIG. 1K). As a result, in exemplary embodiment, an electric current flowing through working electrode 108 may be converted to a respective voltage at transimpedance output 10420 by passing through feedback network 10408 (since an amount of electric current that may pass through transimpedance input 10422 to an exemplary negative op-amp input may be insignificant). In other words, in exemplary embodiment, the electric current at working electrode 108 may be measured by recording a respective voltage at transimpedance output 10420).

In an exemplary embodiment, peak detector circuit 10406 may include a detector output 10424 and a detector input 10426. In an exemplary embodiment, detector input 10426 may be coupled to transimpedance output 10420. In an exemplary embodiment, peak detector circuit 10406 may be configured to detect a maximum voltage at detector input 10426 in a given period of time and transmit the maximum voltage to detector output 10420. In an exemplary embodiment, peak detector circuit 10406 may include a capacitor which may be charged by through detector input 10426. In an exemplary embodiment, peak detector circuit 10406 may further include a diode which may be forward biased when the voltage of detector input 10426 exceeds a voltage of the capacitor and may be reverse biased when the voltage of detector input 10426 becomes lower than the capacitor voltage, causing the capacitor to be disconnected from detector input 10426. As a result, the maximum voltage at detector input 10426 may be stored by an exemplary capacitor as long as the capacitor is not reset. In an exemplary embodiment, the capacitor may be connected to detector output 10420. Therefore, in an exemplary embodiment, detector output 10420 may hold the maximum voltage until a higher voltage is detected at detector input 10426 by peak detector circuit 10406. As a result, in an exemplary embodiment, peak values of electric signals at working electrode 108 (which may be transmitted to detector input 10426 through transimpedance amplifier 10404) may be detected by peak detector circuit 10406. In an exemplary embodiment, detected peak values of signals at working electrode 108 may be utilized to improve stability of potentiostat circuit 104A. In an exemplary embodiment, peak detector circuit 10406 may be configured to store the maximum voltage until the given period of time passes. In an exemplary embodiment, the given period of time may be determined based on a duration in which an electrochemical response may be recorded. For example, the given period of time may be set to an expected duration in which an exemplary CV diagram is recorded. In an exemplary embodiment, the maximum voltage may be stored in an exemplary capacitor for the given period of time. In an exemplary embodiment, peak detector circuit 10406 may be reset by discharging the capacitor after the given period of time passes.

In an exemplary embodiment, periodic wave generator 10410 may be configured to generate a periodic wave at first control input 10414 responsive to periodic wave generator 10410 becoming active In an exemplary embodiment, comparator circuit 10412 may be utilized to activate periodic wave generator 10410, as described below. When periodic wave generator 10410 is active, an exemplary periodic wave may be transmitted to counter electrode 110 through second control input 10416 to reference electrode 112. In an exemplary embodiment, periodic wave generator 10410 may be configured to adjust the voltage of first control input 10414 by generating a periodic sawtooth wave at first control input 10414, as described below. As a result, in an exemplary embodiment, counter electrode 110 may be excited with a sawtooth wave, which may facilitate recording CV diagrams from respective electrochemical responses due to moderately slow sweep rates of sawtooth waves. In an exemplary embodiment, periodic wave generator 10410 may be further configured to couple first control input 10414 to ground responsive to periodic wave generator 10410 becoming inactive. In an exemplary embodiment, comparator circuit 10412 may be utilized to deactivate periodic wave generator 10410, as described below.

Figure 1L:
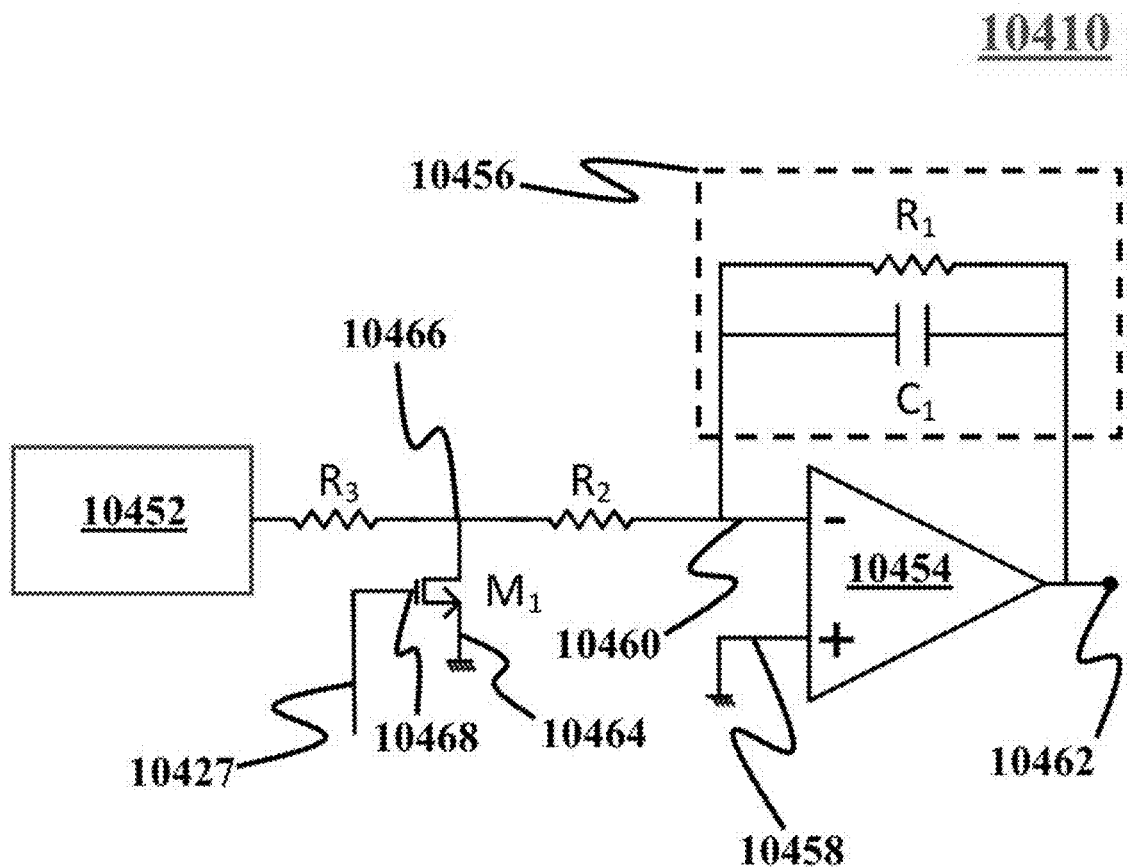
FIG. 1L shows a schematic of a periodic wave generator, consistent with one or more exemplary embodiments of the present disclosure.

FIG. 1L shows a schematic of a periodic wave generator, consistent with one or more exemplary embodiments of the present disclosure. In an exemplary embodiment, periodic wave generator 10410 may include a pulse wave generator

10452, an op-amp 10454 that may be coupled to pulse wave generator 10452, an RC circuit 10456, and a field effect transistor (FET) $M_1$.

In an exemplary embodiment, pulse wave generator 10452 may be configured to generate a periodic rectangular wave. In an exemplary embodiment, either an analog or a digital pulse generator may be utilized to implement pulse wave generator 10452. In an exemplary embodiment, a duty cycle of rectangular pulses in the periodic rectangular wave may be set to 50% to generate square pulses.

In an exemplary embodiment, op-amp 10454 may include a positive input 10458, a negative input 1460, and an op-amp output 10462. In an exemplary embodiment, positive input 10458 may be connected to ground, negative input 10460 may be coupled to an output of pulse wave generator 10452, and op-amp output 10462 may be connected to first control input 10414. In an exemplary embodiment, RC circuit 10456 may be connected between op-amp output 10462 and negative input 1460, and may include a first resistor $R_1$ and a first capacitor $C_1$ that may be connected in parallel.

In an exemplary embodiment, periodic wave generator 10416 may further include a second resistor $R_2$ and a third resistor $R_3$. In an exemplary embodiment, second resistor $R_2$ may be connected to negative input 10460 and third resistor R may be connected between second resistor $R_2$ and the output of pulse wave generator 10452. As a result, in an exemplary embodiment, an output current of pulse wave generator 10452 flowing through second resistor $R_2$ and third resistor $R_3$ may be transmitted to op-amp output 10462 through RC circuit 10456 (since an amount of electric current that may pass into op-amp 10454 through an exemplary negative input 10460 may be insignificant). Therefore, in an exemplary embodiment, the transmitted current to op-amp output 10462 may preserve a shape and frequency of the output current of pulse wave generator 10452. However, a voltage shape at op-amp output 10462 may be determined based on values of first resistor $R_1$ and first capacitor $C_1$ in RC circuit 10456. In an exemplary embodiment, different values of first resistor $R_1$ and first capacitor $C_1$ may result in different charge/discharge time for capacitor $C_1$, resulting in different voltage shapes at op-amp output 10462. For example, the voltage at op-amp output 10462 may be shaped as a sawtooth wave if the values of first resistor $R_1$ and first capacitor $C_1$ satisfy a set of exemplary conditions, as described below.

In an exemplary embodiment, first resistor $R_1$, first capacitor $C_1$, second resistor $R_2$, and third resistor $R_3$ may satisfy a set of conditions defined by the following:

$$R_1 C_1 > 100/f_{pw}$$

$$R_2 = R_3 < 0.1 R_1$$

where $f_{pw}$ is a frequency of the periodic rectangular wave. In an exemplary embodiment, the above set of conditions may ensure that the time constant of RC circuit 1456 (i.e., $R_1 C_1$) may be significantly higher than $10 T_{pw}$ where $T_{pw}$ is a period of the periodic rectangular wave, and each of second resistor $R_2$ and third resistor $R_3$ may be negligible compared to first resistor $R_1$. As a result, in an exemplary embodiment, the periodic rectangular wave may be converted to a sawtooth wave at op-amp output 10462.

In an exemplary embodiment, FET $M_1$ may include a source 10460, a drain 10466, and a gate 10468. In an exemplary embodiment, source 10460 may be connected to ground. In an exemplary embodiment, drain 1466 may be connected between second resistor $R_2$ and third resistor $R_3$, and gate 10468 may be connected to an activation input 10427. In an exemplary embodiment, FET $M_1$ may be turned off by applying a deactivation voltage to gate 10468, for example, by connecting activation input 10427 to ground. As a result, in an exemplary embodiment, op-amp 10454 may be coupled to third resistor $R_3$ through second resistor $R_2$ and therefore, an output voltage of pulse wave generator 10452 may be transmitted to op-amp output 10462. On the other hand, in an exemplary embodiment, FET $M_1$ may be turned on by applying an activation voltage (for example, a negative voltage for an n-channel FET or a negative voltage for a p-channel FET) to activation input 10427. As a result, in an exemplary embodiment, second resistor $R_2$ may be coupled to ground through FET $M_1$ and consequently, a voltage at op-amp output 10462 may be reduced as first capacitor $C_1$ is being discharged.

Referring again to FIG. 1K, in an exemplary embodiment, comparator circuit 10412 may be configured to activate periodic wave generator 10410 by providing the activation voltage to activation input 10427 of periodic wave generator 10410 responsive to a voltage of detector output 10420 being smaller than a reference voltage 10428. In an exemplary embodiment, comparator circuit 10412 may be further configured to deactivate periodic wave generator 10410 by providing the deactivation voltage to activation input 10427 responsive to a voltage of detector output 10420 being equal to or larger than reference voltage 10428. As discussed earlier, since peak values of electric signals at working electrode 108 may be detected by detector circuit 10406, utilizing comparator circuit 10412 may prevent an excessive increase in amplitudes of electric signals at working electrode 106 by deactivating periodic wave generator 10410 which may stop an excitation of reference electrode 112. As a result, in an exemplary embodiment, a flow electric current through working electrode 18 may be reduced.

In an exemplary embodiment, comparator circuit 10412 may include a first comparator input 10446, a second comparator input 10448, and a comparator output 10450. In an exemplary embodiment, first comparator input 18446 may be connected to detector output 10420 and comparator output 10450 may be connected to activation input 10427.

In an exemplary embodiment, second comparator input 10448 may include reference voltage 10428. An exemplary second comparator input 10448 may be coupled to a DC voltage supply that may include a DC voltage. In an exemplary embodiment, second comparator input 10448 may be coupled to the DC voltage supply via a variable resistor. An exemplary variable resistor may be implemented utilizing a potentiometer or a rheostat. An exemplary variable resistor may be configured to provide reference voltage 10428 to second comparator input 10448 by transmitting a fraction of the DC voltage to second comparator input 10448. In an exemplary embodiment, the fraction of the DC voltage may be determined by varying a resistivity of the variable resistor until reference voltage 1428 is obtained.

In an exemplary embodiment, comparator circuit 10412 may be configured to provide the activation voltage to comparator output 10450 responsive to a voltage of first comparator input 10446 being smaller than a voltage of second comparator input 10448. In an exemplary embodiment, comparator circuit 10412 may be further configured to provide the deactivation voltage to comparator output 10450 responsive to the voltage of first comparator input 10446 being equal to or larger than the voltage of second comparator input 10448. In an exemplary embodiment, an analog comparator may be utilized to implement comparator circuit 10412. In an exemplary embodiment, the analog comparator may be configured to generate each of the activation voltage and the deactivation voltage at an output node of the analog comparator. An exemplary output node of the analog comparator may be connected to comparator output 10450 to provide each of the activation voltage and the deactivation voltage to comparator output 10450.

In an exemplary embodiment, feedback network 10408 may be connected between detector input 10426 and transimpedance input 10422. In an exemplary embodiment, feedback network 10408 may include a feedback resistor. In an exemplary embodiment, a resistance Rr of the feedback resistor may be equal to $$\frac{V_{ref}}{I_{max}},$$

where $V_{ref}$ is a magnitude of reference voltage 10428 and $I_{max}$ is an upper limit of an electric current flowing through detector input 10426. As a result, in an exemplary embodiment, an electric voltage at detector input 10426 may not exceed $V_{ref}$ as long as the electric current flowing through detector input 10426 remains lower than $I_{max}$. In an exemplary embodiment, upper limit $I_{max}$ may be determined based on an expected maximum value of an electric current that flows through working electrode 108 (which may also flow through feedback network 10408, as discussed earlier). Therefore, in an exemplary embodiment, determination of resistance $R_f$ based on $I_{max}$ may further stabilize potentiostat circuit 104A by preventing measured electric potentials from reaching reference voltage 10428.

In an exemplary embodiment, potentiostat circuit 104A may further include a unity gain amplifier 10430 that may be connected between reference electrode 112 and second control input 10416. In an exemplary embodiment, unity gain amplifier 10430 may include a first unity gain input 10432, a unity gain output 10434, and a second unity gain input 10436. In an exemplary embodiment, first unity gain input 10432 may be connected to reference electrode 112, unity gain output 10434 may be connected to second control input 1416, and second unity gain input 10436 may be connected to unity gain output 10434 and therefore, to second control input 10416. In an exemplary embodiment, unity gain amplifier 10430 may be configured to transmit a voltage at reference electrode 112 to unity gain output 10434 by amplifying a voltage difference between first unity gain input 10432 and second unity gain input 10436. In exemplary embodiment, unity gain amplifier 10436 may include a differential amplifier. An exemplary differential amplifier may include an exemplary first input node that may be connected to first unity gain input 10432 and an exemplary second input node connected to second unity gain input 10436. Therefore, an exemplary differential amplifier may obtain the voltage difference between first unity gain input 10432 and second unity gain input 10436 by measuring a voltage difference between the exemplary first input node and the exemplary second input node. In an exemplary embodiment, the voltage difference may then be multiplied by a gain of the differential amplifier to generate an amplified voltage at unity gain output 10434. In exemplary embodiment, unity gain amplifier 10430 may include an op-amp. Therefore, in an exemplary embodiment, the voltage of first control input 10414 (i.e., an output voltage of periodic wave generator 10410) may be provided to reference electrode 112 through second unity gain input 10436 that is connected to second control input 10416, because electric potentials of first unity gain input 10432 and second unity gain input 10436 may be almost equal.

Figure 1M:
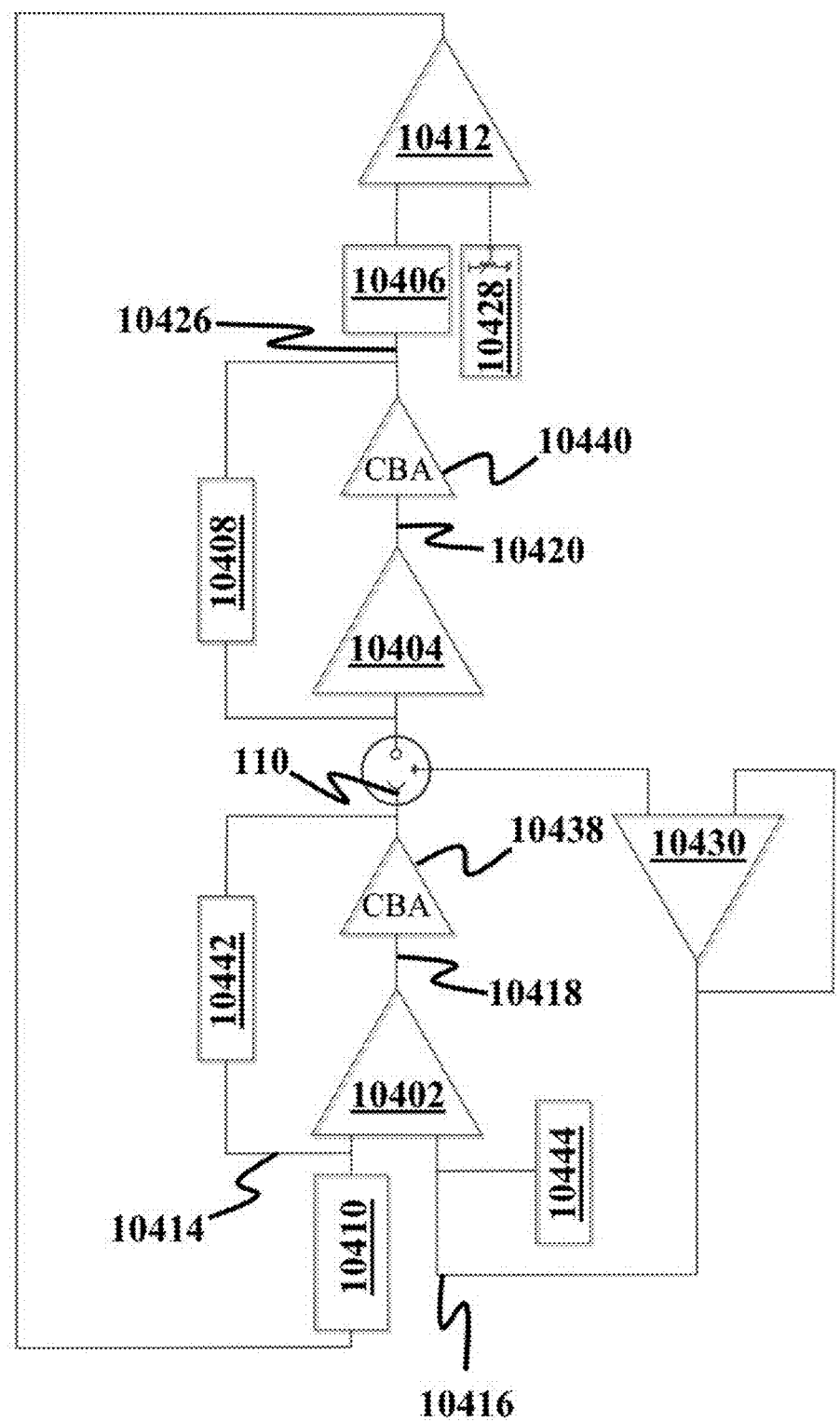
FIG. 1M shows a schematic of a second implementation of a potentiostat circuit, consistent with one or more exemplary embodiments of the present disclosure.

FIG. 1M shows a schematic of a second implementation of a potentiostat circuit, consistent with one or more exemplary embodiments of the present disclosure. In an exemplary embodiment, electrochemical stimulator-analyzer 104 may include a potentiostat circuit 104B. In an exemplary embodiment, potentiostat circuit 104B may include potentiostat circuit 104A and some additional elements. Exemplary additional elements may include current buffer amplifiers and analog compensators, which may improve stability of electrochemical stimulator-analyzer 104 at higher signal amplitudes and frequencies, thereby extending a range of frequency and/or amplitude in which electrochemical stimulator-analyzer 104 may operate. In an exemplary embodiment, potentiostat circuit 104B may further include a first current buffer amplifier (CBA) 10438 that may be connected between control amplifier 10402 and counter electrode 110. In an exemplary embodiment, first CBA 10438 may be configured to transfer an electric current flowing through control output 10418 to counter electrode 110.

In an exemplary embodiment, potentiostat circuit 104B may further include a second CBA 10440 that may be connected between transimpedance amplifier 10404 and peak detector circuit 10406. In an exemplary embodiment, second CBA 10440 may be configured to transfer an electric current flowing through transimpedance output 10420 to detector input 10426.

In an exemplary embodiment, potentiostat circuit 104B may further include a first analog compensator 10442 that may be connected between counter electrode 110 and first control input 10414. In an exemplary embodiment, first analog compensator 10442 may be configured to compensate voltage variations at counter electrode 110 responsive to voltage variations at first control input 10414. In an exemplary embodiment, first analog compensator 10442 may include a first compensation capacitor. In an exemplary embodiment, potentiostat circuit 104B may further include a second analog compensator 10444 that may be connected to second control input 10416. In an exemplary embodiment, second analog compensator 10444 may be configured to compensate voltage variations at second control input 10416. In an exemplary embodiment, second analog compensator 10444 may include a second compensation capacitor and a compensation resistor that may be connected in series. In an exemplary embodiment, values of the first compensation capacitor, the second compensation capacitor, and the compensation resistor may be set to about 22 pF, 47 pF, and 4.99 kM, respectively. As a result, in an exemplary embodiment, a scan rate of about 1 V/μs may obtained at a frequency of about $f_{pw}$=1 MHz for recording electrochemical responses utilizing potentiostat circuit 104B, which may be suitable for high speed applications.

Figure 2A:
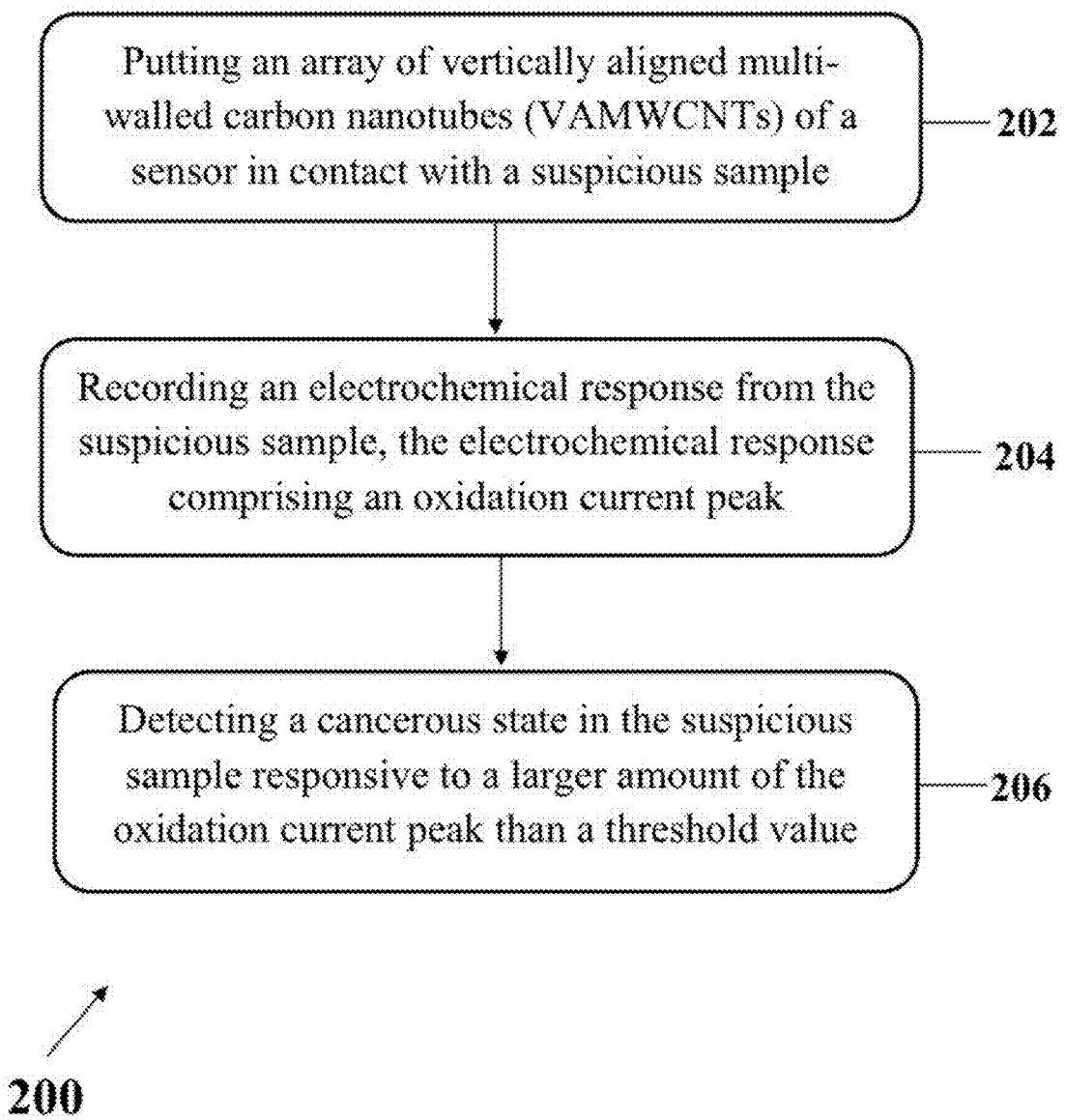
FIG. 2A illustrates an exemplary implementation of a method for cancer diagnosis, consistent with one or more exemplary embodiments of the present disclosure.

In another aspect of the present disclosure, a method for cancer diagnosis is disclosed. FIG. 2A shows an exemplary implementation of method 200 for cancer diagnosis, consistent with one or more exemplary embodiments of the present disclosure. Method 200 may include putting an array of vertically aligned multi-walled carbon nanotubes (VAMWCNTs) of a sensor in contact with a suspicious sample (step 202), recording an electrochemical response from the suspicious sample, where the electrochemical response may include an oxidation current peak (step 204), and detecting a cancerous state in the suspicious sample responsive to a larger amount of the oxidation current peak than a threshold value (step 266). The sensor may be similar to exemplary sensor 102 described hereinabove.

Step 202 may include putting the army of vertically aligned multi-walled carbon nanotubes (VAMWCNTs) of the sensor in contact with the suspicious sample. In an exemplary implementation, putting the array of VAMWCNTs of the sensor in contact with the suspicious sample may include one of dropping the suspicious sample onto the sensor, placing the suspicious sample onto the sensor, squeezing the sensor into the suspicious sample, inserting the sensor into the suspicious sample, and combinations thereof.

In an exemplary embodiment, the suspicious sample may include one of a liquid suspicious sample, a solid suspicious sample, and combinations thereof. In an exemplary embodiment, the suspicious sample may include one of a plurality of cell lines, a biopsied sample from a human or animal body, a removed sample from a human or animal body by surgery, a portion of a living tissue in a human or animal body, and a portion of a living tissue in a human or animal body during surgery.

In an exemplary implementation, the sensor may be similar to sensor 102 and may include a substrate, a catalyst layer, and three arrays of vertically aligned multi-walled carbon nanotubes (VAMWCNTs) grown on the catalyst layer. Three arrays of VAMWCNTs may include a working electrode that may include a first array of VAMWCNTs, a reference electrode that may include a second array of VAMWCNTs, and a counter electrode that may include a third array of VAMWCNTs. In an exemplary implementation, the sensor may further include a passivation layer between the substrate and the catalyst layer.

In an exemplary implementation, the sensor may include one of a CNT based electrochemical chip similar to exemplary CNT based electrochemical chip 102 shown in FIG. 1B, and a cancer diagnosis probe (CDP) similar to exemplary CDP 12 shown in FIG. 1E. The substrate of the cancer CDP may include three needles, where each needle of the three needles may be coated by an array of VAMWCNTs of the three arrays of VAMWCNTs. In an exemplary implementation, the sensor may include exemplary sensor 102 as shown schematically in FIGS. 1A, 1B, and 1E.

Figure 2B:
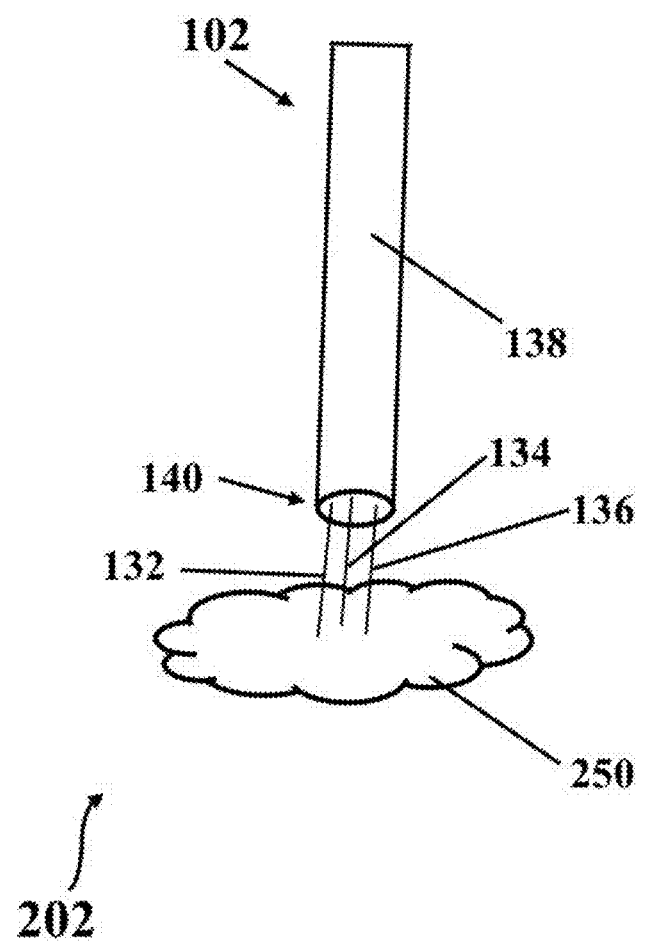
FIG. 2B illustrates a schematic implementation of putting the array of vertically aligned multi-walled carbon nanotubes (VAMWCNTs) grown on tip of each needle electrode of three needles electrodes of exemplary CDP in contact with exemplary suspicious sample, consistent with one or more exemplary embodiments of the present disclosure.

FIG. 2B shows a schematic implementation of step 262 that may include putting the army of vertically aligned multi-walled carbon nanotubes (VAMWCNTs) grown on tip of each needle electrode of three needles electrodes 132, 134, and 138 of exemplary cancer diagnosis probe (CDP) 102 in contact with exemplary suspicious sample 250, consistent with one or more exemplary embodiments of the present disclosure. Step 102 may include inserting or squeezing exemplary cancer diagnosis probe (CDP) 102 in exemplary suspicious sample 258.

In an exemplary implementation, putting the army of VAMWCNTs of exemplary sensor 102 in contact with the suspicious sample may take place temporarily or over a time duration of less than 1 seconds for a real-time cancer diagnosis case. In an exemplary embodiment, putting the array of VAMWCNTs of exemplary sensor 102 in contact with the suspicious sample may take place temporarily or over a time duration of less than 1 seconds for in vivo or in vitro cancer diagnosis using exemplary sensor which may be an exemplary CDP or exemplary CNT based electrochemical chip. In an exemplary embodiment, putting the array of VAMWCNTs of exemplary sensor 102 in contact with the suspicious sample may be for a time duration of about 12 hours or more for in vitro cancer diagnosis cases with high levels of accuracy utilizing exemplary CNT based electrochemical chip 102. In an exemplary embodiment, putting the array of VAMWCNTs of exemplary sensor 102 in contact with the suspicious sample may be carried out in a time duration of about 0.1 seconds to about 24 hours.

Step 204 may include recording the electrochemical response from the suspicious sample, where the electrochemical response may include an oxidation current peak. In an exemplary embodiment, the electrochemical response may include a cyclic voltammetry (CV) diagram of hypoxic glycolysis chemical reaction in biological cells within the suspicious sample. In an exemplary embodiment, the electrochemical response may include a cyclic voltammetry (CV) diagram of $H_2O_2$ related oxidation/reduction chemical reaction in biological cells within the suspicious sample. The concentration of $H_2O_2$ may be in correlation with the hypoxia glycolysis occurred in tumor cells. In an exemplary embodiment, the electrochemical response may include a cyclic voltammetry (CV) diagram of $H_2O_2$ oxidation that may be electrically sensed by VAMWCNTs in biological cells within the suspicious sample. In an exemplary embodiment, the electrochemical response may include an oxidation current peak of exemplary CV diagram of hypoxic glycolysis chemical reaction in biological cells within a suspicious sample.

In an exemplary implementation, recording the electrochemical response from the suspicious sample (step 204) may include connecting the sensor to an electrochemical stimulator-analyzer, applying an electrical voltage on the sensor using the electrochemical stimulator-analyzer, and measuring the electrochemical response from the suspicious sample using the electrochemical stimulator-analyzer. In an exemplary embodiment, the electrochemical stimulator-analyzer may include a potentiostat.

Step 206 may include detecting the cancerous state in the suspicious sample responsive to a larger amount of the oxidation current peak than a threshold value. In an exemplary embodiment, the threshold value may include an oxidation current peak of about 700 μA or more when a time duration of putting the array of vertically aligned multi-walled carbon nanotubes (VAMWCNTs) of the sensor in contact with the suspicious sample (step 202) may be more than about 12 hours. In an exemplary embodiment, the threshold value may include an oxidation current peak of about 80 μA or more when a time duration of putting the army of vertically aligned multi-walled carbon nanotubes (VAMWCNTs) of the sensor in contact with the suspicious sample (step 202) may be about 5 seconds or less.

Figure 2C:
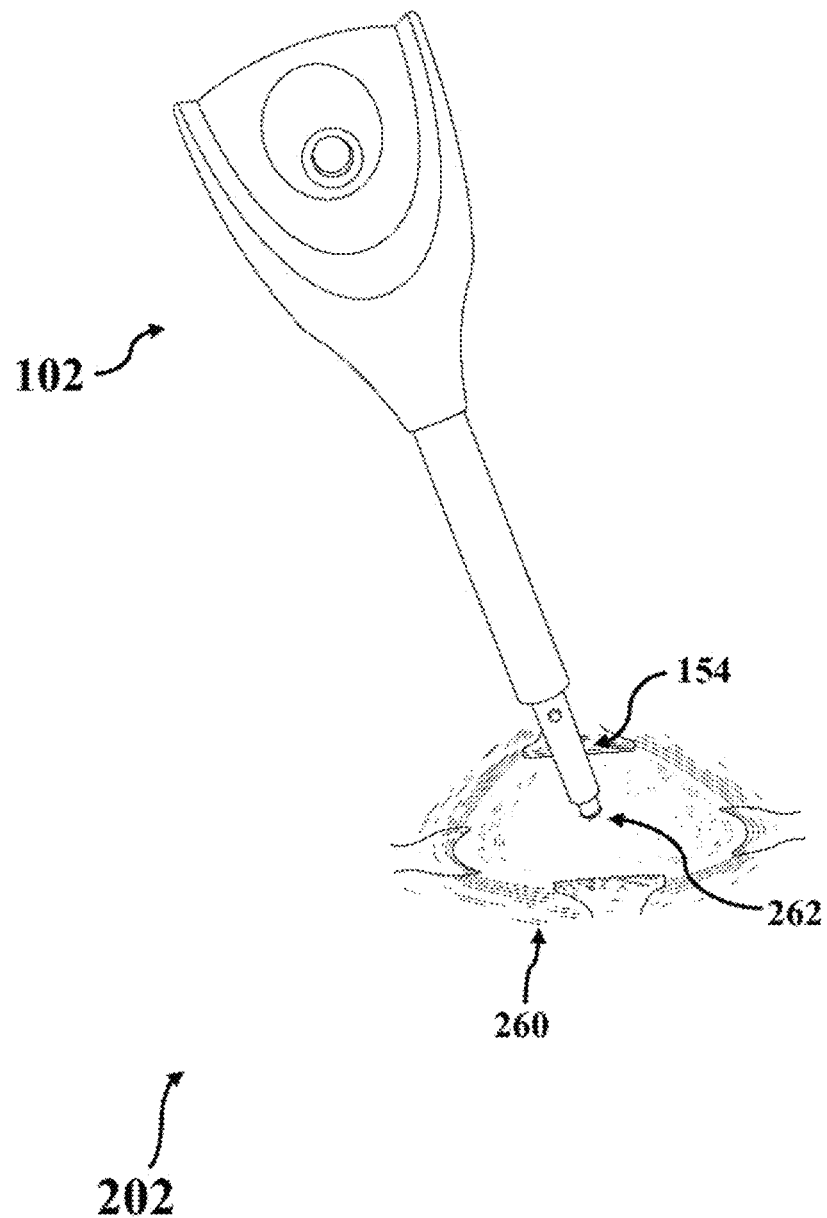
FIG. 2C illustrates a schematic view of another exemplary implementation of putting exemplary electrodes of exemplary CDP in contact with an exemplary portion of a living tissue, consistent with one or more exemplary embodiments of the present disclosure.

FIG. 2C shows an implementation of detecting the cancerous state in the suspicious sample (step 206), consistent with one or more exemplary embodiments of the present disclosure. Detecting the cancerous state in the suspicious sample (step 206) may include recording a reference electrochemical response from a reference solution, where the reference electrochemical response may include a reference oxidation current peak (step 208), comparing the electrochemical response with the reference electrochemical response (step 210), and detecting the cancerous state in the suspicious sample responsive to a larger oxidation current peak of the electrochemical response in comparison with the reference oxidation current peak (step 212). In an exemplary embodiment, the reference solution may include a lactate solution with a lactate concentration of about 0.05 mM or more.

Disclosed systems, methods and sensors herein may have various implementations, all based on measuring $H_2O_2$ oxidation current peak due to hypoxia glycolysis and reverse Warburg phenomena in cancer cells in order to for diagnosing cancerous tumors in real-time and with highly accuracy. Exemplary CDP 102 may be utilized via exemplary system 100 and/or utilizing exemplary method 200 for non-invasively diagnosing, in real-time, a presence of pre-neoplastic/neoplastic cells in either internal or external margins of a patient during tumor surgery, for example, breast cancer surgery. The exemplary systems, methods, and sensors may be capable of instantaneously determining an amount of $H_2O_2$ released from cancer or atypical cells, through reverse Warburg effect and hypoxia assisted glycolysis pathways, in a quantitative electrochemical manner. Reverse Warburg effect and hypoxia assisted glycolysis pathways may lead to high levels of $H_2O_2$ concentration in cancerous tumors in comparison with healthy tissues. Due to limited precision of conventional H&E pathology of biopsy samples and requirement to time-consuming preparation and consideration of many blocks and slides for complete evaluation of biopsy samples, exemplary systems, methods, and sensors of the present disclosure may be applied for cancer diagnosis, which may be based on live detecting the hypoxia glycolytic functions of high risk/premalignant cells based on the $H_2O_2$ released from cancer or atypical cells (through reverse Warburg effect 10 and hypoxia assisted glycolysis pathways). The exemplary systems, methods, and sensors may be utilized for diagnosing all cancerous tumors, in which hypoxia glycolysis may be the main differential mechanism between the phenotypes of healthy, precancerous and cancerous cells.

In an exemplary implementation, method 200 may further include fabrication of exemplary sensor 102 (not illustrated), for example, exemplary CDP 102. In an exemplary implementation, method 200 may be utilized for in-vivo cancer diagnosis within a living tissue utilizing exemplary CDP 102.

Figure 2D:
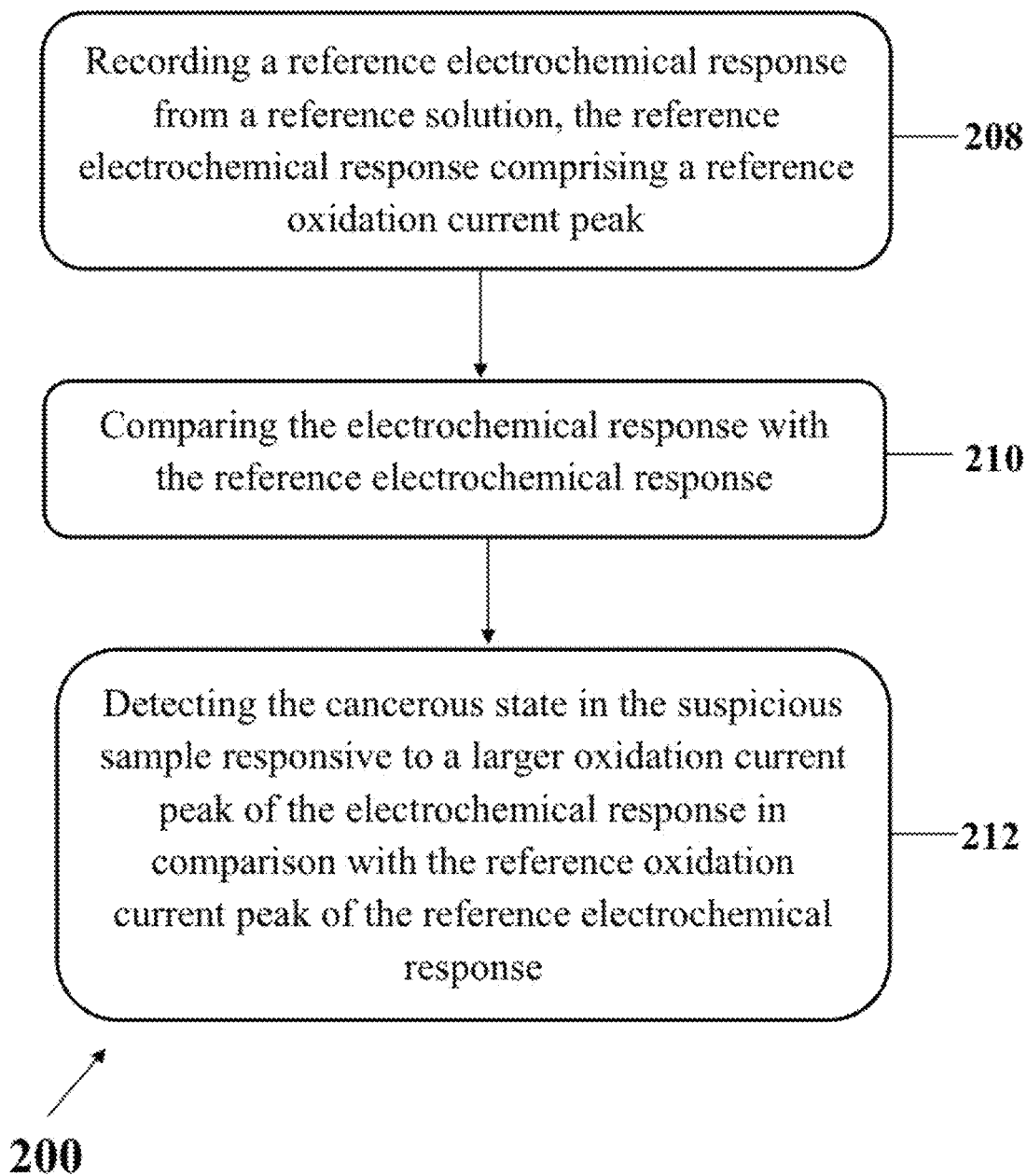
FIG. 2D illustrates an implementation of detecting the cancerous state in the suspicious sample, consistent with one or more exemplary embodiments of the present disclosure.
Figure 2E:
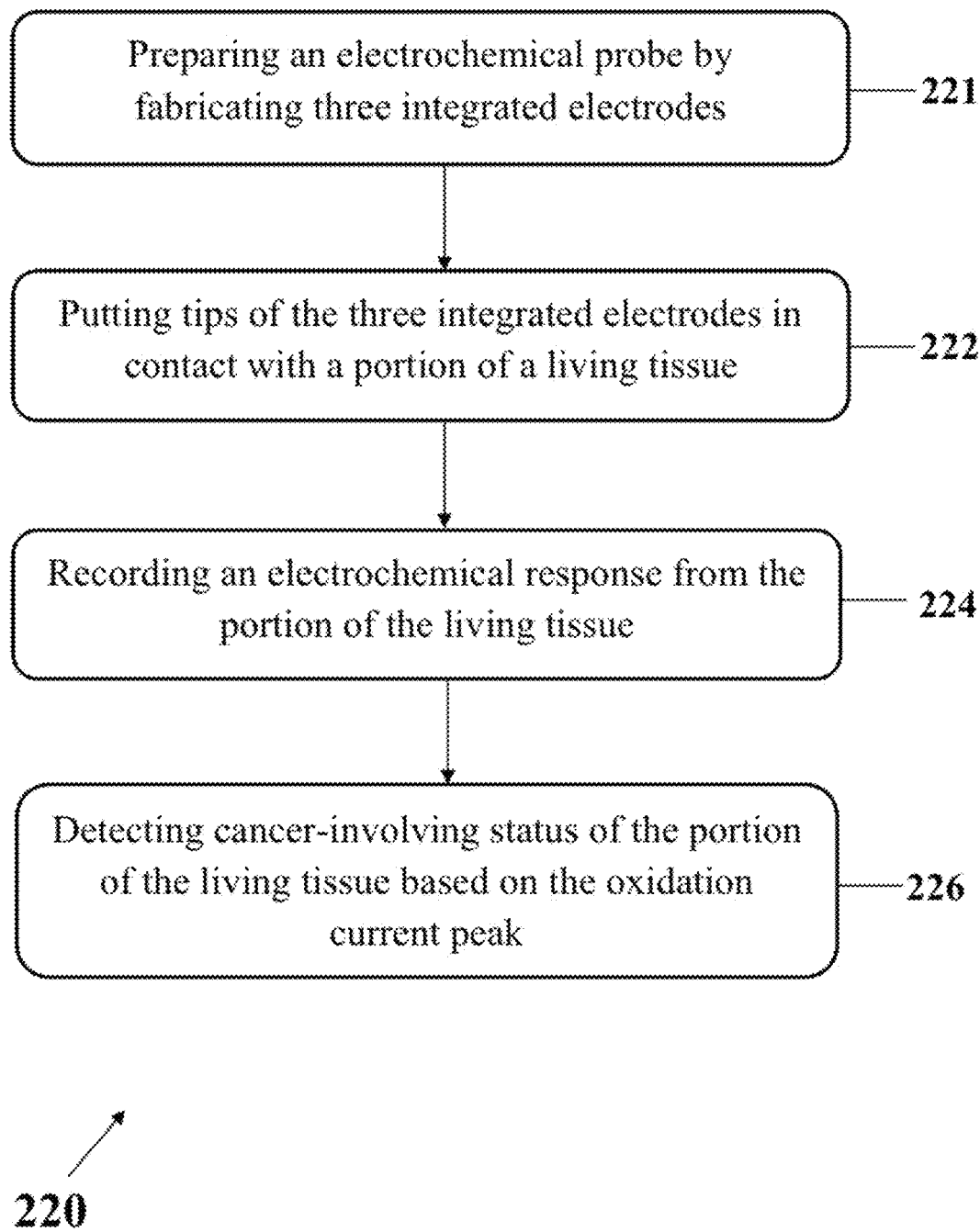
FIG. 2E illustrates an exemplary implementation of an exemplary method for in-vivo cancer diagnosis within a living tissue, consistent with one or more exemplary embodiments of the present disclosure.

FIG. 2E shows an exemplary implementation of exemplary method 220 for in-vivo cancer diagnosis within a living tissue, consistent with one or more exemplary embodiments of the present disclosure. Exemplary method 220 may be similar to method 200 shown in FIG. 2A. Exemplary method 220 may include preparing an electrochemical probe by fabricating three integrated electrodes (step 221), putting tips of the three integrated electrodes in contact with a portion of the living tissue by inserting the tips of the three integrated electrodes into the portion of the living tissue (step 222), recording an electrochemical response from the portion of the living tissue, where the electrochemical response may include a cyclic voltammetry (CV) diagram with an oxidation current peak of hypoxic glycolysis chemical reaction in biological cells within the portion of the living tissue (step 224), and detecting a cancer-involving status of the portion of the living tissue based on the oxidation current peak (step 226).

Figure 2F:
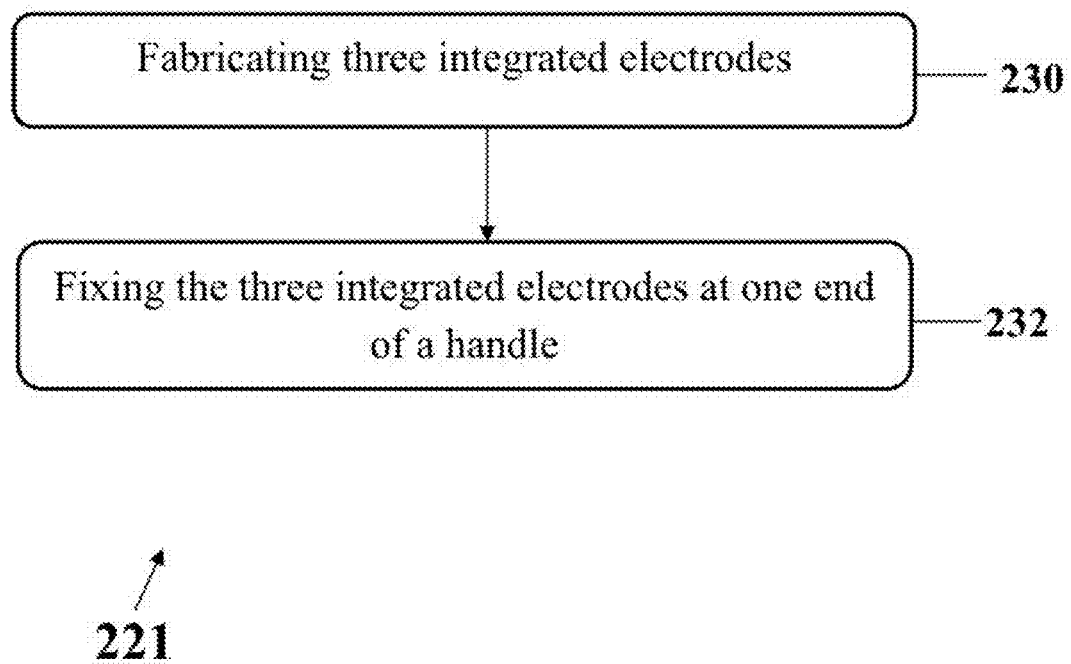
FIG. 2F illustrates an exemplary implementation of preparing an exemplary electrochemical probe similar to the exemplary CDP, consistent with one or more exemplary embodiments of the present disclosure.

In detail, step 221 may include preparing an electrochemical probe. In an exemplary embodiment, the electrochemical probe may be similar to exemplary CDP 182 that is shown in FIGS. 1E, 1H and 1I. FIG. 2F shows an exemplary implementation of preparing an exemplary electrochemical probe similar to CDP 102 (step 221), consistent with one or more exemplary embodiments of the present disclosure. Step 221 may include fabricating three integrated electrodes by coating a layer of vertically aligned multi-walled carbon nanotubes (VAMWCNTs) on tips of three electrically conductive biocompatible needles (step 230), and fixing the three integrated electrodes at one end of a handle (or a holding member)(step 232).

Figure 2G:
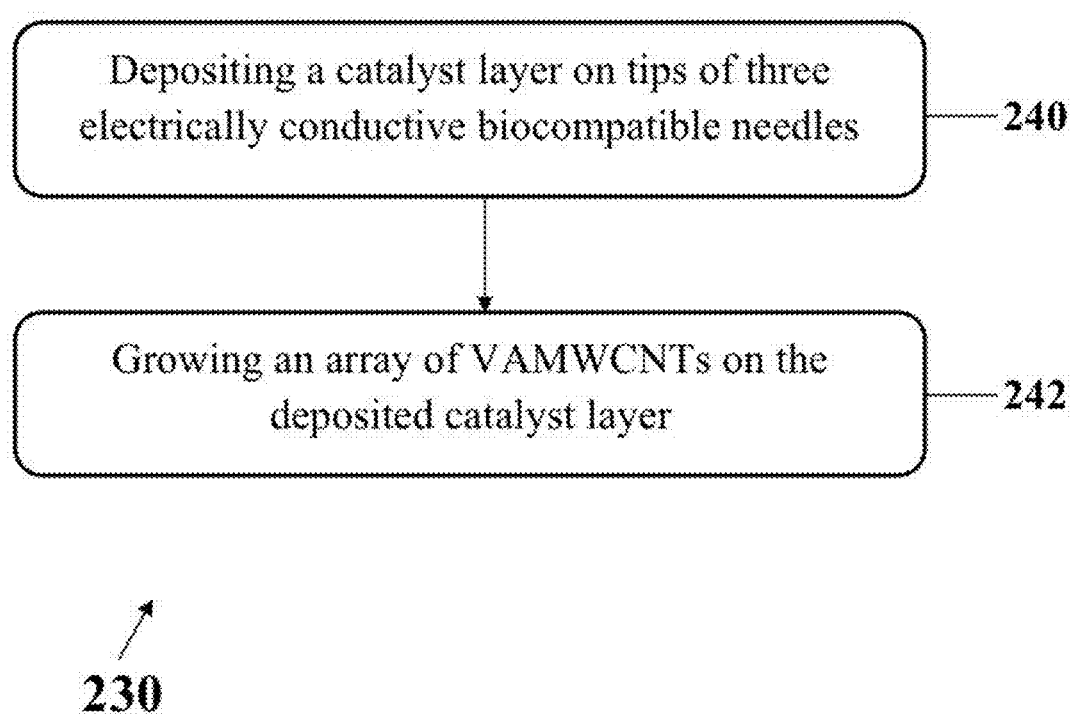
FIG. 2G illustrates an exemplary implementation of fabricating three integrated electrodes by coating a layer of vertically aligned multi-walled carbon nanotubes (VAMWCNTs) on tips of three electrically conductive biocompatible needles, consistent with one or more exemplary embodiments of the present disclosure.

FIG. 2G shows an exemplary implementation of fabricating three integrated electrodes by coating a layer of vertically aligned multi-walled carbon nanotubes (VAMWCNTs) on tips of three electrically conductive biocompatible needles (step 230), consistent with one or more exemplary embodiments of the present disclosure. Step 230 may include depositing a catalyst layer on the tips of the three electrically conductive biocompatible needles (step 240), and growing an array of VAMWCNTs on the deposited catalyst layer (step 242). In an exemplary implementation, step 230 may include fabricating three integrated electrodes by coating three respective layers of VAMWCNTs on tips of three electrically conductive biocompatible needles.

In detail, step 240 may include depositing a catalyst layer on tips of three electrically conductive biocompatible needles. In an exemplary implementation, step 240 may include depositing three catalyst layers on three respective tips of the three electrically conductive biocompatible needles. In an exemplary implementation, step 240 may include depositing a respective layer of Nickel (Ni) with a thickness of less than about 10 nm using an E-beam evaporation system at a temperature of about 120° C. with a depositing rate of about 0.1 Angstroms/s on each tip of the tips of the three electrically conductive biocompatible needles.

Figure 2H:
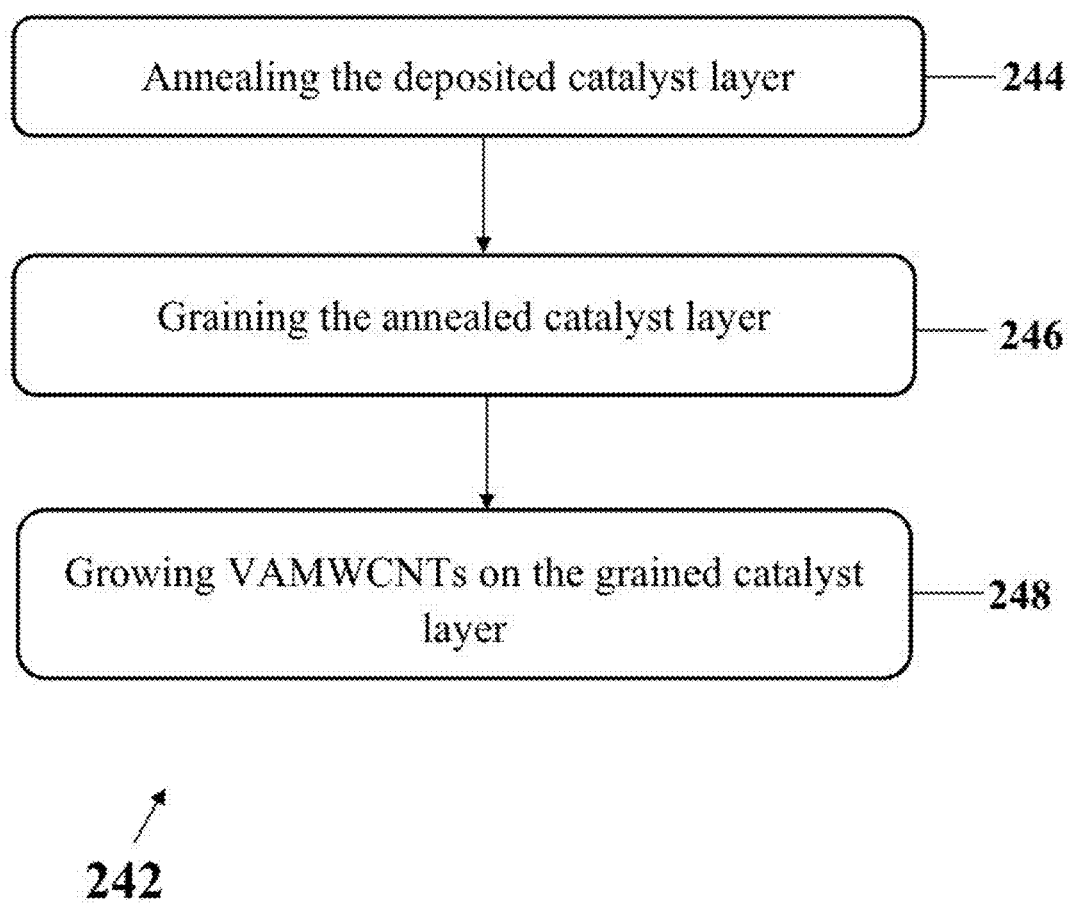
FIG. 2H illustrates an exemplary implementation of growing an array of VAMWCNTs on exemplary deposited catalyst layer, consistent with one or more exemplary embodiments of the present disclosure.

Furthermore, step 242 may include growing an array of VAMWCNTs on the deposited catalyst layer on each tip of the tips of the three electrically conductive biocompatible needles. FIG. 2H shows an exemplary implementation of growing an array of VAMWCNTs on the deposited catalyst layer (step 242), consistent with one or more exemplary embodiments of the present disclosure. Step 242 may include annealing the deposited catalyst layer at a temperature of about 680° C. in an $H_2$ environment with a flow rate of about 20 standard cubic centimeters per minute (sccm) to 35 sccm for about 30 minutes (step 244), graining the annealed catalyst layer by plasma hydrogenation of surface of the catalyst layer for about 5 minutes with an intensity of about 5.5 W·cm$^{-2}$ (step 246), and growing VAMWCNTs on the grained catalyst layer in a chamber by introducing a plasma comprising a mixture of $C_2H_2$ with flow rate of about 5 sccm and $H_2$ with flow rate of about 35 sccm to the chamber for about 15 minutes (step 248). In an exemplary implementation, graining the annealed catalyst layer by plasma hydrogenation of surface of the catalyst layer for about 5 minutes with an intensity of about 5.5 W·cm$^{-2}$ (step 246) may result in catalyst graining, and formation of nano-sized islands of the catalyst.

Referring to FIG. 2E, step 222 may include putting tips of the three integrated electrodes in contact with a portion of the living tissue by inserting the tips of the three integrated electrodes into the portion of the living tissue. In an exemplary implementation, step 222 may include putting tips of exemplary three integrated electrodes of exemplary CDP 102 in contact with a portion of a living tissue by inserting the tips of the three integrated electrodes into the portion of the living tissue. As used herein, "the portion of the living tissue" may refer to an implementation of "the suspicious sample" described hereinabove, which may include a biological sample that may be suspicious to be cancerous. FIG. 2C shows a schematic view of another exemplary implementation of putting electrodes 158, 160, and 162 of exemplary CDP 162 in contact with exemplary portion 262 of living tissue 260 (step 222), consistent with one or more exemplary embodiments of the present disclosure. Putting electrodes 158, 160, and 162 of exemplary CDP 162 in contact with exemplary portion 262 of living tissue 260 may include inserting sensing part 154 into exemplary portion 262 of living tissue 260.

In an exemplary implementation, putting electrodes 158, 160, and 162 of exemplary CDP 102 in contact with exemplary portion 262 of living tissue 260 may include at least one of putting electrodes 158, 160, and 162 inside portion 262 of living tissue 260, inserting electrodes 158, 160, and 162 inside portion 262 of living tissue 260, interacting a secretion of living tissue 260 with electrodes 158, 160, and 162, squeezing electrodes 158, 160, and 162 inside portion 262 of living tissue 260, and combinations thereof. In an exemplary embodiment, inserting electrodes 158, 160, and 162 inside portion 262 of living tissue 260 may include penetrating electrodes 158, 160, and 162 into portion 262 of living tissue 260. In one implementation, putting electrodes 158, 160, and 162 of exemplary CDP 102 in contact with portion 262 of living tissue 260 (step 222) may be done during at least one of a surgery operation, a mastectomy operation, a biopsy operation, an endomicroscopy operation, an optical biopsy operation, a clinical examination of a patient, and combinations thereof. In one implementation, putting electrodes 158, 160, and 162 of exemplary CDP 102 in contact with exemplary portion 262 of living tissue 260 may include inserting electrodes 158, 160, and 162 of exemplary CDP 102 in portion 262 of living tissue 260 with an insertion depth between about 3 mm and about 5 mm.

In an exemplary embodiment, portion 262 of living tissue 26 may be in liquid form or solid for. In further detail, in an exemplary embodiment, portion 262 may comprise at least one of a liquid sample suspicious to be cancerous, a solid sample suspicious to be cancerous, and combinations thereof.

In an exemplary embodiment, portion 262 of living tissue 260 may include at least one of a biopsied sample from a human or animal body, a sample resected from a human or animal body by surgery, a portion of living tissue 260 in a human or animal body near to skin, an exemplary portion 262 of living tissue 260 of a human or animal body that may be accessible during surgery (tumor removal surgery) or biopsy operation, a suspicious mass to be cancerous in a human or animal body, a removed sample from a human or animal body by surgery, and combinations thereof.

Moreover, step 224 may include recording an electrochemical response from the portion of the living tissue, where the electrochemical response may include a cyclic voltammetry (CV) diagram with an oxidation current peak of hypoxic glycolysis chemical reaction in biological cells within the portion of the living tissue. In an exemplary implementation, step 224 may include recording a CV diagram with an oxidation current peak of hypoxic glycolysis chemical reaction from portion 262 of living tissue 260 utilizing exemplary CDP 102. In an exemplary implementation, recording the electrochemical response from the suspicious sample (step 224) may include recording the electrochemical response from exemplary suspicious sample 250 (FIG. 2B) or exemplary portion 262 of living tissue 260 (FIG. 2C). In an exemplary embodiment, the electrochemical response may be recorded using exemplary CDP 102 that is shown in FIGS. 1E, 1H and 1I. In an exemplary embodiment, the electrochemical response may include a cyclic voltammetry (CV) diagram with an oxidation current peak of hypoxic glycolysis chemical reaction in biological cells within exemplary portion 262 of the living tissue 260.

In an exemplary implementation, recording the electrochemical response from exemplary portion 262 of living tissue 260 may include connecting exemplary CDP 102 to an electrochemical stimulator-analyzer, applying a set of electrical potentials to exemplary CDP 102 using the electrochemical stimulator-analyzer, and recording a set of electrical currents respective to the applied set of electrical potentials from exemplary portion 262 of the living tissue 260 using the exemplary CDP 102 and the electrochemical stimulator-analyzer. In an exemplary embodiment, each of the measured set of electrical current may flow from counter electrode 110 to working electrode 108 when a respective electrical potential of the set of electrical potentials is applied to CDP 102.

In an exemplary implementation, applying the set of electrical potentials to exemplary CDP 102 may include applying a sweeping range of electrical potentials between about −1 V and about 1 V to exemplary working electrode 158 or exemplary working electrode 108. In an exemplary implementation, applying the set of electrical potentials to exemplary CDP 102 may include applying a sweeping range of electrical potentials between about −0.8 V and about 0.8 V to exemplary working electrode 158 or exemplary working electrode 108. In an exemplary embodiment, the electrochemical stimulator-analyzer may comprise a potentiostat.

In detail, step 226 may include detecting a cancer-involving status of the portion of the living tissue based on the oxidation current peak. In an exemplary implementation, step 226 may include detecting a cancer-involving status of exemplary suspicious sample 250 (FIG. 2B) or exemplary portion 262 of living tissue 260 (FIG. 2C). In an exemplary implementation, detecting the cancer-involving status of portion 262 of living tissue 260 based on the oxidation current peak (step 226) may include detecting a healthy state at portion 262 of living tissue 260 responsive to a value (an amount) of the oxidation current peak being smaller than a first threshold value, detecting a cancerous state at portion 262 of living tissue 260 responsive to the value of the oxidation current peak being larger than a second threshold value, and detecting a moderately cancer-involved state at the portion 262 of living tissue 260 responsive to the value of the oxidation current peak being between the first threshold value and the second threshold value.

In an exemplary implementation, exemplary method 220 utilizing exemplary CDP 102 may be utilized for in-vivo cancer diagnosis within all tissues in a human or animal's body. In an exemplary implementation, exemplary method 220 utilizing exemplary CDP 102 may be utilized for in-vivo cancer diagnosis of all cancerous tumors, in which hypoxia glycolysis may be the main differential mechanism between the phenotypes of healthy, precancerous and cancerous cells. In an exemplary implementation, detecting the cancer-involving status of portion 262 of living tissue 260 based on the oxidation current peak (step 226) may include detecting presence of human breast cancer in a portion of a breast tissue responsive to the value of the oxidation current peak being equal to 203 µA or more, detecting the healthy state at the portion of the breast tissue responsive to the value of the oxidation current peak being equal to 137 µA or less, and detecting a moderately breast cancer-involved state at the portion of the breast tissue responsive to the value of the oxidation current peak being between 137 µA and 203 µA.

In an exemplary implementation, detecting the cancer-involving status of portion 262 of living tissue 260 based on the oxidation current peak (step 226) may include detecting presence of cervical cancer in a portion of a cervical tissue (cervix) responsive to the value of the oxidation current peak being equal to 145 µA or more, detecting the healthy state at the portion of the cervical tissue (cervix) responsive to the value of the oxidation current peak being equal to 115 µA or less, and detecting a moderately cervical cancer-involved state (or a suspicious-involved state) at the portion of the cervical tissue (cervix) responsive to the value of the oxidation current peak being between 115 µA and 145 µA.

Figure 2I:
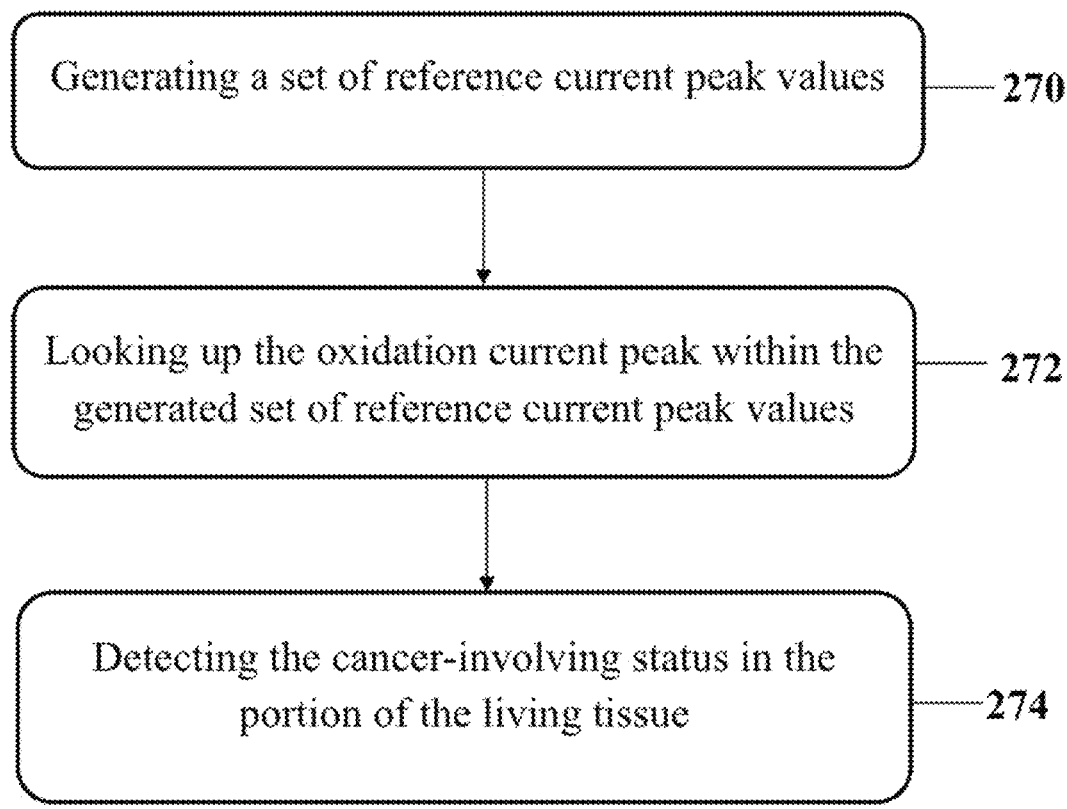
FIG. 2I shows an exemplary implementation of detecting the cancer-involving status of the exemplary portion of the exemplary living tissue based on the oxidation current peak, consistent with one or more exemplary embodiments of the present disclosure.

FIG. 2I shows an exemplary implementation of detecting the cancer-involving status of portion 262 of living tissue 260 based on the oxidation current peak (step 226), consistent with one or more exemplary embodiments of the present disclosure. In detail, detecting the cancer-involving status of portion 262 of living tissue 260 based on the oxidation current peak (step 226) may include generating a set of reference current peak values (step 270), looking up the oxidation current peak within the generated set of reference current peak values (step 272), and detecting the cancer-involving status in portion 262 of living tissue 260 (step 274).

Figure 2J:
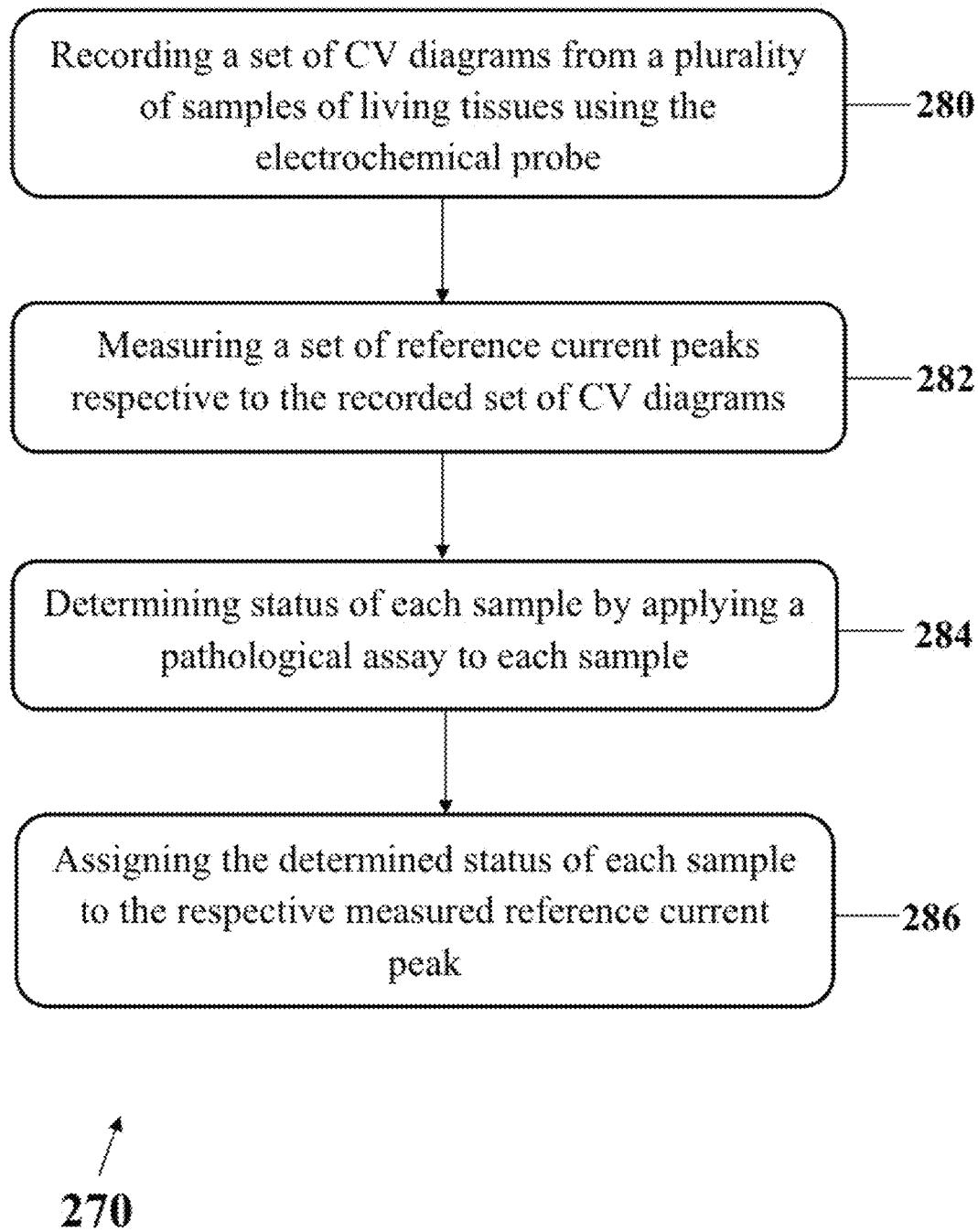
FIG. 2J shows an exemplary implementation of generating a set of reference current peak values, consistent with one or more exemplary embodiments of the present disclosure.

In detail, step 270 may include generating a set of reference current peak values. FIG. 2J shows an exemplary implementation of generating the set of reference current peak values (step 270), consistent with one or more exemplary embodiments of the present disclosure. In an exemplary implementation, generating the set of reference current peak values (step 270) may include recording a set of CV diagrams from a plurality of samples of living tissues using the electrochemical probe (i.e., CDP 102)(step 280), measuring a set of reference current peaks respective to the recorded set of CV diagrams for each sample of the plurality of samples of living tissues (step 282), determining status of each sample by applying a pathological assay to each sample (step 284), and assigning the determined status of each sample to the respective measured reference current peak (step 286). In an exemplary implementation, generating the set of reference current peak values (step 270) may include calibrating exemplary CDP 102 for an exemplary living tissue similar to living tissue 260. In such implementation, the plurality of samples of living tissues may include a plurality of samples of living tissues from the same organ, for example, breast tissue, of a plurality of human or animal bodies.

The determined status may include one of a healthy state, a cancerous state, and a moderately cancer-involved state, based on result of the applied pathological assay. In an exemplary implementation, detecting the cancer-involving status in portion 262 of living tissue 260 (step 274) may include detecting the healthy state for portion 262 of living tissue 260 responsive to the oxidation current peak being in a first range of the generated set of reference current peak values assigned as being of the healthy state, detecting the cancerous state for portion 262 of living tissue 260 responsive to the oxidation current peak being in a second range of the generated set of reference current peak values assigned as being of the cancerous state, and detecting the moderately cancer-involved state for portion 262 of living tissue 260 responsive to the oxidation current peak being in a third range of the generated set of reference current peak values assigned as being of the moderately cancer-involved state.

In an exemplary implementation, the whole process of exemplary method 200 which may include, putting the array of VAMWCNTs of exemplary sensor 102 in contact with the suspicious sample (step 202), recording the electrochemical response from the suspicious sample (step 204), and detecting the cancerous state in the suspicious sample (step 206) may be carried out in less than about 30 seconds. Similarly, in an exemplary implementation, steps 222-226 of exemplary method 220 which may include putting electrodes 15, 160, and 162 of exemplary CDP 102 in contact with exemplary portion 262 of living tissue 260 (step 222), recording the electrochemical response from exemplary portion 262 of living tissue 260 (FIG. 2C) (step 224), and detecting the cancerous state in 262 of living tissue 260 (step 226) may be carried out in less than about 30 seconds.

In an exemplary implementation, conducting cancer diagnosis process of exemplary method 220 which may further include replacing a previously used sensing part 154 with a new sensing part 154 may take place in less than about 40 seconds. In an exemplary implementation, conducting cancer diagnosis process of exemplary method 220 which may include replacing a previously used sensing part 154 with a new sensing part 154, inserting exemplary CDP 102 including the new sensing part 154 into a target tissue by inserting new sensing part 154 into a target location within the target tissue, recording a CV response with a current peak from the target location, and detecting cancerous state of the target tissue may take place in less than about 40 seconds. For example, replacing a previously used sensing part 154 with a new sensing part 154, inserting exemplary CDP 102 including the new sensing part 154 into portion 262 of living tissue 260 by inserting new sensing part 154 into portion 262 of living tissue 260, recording a CV response with a current peak from portion 262 of living tissue 260, and detecting cancerous state of portion 262 of living tissue 260 may take place in less than about 40 seconds.

In an exemplary implementation, replacing the previously used sensing part 154 may include removing the previously used sensing part 154, and connecting the new (fresh) sensing part 154 to handle 152. In an exemplary implementation, replacing the previously used sensing part 154 may take a time interval of less than about 20 sec. In an exemplary implementation, recording the CV response with the current peak from a target location (i.e., portion 262 of living tissue 260) may be carried out in about IS sec or less due to synchronized real-time processing.

Accordingly, in an exemplary embodiment, methods 200, and 220, provide a quick and efficient approach to instantaneously detect a tissue's cancerous state, including indicating presence of cancer. For example, exemplary CDP 102 may be utilized through exemplary methods 200, and 220 for real-time high-accurate detecting cancer-involved margins in a patient's body. In such implementations, exemplary methods 200, and 220 may be applied on at least one exemplary portion of a living tissue that may be suspicious to contain a cancerous tumor. In one implementation, exemplary methods 200, and 226 may be applied before a tumor removal surgery, during a tumor removal surgery, after a tumor removal surgery, and combinations thereof. In an exemplary implementation, exemplary CDP 102 may be utilized through exemplary methods 200, and 220 at suspicious margins around a dissected tumor after the tumor removal surgery to determine whether the suspicious margins are cancerous or not.

Figure 3A:
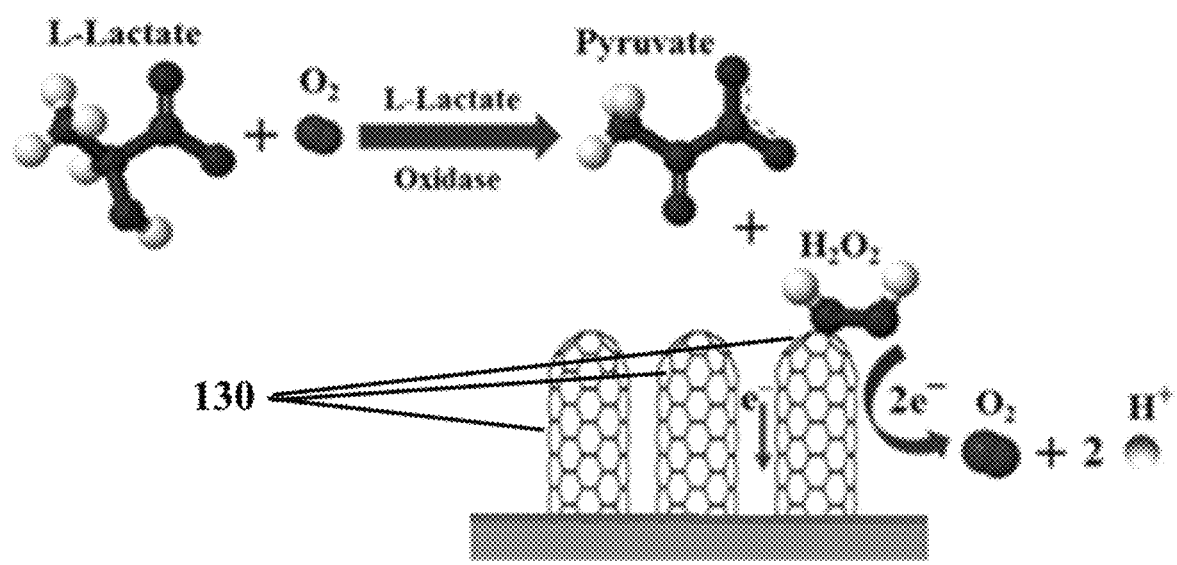
FIG. 3A illustrates a schematic view of exemplary electrochemical reactions involved on sensor including exemplary VAMWCNTs as shown in FIGS. 1D and 1G, consistent with one or more exemplary embodiments of the present disclosure.

In an exemplary implementation, electrochemical system 100 may be utilized for cancer diagnosis via exemplary method 200. FIG. 3A shows a schematic view of exemplary electrochemical reactions involved on sensor 102 including exemplary VAMWCNTs 130 as shown in FIGS. 1D and 1G, consistent with one or more exemplary embodiments of the present disclosure. Presence of $H_2O_2$ active molecule released during hypoxia glycolysis in a suspicious sample may be the main trigger of the electrochemical reactions. Hence, the chemical reaction occurring on the working electrode 108 including VAMWCNTs 130 may include:

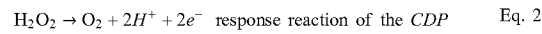

$$\text{L-Lactate} + O_2 \xrightarrow{\text{L-Lactate Oxidase}} \text{Pyruvate} + H_2O_2 \qquad \text{Eq. 1}$$

$$H_2O_2 \rightarrow O_2 + 2H^+ + 2e^- \text{ response reaction of the } CDP \qquad \text{Eq. 2}$$

When the hypoxia glycolysis (Eq. 2) is activated (the concentration of $O_2$ is least in 5%) in cancer cells, increased reactive oxygen species (ROS) generated by mitochondria, would significantly enhance the cathodic peak of an electrochemical response measured from the suspicious sample which could be sharply detected by VAMWCNTs 130 electrodes. It may be known that the lactate released by hypoxic tumor cells during their glycolysis may not be discharged as a waste product, but may be taken up by oxygenated tumor cells as energy fuel in which Lactate is converted to pyruvate and $H_2O_2$ by LDH-B and then enters the mitochondria for OXPHOS to generate ATP. Similar to this process, the lactate released from hypoxic tumor cells may be used herein in electrochemical assay to trace the concentration of lactate due to the intensity of the $H_2$ produced during LADH (Eq. 1) and released electrons due to the intensity of $H_2O_2$ oxidation reaction (Eq. 2).

Figure 3B:
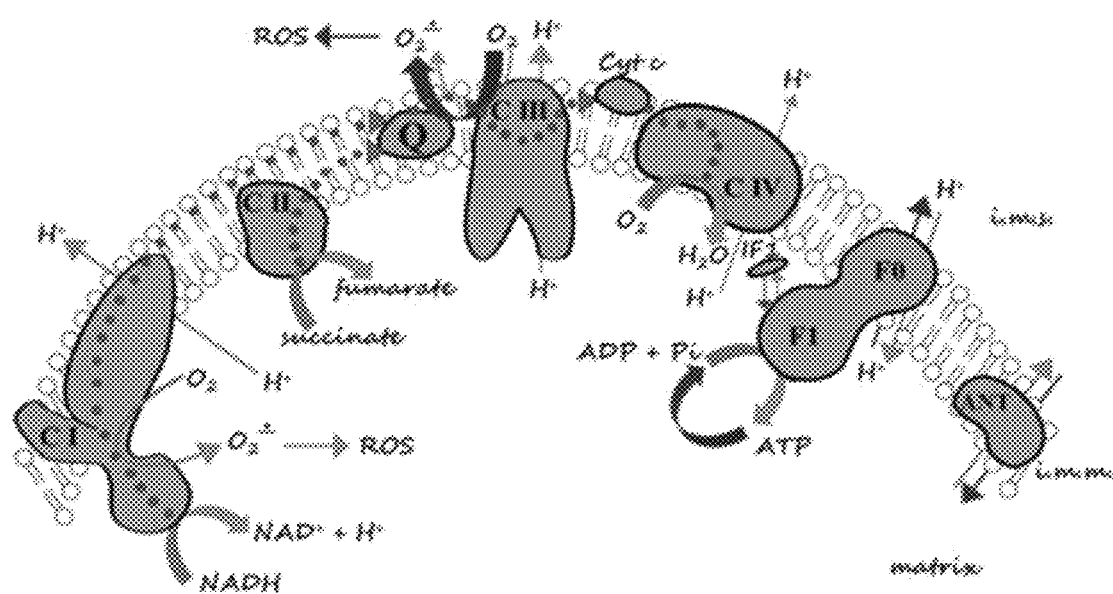
FIG. 3B illustrates a schematic overview of mitochondrial electron and proton fluxes in hypoxia, consistent with one or more exemplary embodiments of the present disclosure.

FIG. 3B shows a schematic overview of mitochondrial electron and proton fluxes in hypoxia, consistent with one or more exemplary embodiments of the present disclosure. During normaxia, electrons released from reduced cofactors (NADH and FADH2), flow through the redox centers of the respiratory chain (r.c.) to molecular oxygen (dotted lines), to which a proton flux from the mitochondrial matrix to the intermembrane space is coupled (grey arrows). Protons then flow back to the matrix through the F0 sector of the ATP synthase complex, driving ATP synthesis. ATP is carried to the cell cytosol by the adenine nucleotide translocator (grey arrows). Under moderate to severe hypoxia, electrons escape the r.c. redox centers and reduce molecular oxygen to the superoxide anion radical before reaching the cytochrome c (black arrows). Under these conditions, to maintain an appropriate $\Delta\psi m$, ATP produced by cytosolic glycolysis enters the mitochondria where it is hydrolyzed by the F1F0 ATPase with extrusion of protons from the mitochondrial matrix (black arrows). So, the mechanism of $H_2O_2$ detection by the VAMWCNTs 130 electrodes in hypoxia glycolysis may be based on released ion species during reduction of $NADH^+$, generation of ROS and production of superoxide anion radical by reducing molecular oxygen before reaching to cytochrome c. The amount of released charged species and increased current transferred by VAMWCNTs 130 electrodes may be correlated with the concentration of the lactate and subsequently $H_2O_2$ which resulted in ROS generated during hypoxia glycolysis.

Figure 1N:
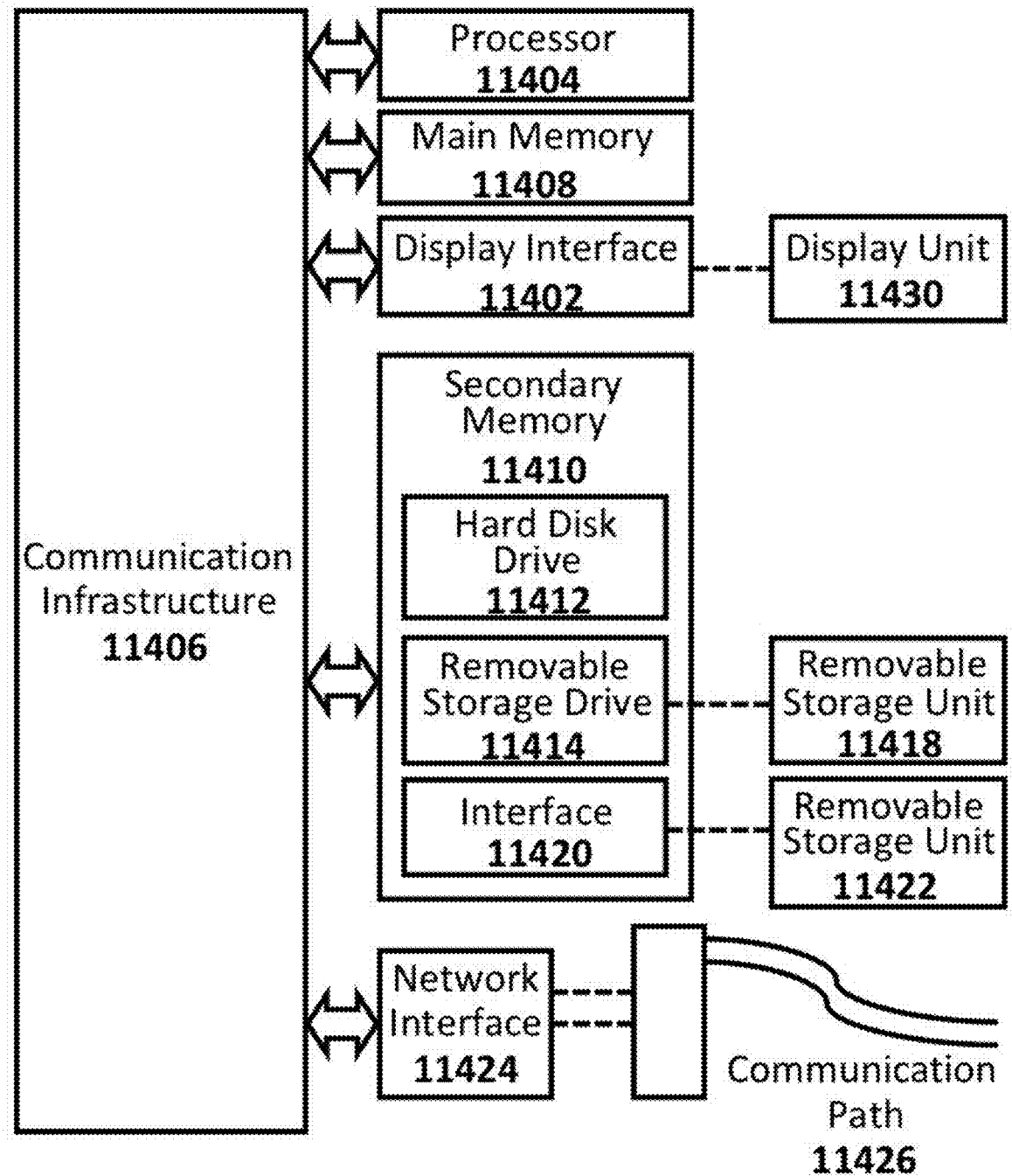
FIG. 1N shows a computer system in which an embodiment of the present disclosure, or portions thereof, may be implemented as computer-readable code, consistent with exemplary embodiments of the present disclosure.

FIG. 1N shows a computer system 114A in which an embodiment of the present disclosure, or portions thereof, may be implemented as computer-readable code, consistent with exemplary embodiments of the present disclosure. For example, steps 204-212 of flowchart 200, steps 224 and 226 of flowchart 220, steps 270-274 of flowchart 226, and steps 280-286 of flowchart 270 may be implemented in computer system 114A using hardware, software, firmware, tangible computer readable media having instructions stored thereon, or a combination thereof and may be implemented in one or more computer systems or other processing systems. Hardware, software, or any combination of such may embody any of the modules and components in FIGS. 1A-1M. In an exemplary embodiment, computer system 114A may include processor 114.

If programmable logic is used, such logic may execute on a commercially available processing platform or a special purpose device. One ordinary skill in the art may appreciate that an embodiment of the disclosed subject matter can be practiced with various computer system configurations, including multi-core multiprocessor systems, minicomputers, mainframe computers, computers linked or clustered with distributed functions, as well as pervasive or miniature computers that may be embedded into virtually any device.

For instance, a computing device having at least one processor device and a memory may be used to implement the above-described embodiments. A processor device may be a single processor, a plurality of processors, or combinations thereof. Processor devices may have one or more processor "cores."

An embodiment of the invention is described in terms of this example computer system 500. After reading this description, it will become apparent to a person skilled in the relevant art how to implement the invention using other computer systems and/or computer architectures. Although operations may be described as a sequential process, some of the operations may in fact be performed in parallel, concurrently, and/or in a distributed environment, and with program code stored locally or remotely for access by single or multi-processor machines. In addition, in some embodiments the order of operations may be rearranged without departing from the spirit of the disclosed subject matter.

Processor device 11404 may be a special purpose or a general-purpose processor device. As will be appreciated by persons skilled in the relevant art, processor device 11404 may also be a single processor in a multi-core/multiprocessor system, such system operating alone, or in a cluster of computing devices operating in a cluster or server farm. Processor device 11404 may be connected to a communication infrastructure 11406, for example, a bus, message queue, network, or multi-core message-passing scheme.

In an exemplary embodiment, computer system 114A may include a display interface 11402, for example a video connector, to transfer data to a display unit 11430, for example, a monitor. Computer system 114A may also include a main memory 11408, for example, random access memory (RAM), and may also include a secondary memory 11410. Secondary memory 11410 may include, for example, a hard disk drive 11412, and a removable storage drive 11414. Removable storage drive 11414 may include a floppy disk drive, a magnetic tape drive, an optical disk drive, a flash memory, or the like. Removable storage drive 11414 may read from and/or write to a removable storage unit 1141 in a well-known manner. Removable storage unit 11418 may include a floppy disk, a magnetic tape, an optical disk, etc., which may be read by and written to by removable storage drive 11414. As will be appreciated by persons skilled in the relevant art, removable storage unit 11418 may include a computer usable storage medium having stored therein computer software and/or data.

In alternative implementations, secondary memory 11410 may include other similar means for allowing computer programs or other instructions to be loaded into computer system 114A. Such means may include, for example, a removable storage unit 11422 and an interface 11420. Examples of such means may include a program cartridge and cartridge interface (such as that found in video game devices), a removable memory chip (such as an EPROM, or PROM) and associated socket, and other removable storage units 11422 and interfaces 11420 which allow software and data to be transferred from removable storage unit 11422 to computer system 114A.

Computer system 114A may also include a communications interface 11424. Communications interface 524 allows software and data to be transferred between computer system 114A and external devices. Communications interface 11424 may include a modem, a network interface (such as an Ethernet card), a communications port, a PCMCIA slot and card, or the like. Software and data transferred via communications interface 11424 may be in the form of signals, which may be electronic, electromagnetic, optical, or other signals capable of being received by communications interface 11424. These signals may be provided to communications interface 11424 via a communications path 11426. Communications path 11426 carries signals and may be implemented using wire or cable, fiber optics, a phone line, a cellular phone link, an RF link or other communications channels.

In this document, the terms "computer program medium" and "computer usable medium" are used to generally refer to media such as removable storage unit 11418, removable storage unit 11422, and a hard disk installed in hard disk drive 11412. Computer program medium and computer usable medium may also refer to memories, such as main memory 11408 and secondary memory 11410, which may be memory semiconductors (e.g. DRAMs, etc.).

Computer programs (also called computer control logic) are stored in main memory 1140 and/or secondary memory 11410. Computer programs may also be received via communications interface 11424. Such computer programs, when executed, enable computer system 114A to implement different embodiments of the present disclosure as discussed herein. In particular, the computer programs, when executed, enable processor device 11404 to implement the processes of the present disclosure, such as the operations in method 200 illustrated by flowchart 204 of FIGS. 2A and 2D, flowchart 220 of FIG. 2E, flowchart 226 of FIG. 2I, and flowchart 270 of FIG. 2J discussed above. Accordingly, such computer programs represent controllers of computer system 114A. Where an exemplary embodiment of method 200 is implemented using software, the software may be stored in a computer program product and loaded into computer system 114A using removable storage drive 11414, interface 11420, and hard disk drive 11412, or communications interface 11424.

Embodiments of the present disclosure also may be directed to computer program products including software stored on any computer useable medium. Such software, when executed in one or more data processing device, causes a data processing device to operate as described herein. An embodiment of the present disclosure may employ any computer useable or readable medium. Examples of computer useable mediums include, but are not limited to, primary storage devices (e.g., any type of random access memory), secondary storage devices (e.g., hard drives, floppy disks, CD ROMS, ZIP disks, tapes, magnetic storage devices, and optical storage devices, MEMS, nanotechnological storage device, etc.).

The embodiments have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

Example 1: Fabrication of CNT Based Electrochemical Chip for In Vitro Assays

In this example, exemplary CNT based electrochemical chips was fabricated for in vitro assays. First, silicon wafer (p-type <100>) substrates were cleaned through standard RCA #1 method ($NH_4OH:H_2O_2:H_2O$ solution and volume ratio of 1:1:5 respectively). Then, the cleaned substrates were rinsed in deionized (DI) water and dried by air. A thin layer of $SiO_2$ with a thickness of about 200 nm was grown by wet oxidation furnace on the surface of the silicon wafer, as a passivation layer. Nickel (Ni) catalyst layer for CNT growth with a thickness of about 9 nm was coated on $SiO_2$ by E-beam evaporation system at a temperature of about 120° C. with depositing rate of about 0.1 Angstroms/s. Afterwards, Ni-covered samples were located in a direct current plasma enhanced chemical vapor deposition (DC-PECVD) system to grow vertically aligned multi-walled carbon nanotubes (VAMWCNT). The growth process has three steps, including annealing, graining and growth. At first, the sample was annealed at a temperature of about 680° C. in an $H_2$ environment with a flow rate of about 35 standard cubic centimeters per minute (sccm) for about 30 minutes. During the graining, the surface was plasma hydrogenated for about 5 minutes with the intensity of about 5.5 $W \cdot cm^{-2}$ which results in the catalyst graining and formation of Ni nano-sized islands. In the growth step a plasma of $C_2H_2$ and $H_2$ mixture with flow rates of about 5 sccm and about 35 sccm were introduced to the chamber for about 15 minutes. Finally, CNT's were characterized with field emission scanning electron microscopy (FESEM). The length of CNTs ranged from about 2.5 to about 5 μm and the diameter of CNTs ranged from about 50 nm to about 70 nm.

Figure 4:
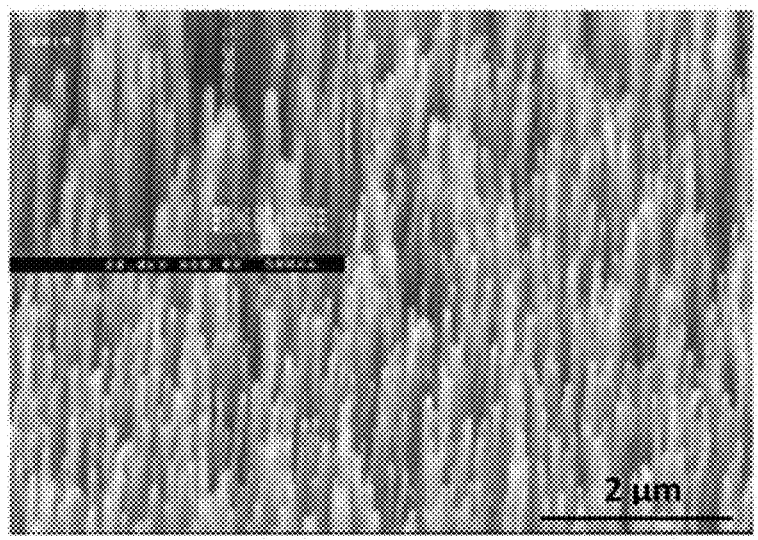
FIG. 4 illustrates afield emission scanning electron microscopy (FESEM) image of the VAMWCNTs array on a portion of an exemplary fabricated CNT based electrochemical chip, consistent with one or more exemplary embodiments of the present disclosure.

FIG. 4 shows the FESEM image of the VAMWCNTs array on a portion of an exemplary fabricated CNT based electrochemical chip, consistent with one or more exemplary embodiments of the present disclosure. The CNTs were multi-walled carbon nanotubes with high purity and a presence of nickel on the top side of the CNTs could be related to the tip-growth mechanism. The CNT has been used as the work, counter and reference electrodes in exemplary fabricated CNT based electrochemical chips. The active area of the work, counter and reference electrodes were about 100 mm², 100 mm², 50 mm², respectively. The CNT based electrochemical chips were connected to a potentiostat by conductive wires bonded to the pads of the potentiostat.

Example 2: Fabrication of Cancer Diagnostic Probe (CDP) for In Vivo Assays

In this example, the tips of sterile steel needles were coated by Ni catalyst layers similar to that was described in EXAMPLE 1 for CNT based electrochemical chips with the assistance of E-Beam coating system. A fixture was designed and fabricated to hold the needles both in E-Beam and DC-PECVD systems to limit the growth of CNTs just in the tips of the needles. Then, the CNT grown needles were attached to electrical connectors with three pins by a conductive paste. Just tips of the needle were extended from the connectors up to about 1 cm. The probe was reinforced with a homemade holder and connected to a readout system by a noiseless cable which handled all three electrodes.

Figure 5A:
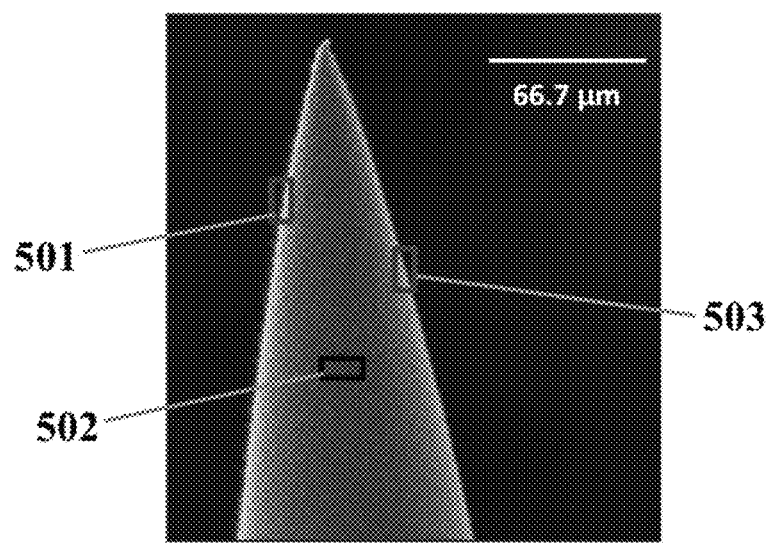
FIG. 5A illustrates a FESEM image of a tip of a needle electrode of an exemplary fabricated cancer diagnostic probe (CDP) coated with an array of VAMWCNTs on the tip, consistent with one or more exemplary embodiments of the present disclosure.
Figure 5B:
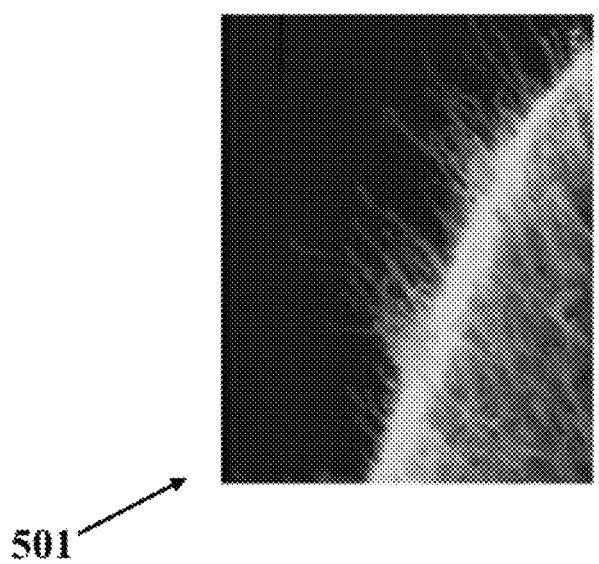
FIG. 5B illustrates a FESEM image of a first portion of an exemplary VAMWCNTs array grown on the tip of the needle electrode of exemplary fabricated CDP, consistent with one or more exemplary embodiments of the present disclosure.
Figure 5C:
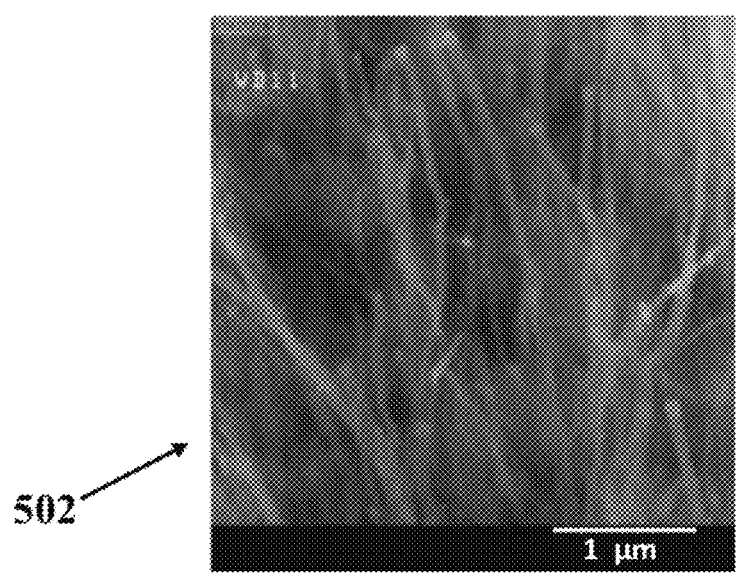
FIG. 5C illustrates a FESEM image of a second portion of an exemplary VAMWCNTs array grown on the tip of the needle electrode of exemplary fabricated CDP, consistent with one or more exemplary embodiments of the present disclosure.
Figure 5D:
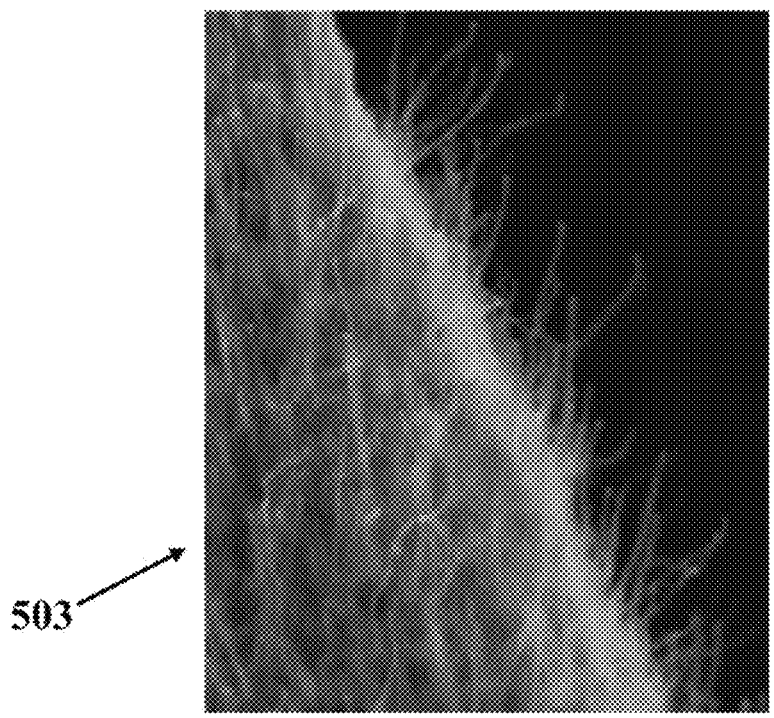
FIG. 5D illustrates a FESEM image of a third portion of an exemplary VAMWCNTs array grown on the tip of the needle electrode of exemplary fabricated CDP, consistent with one or more exemplary embodiments of the present disclosure.

FIGS. 5A-5D show FESEM images of a tip of a needle electrode of an exemplary fabricated cancer diagnostic probe (CDP) coated with an array of VAMWCNTs on the tip and exemplary portions 501, 502 and 503 of the tip, consistent with one or more exemplary embodiments of the present disclosure. FIG. 5A illustrates a FESEM image of the tip of a needle electrode of an exemplary fabricated cancer diagnostic probe (CDP) coated with the array of VAMWCNTs on the tip, consistent with one or more exemplary embodiments of the present disclosure. FIG. 5B illustrates a FESEM image of portion 501 of the tip, consistent with one or more exemplary embodiments of the present disclosure. FIG. 5C illustrates a FESEM image of portion 502 of the tip, consistent with one or more exemplary embodiments of the present disclosure. FIG. 5D illustrates a FESEM image of portion 503 of the tip, consistent with one or more exemplary embodiments of the present disclosure.

Example 3: CV of $H_2O_2$ Contained Lactate Solution

In this example, the cyclic voltammetry (CV) diagram of L-lactic acid solution individually were recorded by exemplary electrochemical sensors including working electrodes (WEs) fabricated from platinum (Pt). Gold (Au), amorphous glassy carbon (GC) and carbon nanotube (CNT).

Figure 6A:
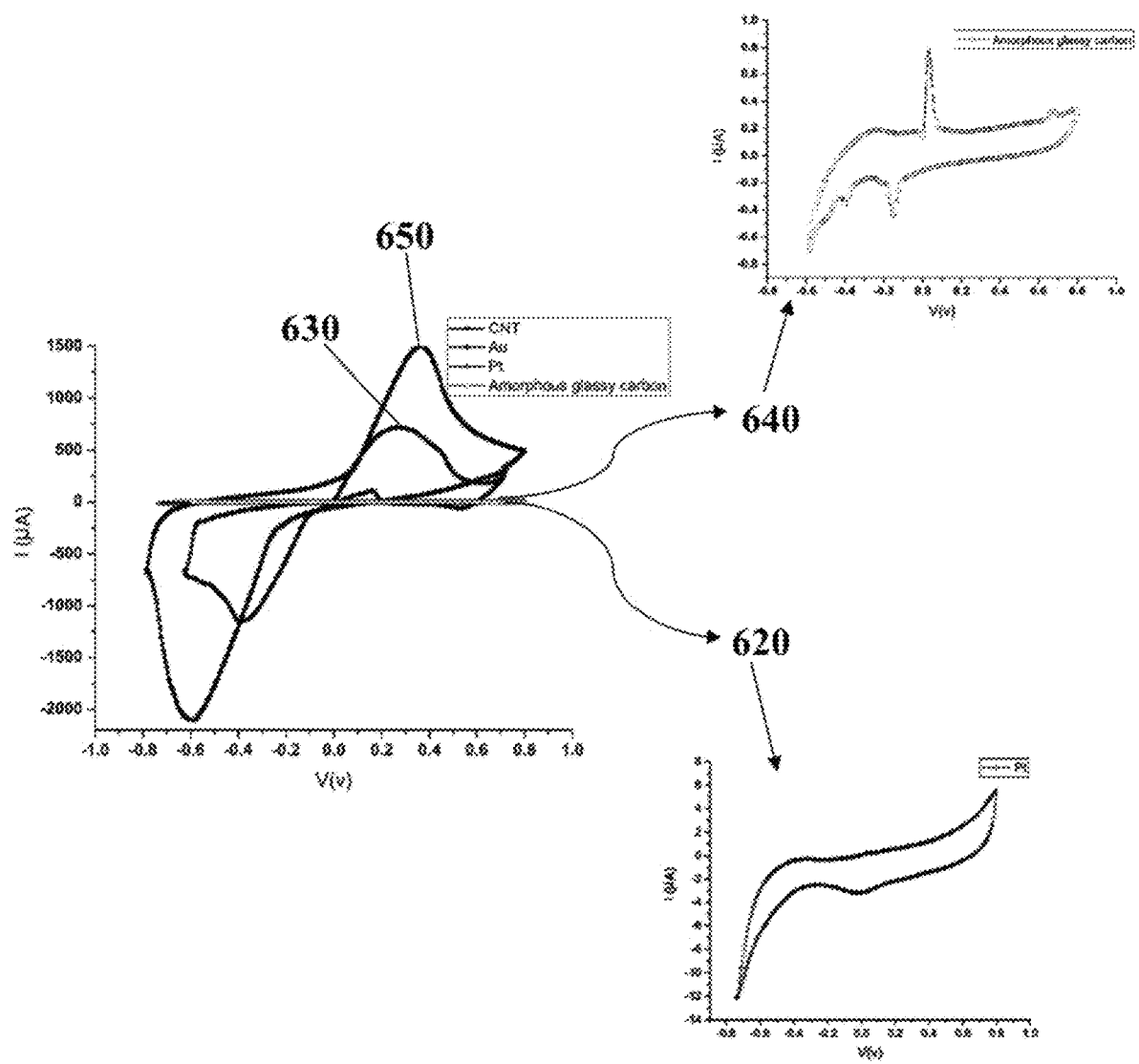
FIG. 6A illustrates the CV diagrams of L-lactic acid solution individually recorded by electrochemical sensors fabricated from platinum (Pt), Gold (Au), amorphous glassy carbon (GC) and carbon nanotube (CNT) working electrodes (WEs), consistent with one or more exemplary embodiments of the present disclosure.

FIG. 6A shows the CV diagrams of L-lactic acid solution individually recorded by electrochemical sensors fabricated from platinum (Pt) (curve 620), Gold (Au) (curve 630), amorphous glassy carbon (GC) (curve 640), and carbon nanotube (CNT) working electrodes (WEs) (curve 650), consistent with one or more exemplary embodiments of the present disclosure. It may be observed that the detected cathodic peak by CNT WE was so sharper (about 1500 μA) in similar concentration of $H_2O_2$ with respect to other electrodes (about 717, 5.7 and 0.8 μA in Au, Pt and GC electrodes, respectively). CNT greatly transfer the released charges from oxidized $H_2O_2$ beneath the nanotubes in media solution. Hence, CNT arrays were used as electrodes of exemplary sensors in the present disclosure.

Figure 6B:
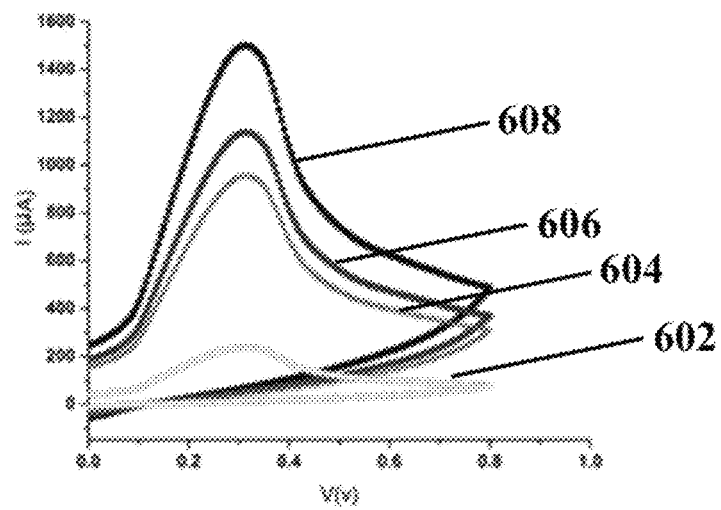
FIG. 6B illustrates the CV diagrams of solutions with various concentrations of Hydrogen Peroxide ($H_2O_2$) resulted from the lactate turn to $H_2O_2$ and pyruvate recorded by electrochemical sensors with CNT arrays working electrode, consistent with one or more exemplary embodiments of the present disclosure.

FIG. 6B shows the CV diagrams of solutions with various concentrations of lactate (and subsequently $H_2O_2$) recorded by electrochemical sensors with CNT arrays working electrode, consistent with one or more exemplary embodiments of the present disclosure. CV diagrams were recorded for solutions with a lactate concentration of about 0.025 mM (CV diagram 602), 0.05 mM (CV diagram 604), 0.1 mM (CV diagram 606), and 0.3 mM (CV diagram 608). CNT working electrode presented a well concentration depended increased response to the presence of lactate molecules in the solutions ranged from about 0.025 mM (CV diagram 602) to about 0.3 mM (diagram 608).

Figure 6C:
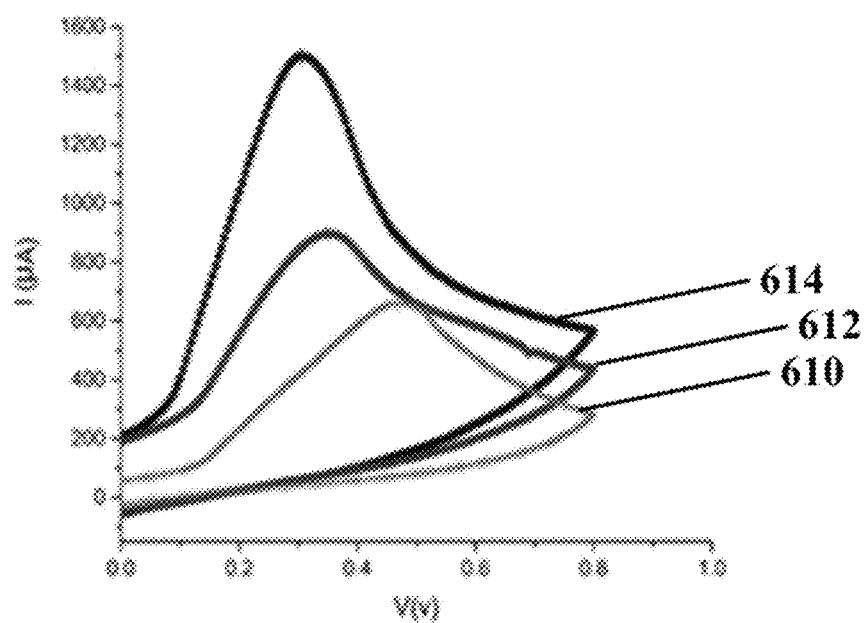
FIG. 6C illustrates the CV diagrams of $H_2O_2$ contained lactate solution in comparison with two cell culture solutions recorded by electrochemical sensors with CNT arrays working electrode, consistent with one or more exemplary embodiments of the present disclosure.

FIG. 6C shows the CV diagrams of $H_2O_2$ contained lactate solution with a lactate concentration of about 0.3 mM (CV diagram 614) in comparison with two cell culture solutions RPMI (CV diagram 610) and DMEN (CV diagram 612) recorded by electrochemical sensors with CNT arrays working electrode, consistent with one or more exemplary embodiments of the present disclosure. It may be observed that RPMI and DMEN cell culture solutions show less electrochemical responses in comparison with $H_2O_2$ contained lactate solution. The RPMI presented no electrochemical responses in the voltage attributed to the lactate detection. As a result, RPMI could be applied as cellular and tissue culture media with a negligible false positive response.

Example 4: Electrochemical Responses of Different Cell Lines

In this example, electrochemical sensing of $H_2O_2$ produced during Lactate/Pyruvate hypoxic glycolysis was verified in four different phenotypes of breast cell lines ranged from normal to malignant stages, including: MCF10 A, MCF-7, MDA-MB-231, and MDA-MB-468. Breast cancer cell lines (MCF10A, MCF-7, MDA-MB-231, MDA-MB-468) were obtained and were maintained at 37° C. (5% $CO_2$, 95% air) in RPMI medium supplemented with 5% fetal bovine serum, and 1% penicillin/streptomycin. The fresh medium was replaced every other day. All cell lines were tested and found negative for Mycoplasma contamination. The cells were detached from the plates by trypsin and counted by neobar laam.

Figure 7:
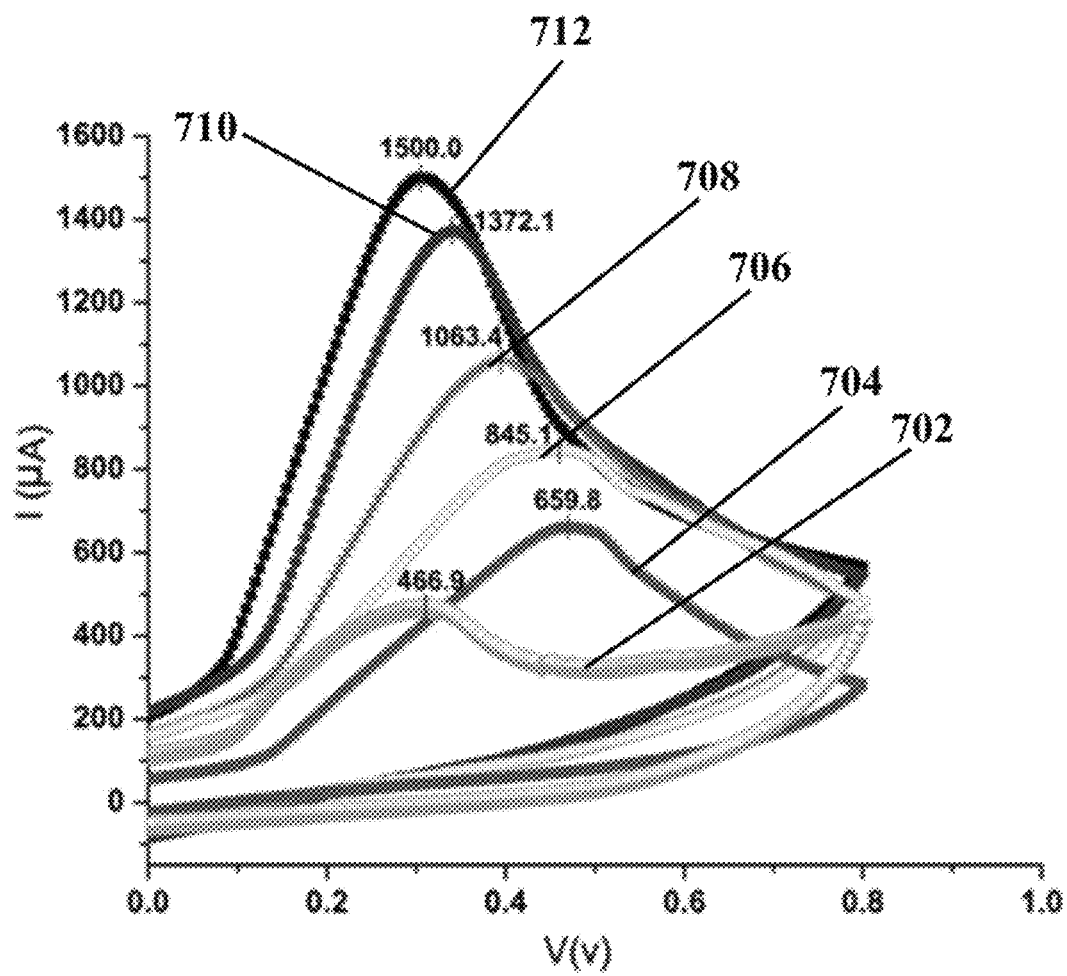
FIG. 7 illustrates the CV diagrams of hypoxic glycolysis in MCF 10A, MCF-7, MDA-MB-231, and MDA-MB-468 cell lines in comparison with $H_2O_2$ contained lactate solution and RPMI measured and recorded by exemplary CNT based electrochemical chip, consistent with one or more exemplary embodiments of the present disclosure.

FIG. 7 shows the CV responses of normal (MCF10A: CV diagram 702) and different grades of cancerous (MCF7: CV diagram 706, MDA-MB231: CV diagram 708, and MDA-B468: CV diagram 710) breast cells' solution media cultured for about 48 hours in comparison with standard $H_2O_2$ contained lactate solution with a lactate concentration of about 0.3 mM (CV diagram 712) and RPMI (CV diagram 704) in individual sensing wells of exemplary fabricated sensor in EXAMPLE 1 herein above, consistent with one or more exemplary embodiments of the present disclosure. Lactate production due to hypoxic glycolysis would be well detectable after about 48 hours of incubation in cancer cell lines. The CV diagrams of FIG. 7 show that the intensity of oxidation peak, located at the position of $H_2O_2$ electrochemical response, significantly increased with the progression in invasive grades of cancer cells in which hypoxia glycolysis would be enhanced.

Referring to FIG. 6B and FIG. 7, sharp difference in electrochemical peaks of $H_2O_2$ contained lactate solution was observed from about 0.025 mM to about 0.05 mM which could be applied to calibrate cancer cells' media from normal ones. Because the electrochemical responses of cancer cells' media solution was equal to the response range of $H_2O_2$ contained lactate solution with the concentration of more than about 0.05 mM meanwhile such response in normal cells was equal to the response range of the $H_2O_2$ contained lactate solution with the concentration of less than about 0.025 mM.

Moreover, similar responses were recorded from the culture media of colon, prostate, liver, lung, mouth, neural and hematopoietic cell lines in normal and cancer phenotypes with invasive and moderate grades by electrochemical sensing of $H_2O_2$ produced during Lactate/Pyruvate hypoxic glycolysis for some other types of colon, neural, prostate, liver, mouth, hematopoietic and lung cell lines. Colon (COR-L 105, SW-480, HT-29), Hematopoietic (1301, LCL-PI 1), Liver (HEP G2), Lung (QU-DB, MRC-S), Mouth (KB), Neuron (BE(2)-C, LAN-5), Prostate (PC-3, Du-145) cell lines were obtained and were maintained at 37° C. (5% $CO_2$, 95% air) in RPMI medium supplemented with 5% fetal bovine serum, and 1% penicillin/streptomycin. The fresh medium was replaced every other day. All cell lines were tested and found negative for Mycoplasma contamination. The cells were detached from the plates by trypsin and counted by neobar loam.

Figure 8A:
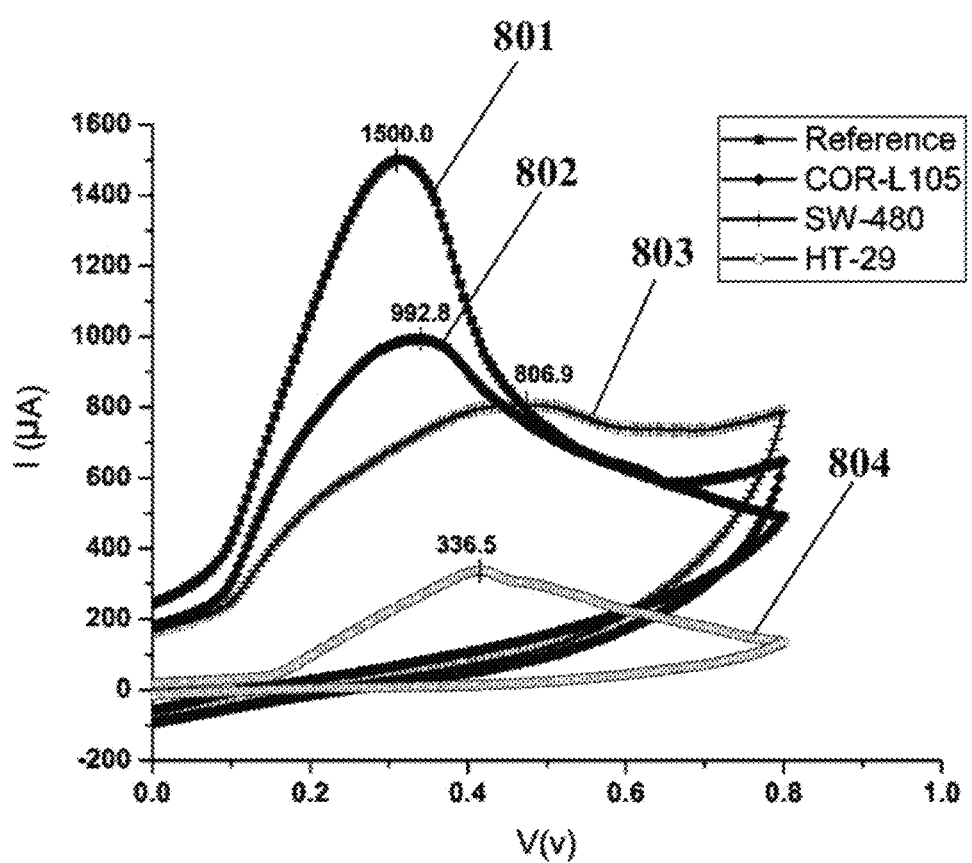
FIG. 8A illustrates the CV responses of the solution media of different normal and cancerous cell lines in various phenotypes for Colon (COR-L 105, SW-480, HT-29) cell lines in comparison with Reference diagram for solution $H_2O_2$ contained solution with a lactate concentration of about 0.3 mM, consistent with one or more exemplary embodiments of the present disclosure.
Figure 8B:
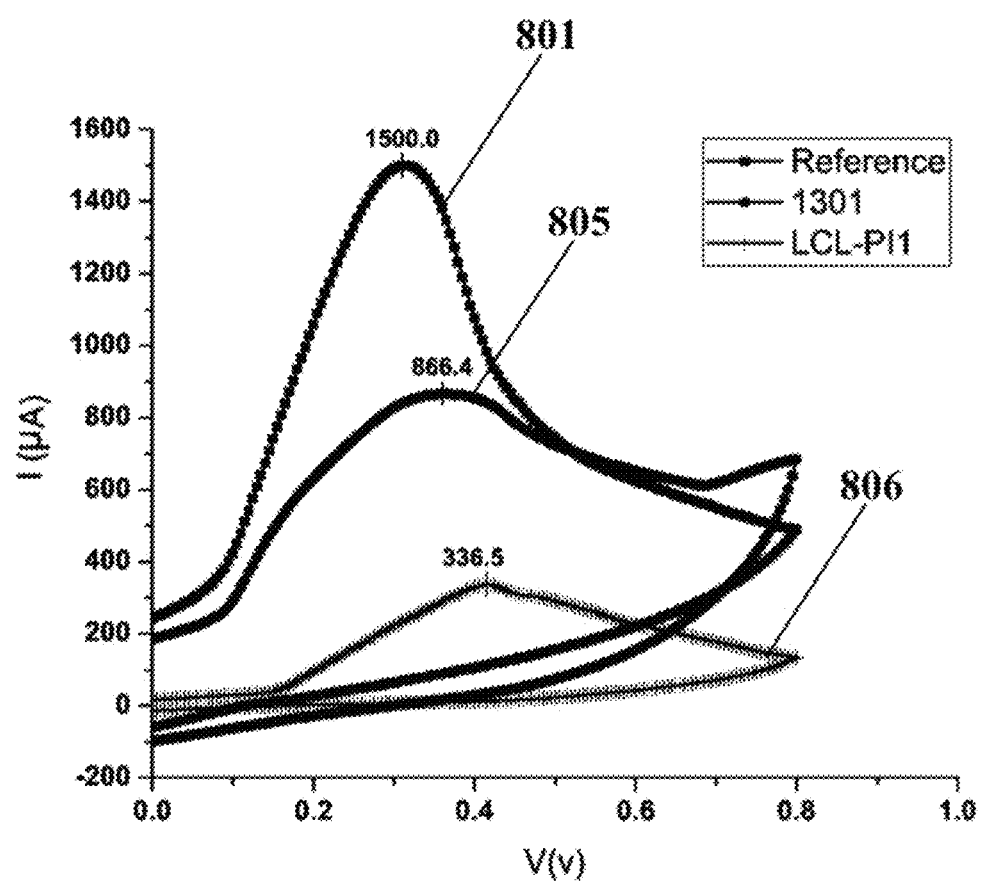
FIG. 8B illustrates the CV responses of the solution media of different normal and cancerous cell lines in various phenotypes for Hematopoietic (1301, LCL-PI 1) cell lines in comparison with Reference diagram for $H_2O_2$ contained solution with a lactate concentration of about 0.3 mM, consistent with one or more exemplary embodiments of the present disclosure.
Figure 8C:
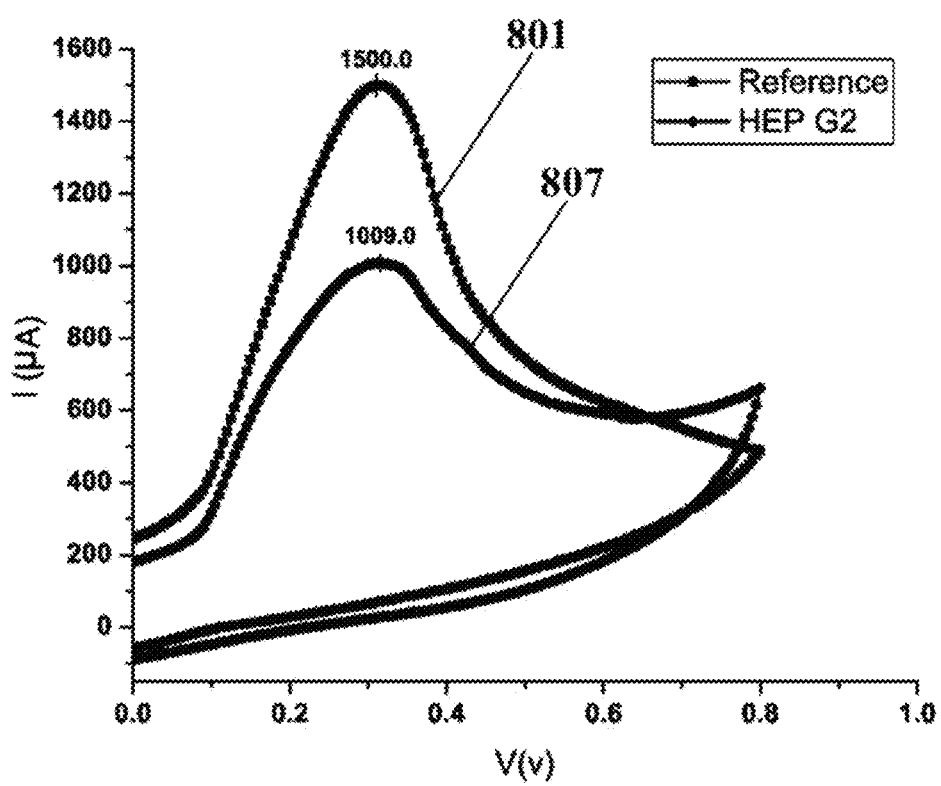
FIG. 8C illustrates the CV responses of the solution media of different normal and cancerous cell lines in various phenotypes for Liver (HEP G2) cell lines in comparison with Reference diagram for $H_2O_2$ contained lactate solution with a lactate concentration of about 0.3 mM, consistent with one or more exemplary embodiments of the present disclosure.
Figure 8D:
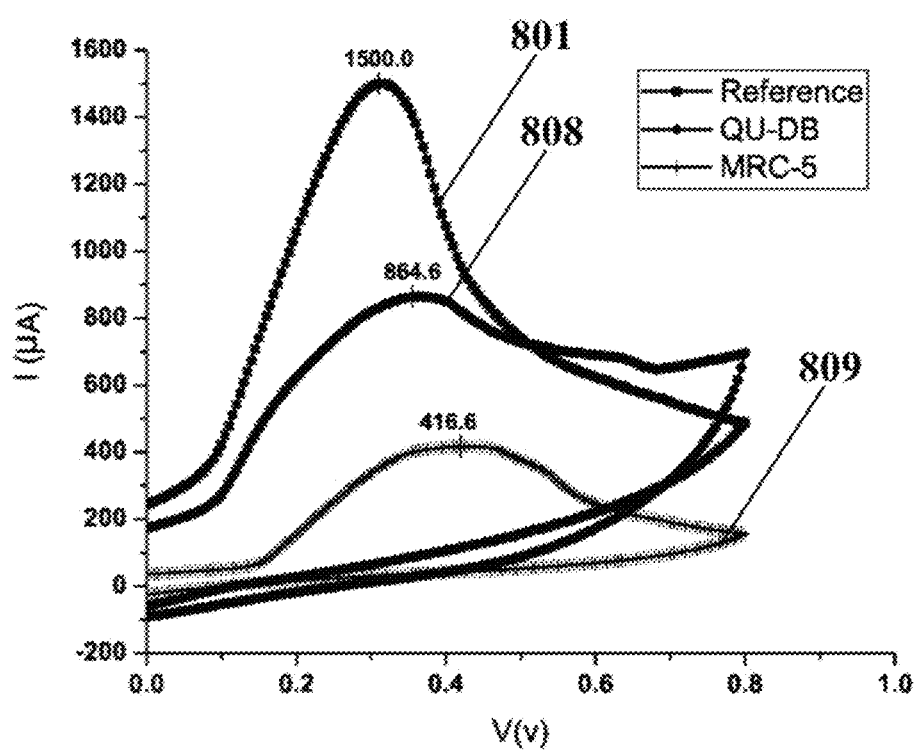
FIG. 8D illustrates the CV responses of the solution media of different normal and cancerous cell lines in various phenotypes for Lung (QU-DB, MRC-5) cell lines in comparison with Reference diagram for $H_2O_2$ contained lactate solution with a lactate concentration of about 0.3 mM, consistent with one or more exemplary embodiments of the present disclosure.
Figure 8E:
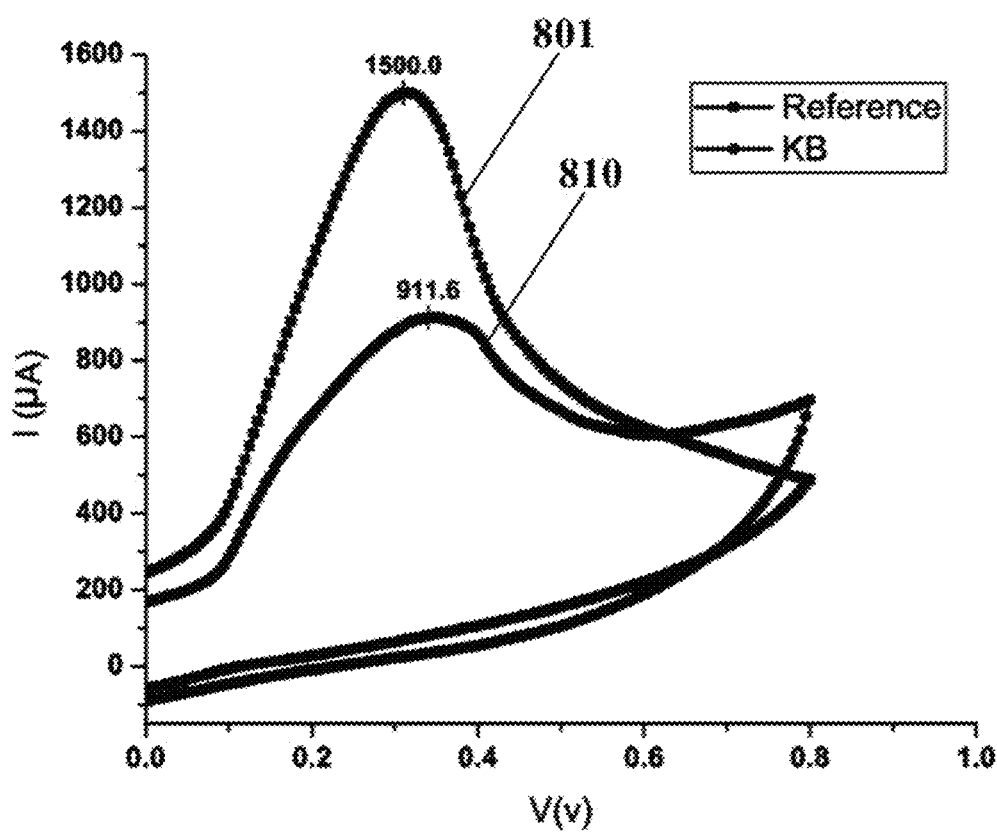
FIG. 8E illustrates the CV responses of the solution media of different normal and cancerous cell lines in various phenotypes for Mouth (KB) cell lines in comparison with Reference diagram for $H_2O_2$ contained lactate solution with a lactate concentration of about 0.3 mM, consistent with one or more exemplary embodiments of the present disclosure.
Figure 8F:
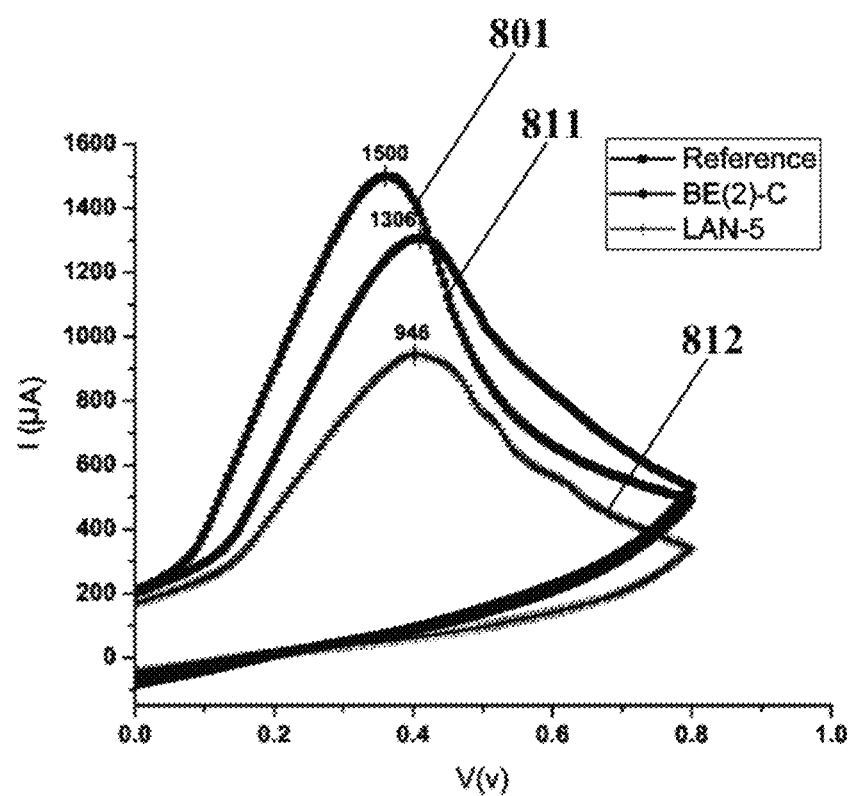
FIG. 8F illustrates the CV responses of the solution media of different normal and cancerous cell lines in various phenotypes for Neuron (BE(2)-C, LAN-5) cell lines in comparison with Reference diagram for $H_2O_2$ contained lactate solution with a lactate concentration of about 0.3 mM, consistent with one or more exemplary embodiments of the present disclosure.
Figure 8G:
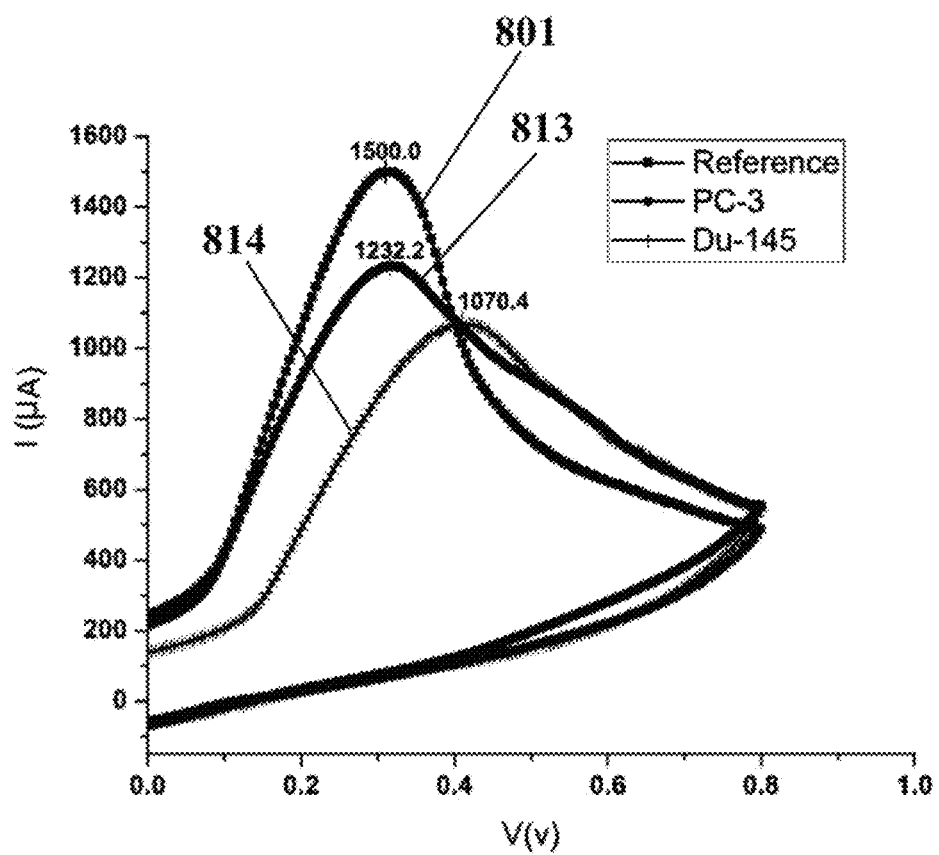
FIG. 8G illustrates the CV responses of the solution media of different normal and cancerous cell lines in various phenotypes for Prostate (PC-3, Du-145) cell lines in comparison with Reference diagram for $H_2O_2$ contained lactate solution with a lactate concentration of about 0.3 mM, consistent with one or more exemplary embodiments of the present disclosure.

FIGS. 8A-8G shows the CV responses of the solution media of different normal and cancerous cell lines in various phenotypes including Colon (COR-L 105 802, SW-480 803, HT-29804) in FIG. 8A, Hematopoietic (1301 805, LCL-PI 1 806) in FIG. 8B, Liver (HEP G2 807) in FIG. 8C, Lung (QU-DB 88, MRC-5 809) in FIG. 8D, Mouth (KB 810) in FIG. 8E, Neuron (BE(2)-C, LAN-5) in FIG. 8F, and Prostate (PC-3 813, Du-145 814) in FIG. 8G cell lines in comparison with Reference diagram 801 for $H_2O_2$ contained lactate solution with a lactate concentration of about 0.3 mM, consistent with one or more exemplary embodiments of the present disclosure. The current peaks in cancerous samples were observably increased. The $H_2O_2$ based oxidative peaks of cancer media solutions were sharper than that in normal cells. Grade dependent increase was observed in $H_2O_2$ peaks of cancer cells with sharp difference between normal and cancer phenotypes in all of the cell lines. This reveal the increased hypoxia glycolysis in cancer cells with respect to that in normal cells. A great correlation was observed between the cells' phenotypes and their lactate based $H_2O_2$ electrochemical responses.

Example 5: In Vitro Diagnosis of Cancer in Samples by Electrochemical Tracking of Hypoxia Glycolysis in Secretion of the Samples In this example, the electrochemical responses of 6 breast tissues removed by biopsy (core needle biopsy (CNB)) or surgery from 6 of suspicious patients to cancer were analyzed using exemplary CNT based electrochemical chip. The size of the removed samples was similar (with the non-dehydrated weight of about 25 mg). The electrochemical responses were compared with cytopathological analysis done by Hematoxylin and Eosin (H & E) staining of the 6 breast tissues. Each resected sample was maintained in RPMI for about 24 hours before analyzing by exemplary CNT based electrochemical chip to be ensured from the lactate release in hypoxic tumors. Before pathological assaying, each resected sample was fixed in Formaline. For electrochemical analysis of hypoxia glycolysis in secretion of the samples, live spices from CNB or surgically removed samples were cut in similar specimens and directly transferred through sensing wells of exemplary CNT based electrochemical chip containing RPMI-1640 without any preprocessing. About 24 hours after maintaining the samples in incubator, about 200 µl of the culture media was dropped to individual sensing wells and the cathodic current of electrochemical responses of $H_2O_2$ were recorded in CV profile.

Figure 9A:
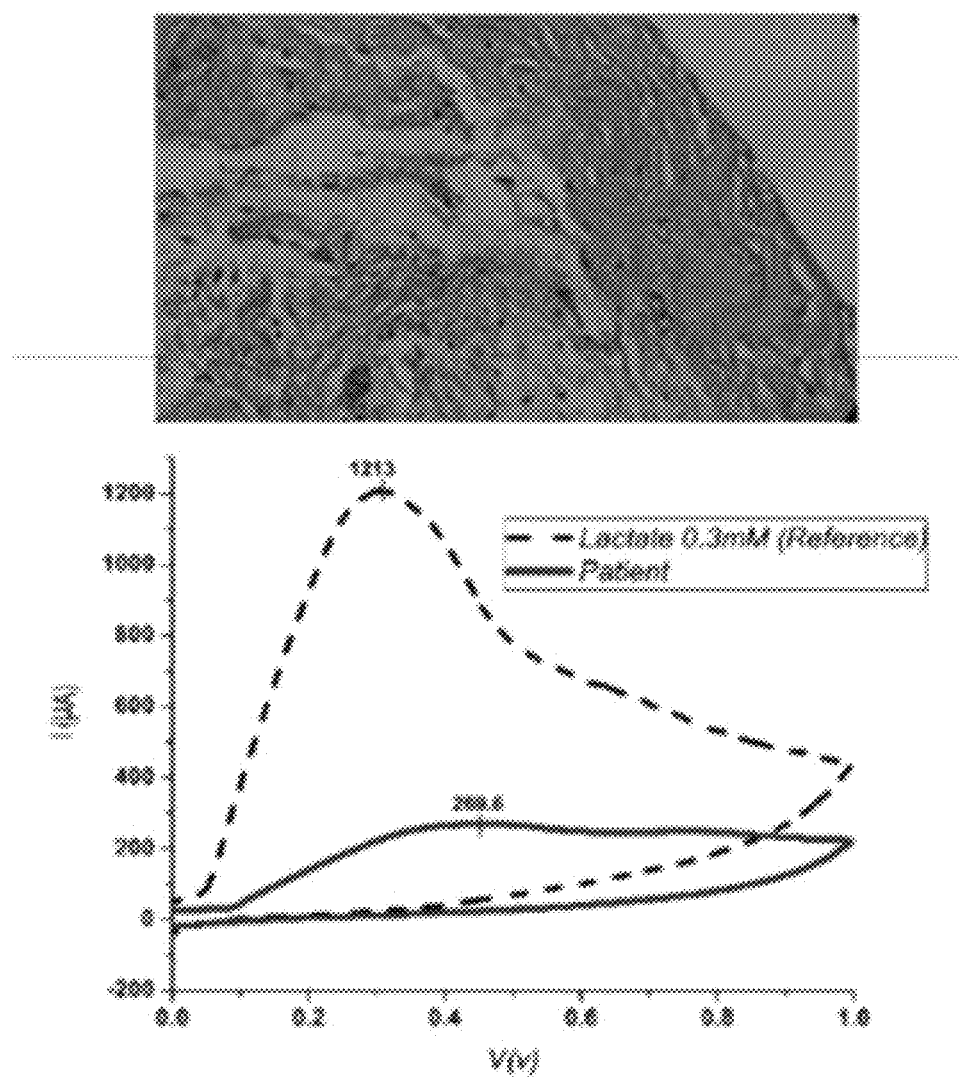
FIGS. 9A-9F illustrate the cytopathological results (top side) and electrochemical responses (bottom side) of the breast tissues removed by biopsy or surgery from 6 suspicious patients to cancer, consistent with one or more exemplary embodiments of the present disclosure.
Figure 9B:
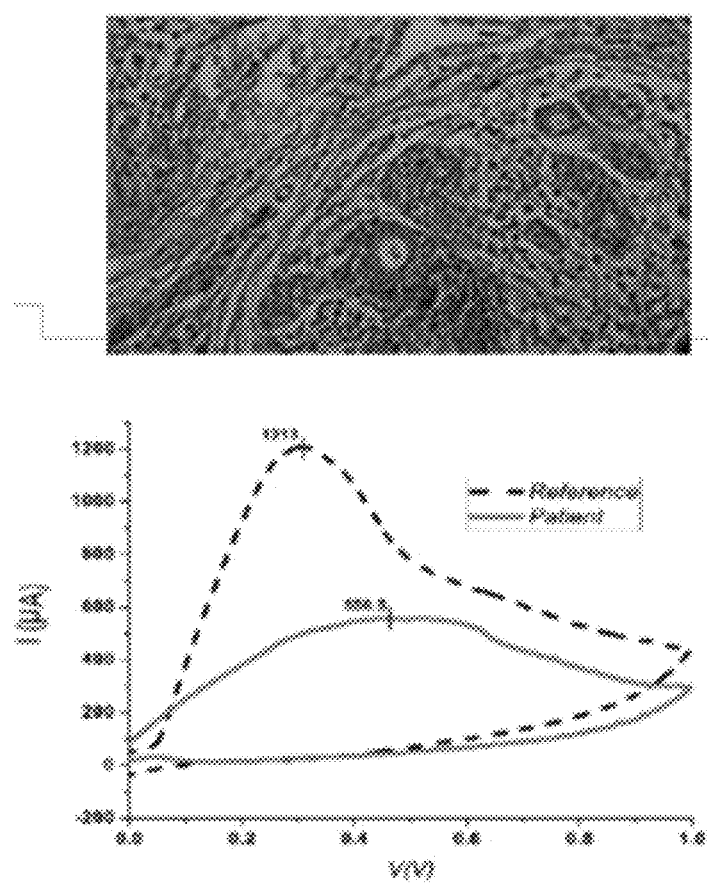
Figure 9C:
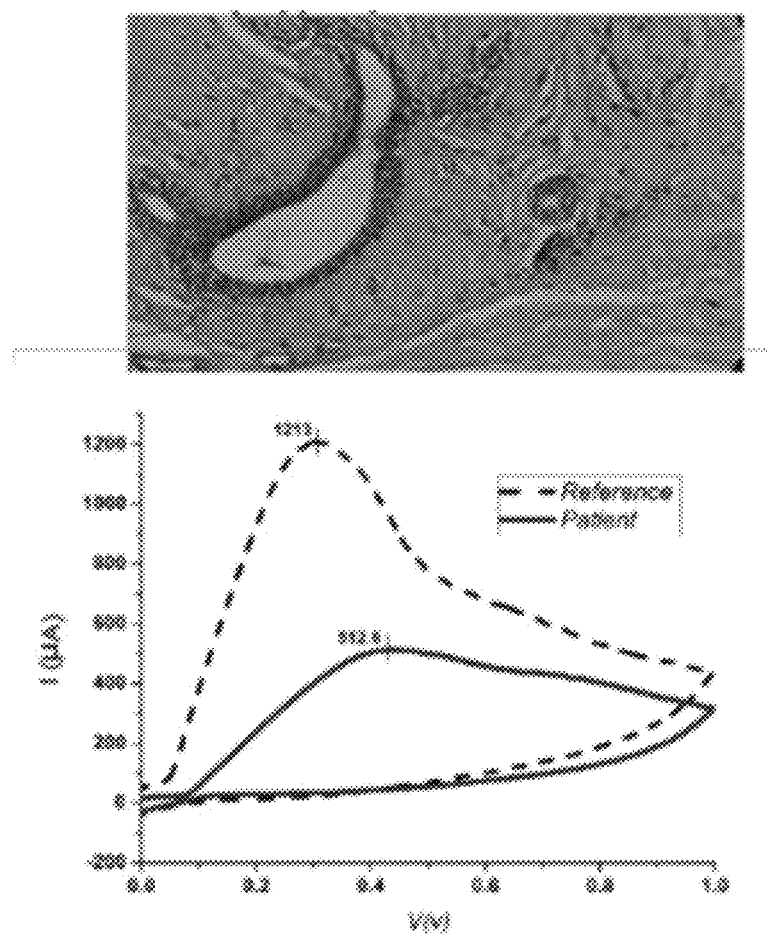
Figure 9D:
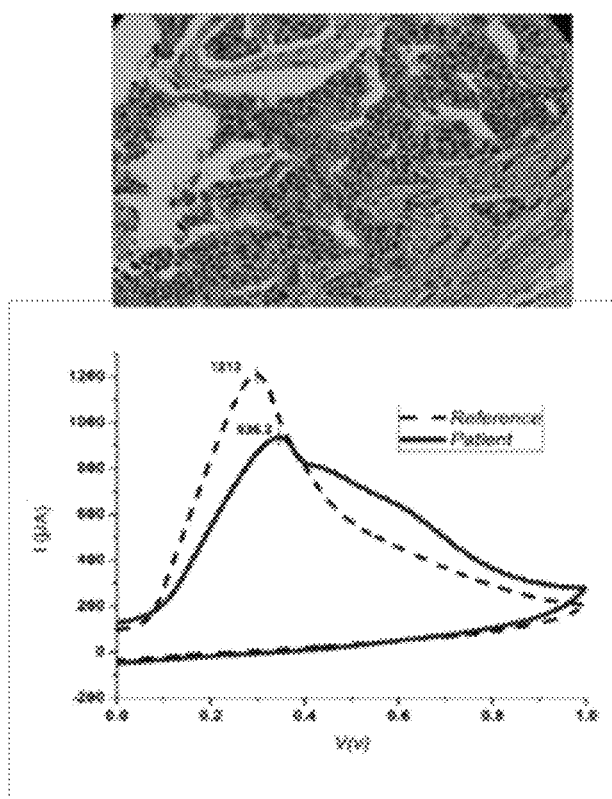
Figure 9E:
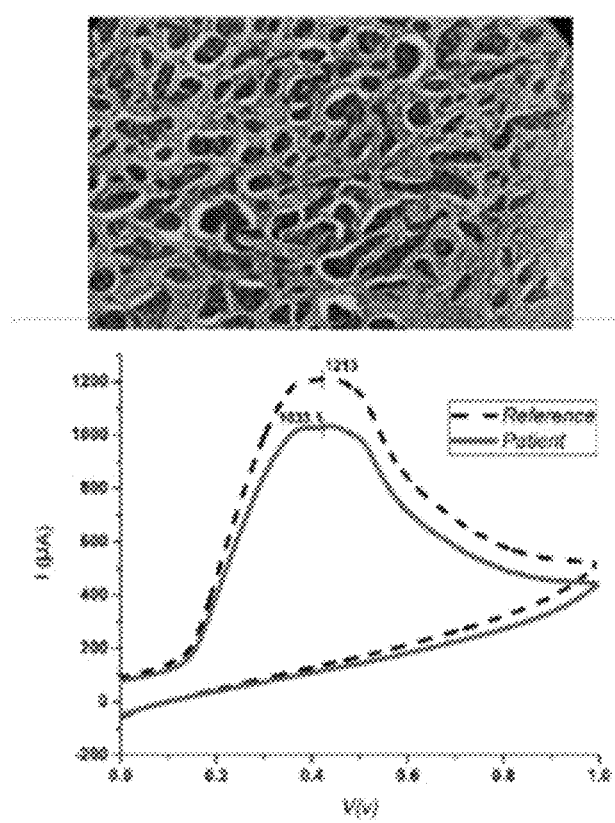
Figure 9F:
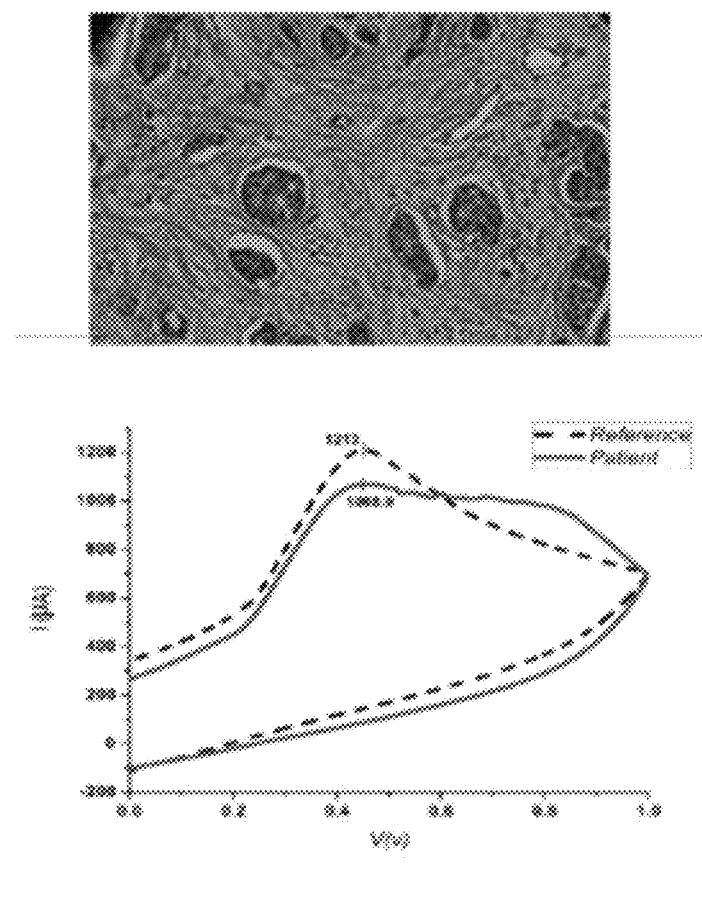

FIGS. 9A-9F show the cytopathological results (H&E images) (top side) and electrochemical responses (bottom side) of the breast tissues removed by biopsy or surgery from 6 suspicious patients to cancer, consistent with one or more exemplary embodiments of the present disclosure. The electrochemical responses were calibrated based on the reference $H_2O_2$ contained lactate solution with a lactate concentration of about 0.3 mM as used for cell lines in EXAMPLE 4 above. The intensity of oxidation peak and released electrons strongly correlated to the lactate produced by hypoxia glycolysis in cancer cells. A well correlation could be observed between increased $H_2O_2$ dependent current peak and cancer transformed morphology of the tissues. A great match observed between the quantified electrochemical response and pathological result of the samples in which the normal and hyperplasic tissues expressed low levels of $H_2O_2$ related current peak meanwhile the cancerous tissues exhibited high levels of $H_2O_2$ related electrochemical peaks. Accordingly, FIGS. 9A-9C show results obtained from non-cancerous samples and FIGS. 9D-9F show results obtained from cancerous samples.

Figure 10:
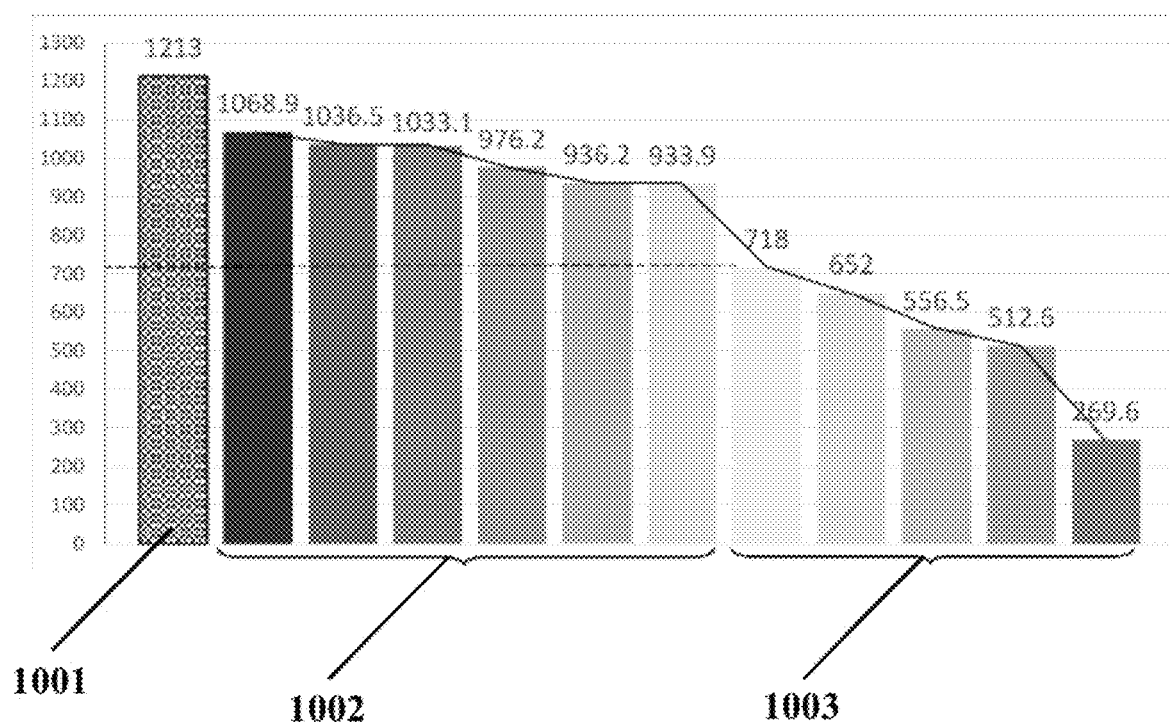
FIG. 10 illustrates a columnar diagram of electrochemical responses of the breast tissues removed by biopsy or surgery from 11 suspicious patients to cancer, consistent with one or more exemplary embodiments of the present disclosure.

Similar electrochemical responses of 5 more samples, including live spices from CNB or surgically removed samples, were obtained using exemplary CNT based electrochemical chip. FIG. 10 shows a columnar diagram of electrochemical responses of the breast tissues removed by biopsy or surgery from 11 suspicious patients to cancer, consistent with one or more exemplary embodiments of the present disclosure. Referring to this figure, two regimes 1002 and 1003 of responses were achieved due to the trace of hypoxia glycolysis based on LADH in comparison with a reference state 1001 of a $H_2O_2$ contained lactate solution with a lactate concentration of about 0.3 mM. In regime 1 indicated by 1002, the oxidation peaks were ranged from about 933.9 µA to about 1068.9 µA, and in regime 2 indicated by 1003, the oxidation peaks were ranged from about 269.6 µA to about 718 µA. The pathological results showed a well correlation with this determination. The samples presented high levels of hypoxia related oxidative peaks (categorized in regime 1) were verified as cancer in their H&E assays. Nests of distinguished tumoral cells in H&E images of those patients could be observed in FIGS. 9D-9F. Such responses were observed in the $H_2O_2$ contained lactate solution with the concentration of more than about 0.05 mM (FIG. 6B). Samples with low levels of lactate (regime2) were diagnosed as non-cancer with different types of benign cancer patients such as hyperplasia (peak: 556.5 µA) in FIG. 9B, lactational changes (peak: 718 µA), and so on. These electrochemical responses were equal to the peak determined in $H_2O_2$ contained lactate solution with the concentration of less than about 0.025 mM (FIG. 6B). Comparative columnar diagram presented in FIG. 10 would elaborate the difference in lactate based electrochemical response between normal and cancer tissues.

Example 6: Standard Colorimetric Lactate Assay Kit

As the released $H_2O_2$ concentration have a direct correlation with lactae concentration, to further investigate the accuracy of exemplary electrochemical method described above, the results of both cell lines (described in EXAMPLE 4) and patients' samples (described in EXAMPLE 5) were compared by standard colorimetric lactate assay kit. Although this method is so time consuming and expensive with complicated multi sequential steps, it was conducted to check the reliability of lactate concentration based cancer diagnosis measured by exemplary CNT based electrochemical chip. Comparative responses versus reference $H_2O_2$ contained lactate solution for both electrochemical and Lactate Kit assays are presented in Table 1 and Table 2.

TABLE 1

Comparative responses of CNT based electrochemical chip and standard Lactate Kit Assay on 4 different phenotypes of Breast cell lines.

| Cell line | Electrochemical sensor: Relative Current (%) | Lactate kit: Relative Lactate Concentration (%) |
|---|---|---|
| Reference lactate solution | 100 | 100 |
| MCF 10A | 31.1 | 31.1 |
| MCF-7 | 52.9 | 56.3 |
| MDA-MB-231 | 69.5 | 703 |
| MDA-MB-468 | 91.5 | 91.3 |

TABLE 2

Diagnostic results of 11 patients suspicious to breast cancer determined by H&E,
Lactate kit, and cathodic peaks od released $H_2O_2$ from the cells measured by CNT based
electrochemical chip assays, respectively

| Patient ID | Type of Tissue | H & E Result | Lactate Kit | CNT Electrochemical Sensor (%) |
|---|---|---|---|---|
| Reference lactate solution | — | — | 100 | 100 |
| 1 | Normal | Nex Cancer | 22.2 | 22.2 |
| 2 | Normal | Left Hyper Plasy | 42.3 | 42.3 |
| 3 | Normal | Lactational Change | 59.1 | 59.2 |
| 4 | Normal | Adenosis benign glandular prolifration | 53.8 | 33.7 |
| 5 | Normal | Hyperplasy and inflammation | 45.9 | 45.9 |
| 6 | Suspiciens to Cancer | Lympho vascular invasion | 88.1 | 88.2 |
| 7 | Suspicious to Cancer | Cancer | 77.2 | 77.2 |
| 8 | Suspicious to Cancer | Cancer | 35.5 | 85.4 |
| 9 | Suspicious to Cancer | Cancer | 80.5 | 80.5 |
| 10 | Suspiceus to Cancer | Cancer | 85.1 | 85.2 |
| 11 | Suspicious to Cances | Cancer | 62 | 62.2 |

A correlation was observed between the responses of the CNT based electrochemical chip and kit which revealed the accuracy of CNT based electrochemical chip in lactate based cancer detection as shown in Table 1 and Table 2. The raw values recorded by Lactate kit and electrochemical sensing wells were presented in these tables. In summary, tracing the hypoxia glycolysis (correlated with lactate concentration) in the interstitial fluid of biopsy sample by electrochemical assay with suitable electrode (such as CNT) exhibited a high correlation with their pathological states and may be used as a new method in cancer diagnosis.

Example 7: Integrated Assay on the Tin of the Needles of Caner Diagnostic Probe (CDP) for Real-Time Cancer Detection Both In Vitro and In Vivo To extend the application of exemplary label free electrochemical method of the present disclosure in real-time and precise detection of the tumor tissues during interventional sonography or surgery, exemplary CDP fabricated by growth of carbon nanostructures on the tip of the sterile steel needles as described in EXAMPLE 2 was used herein. Such integrated system contains three carbonated needles as working electrode (WE), counter electrode (CE), and reference electrode (RE). The needles were rinsed by PBS, Ethanol 70% and DI water followed by drying in $N_2$ ambient and UV sterile to prevent from any detachment and remaining the residues of the nanotubes in the tissue. CV responses were taken immediately after squeeze of exemplary CDP into the breast cancerous and normal tissues that indicated sharp increase in the current peak of the CDP with CNT covered electrodes interacted by cancer tissue. The important point is that the diagnosis was completed in live time based on monitoring the lactate concentration of the tissues inner domain.

Figure 11A:
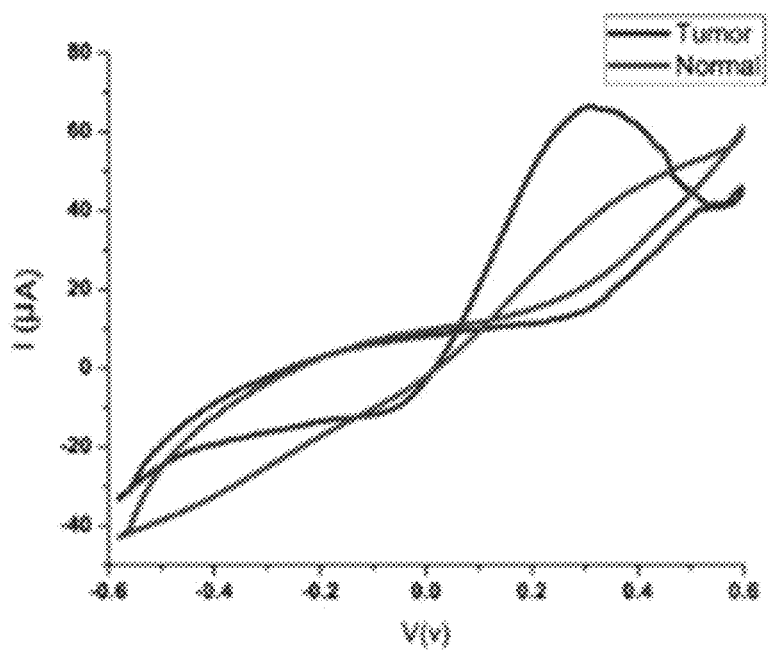
FIG. 11A illustrates CV response of exemplary CDP with all three needles covered by VAMWCNTs immediately after connection to the tissues, consistent with one or more exemplary embodiments of the present disclosure.

FIG. 11A shows CV response of exemplary CDP with all three needles covered by VAMWCNTs immediately after connection to the tissues, consistent with one or more exemplary embodiments of the present disclosure. It may be observed that reversible shapes with symmetric anodic and catholic peaks were obtained in CV responses. Distinguishable response between normal and cancer tissues may be observed.

Figure 11B:
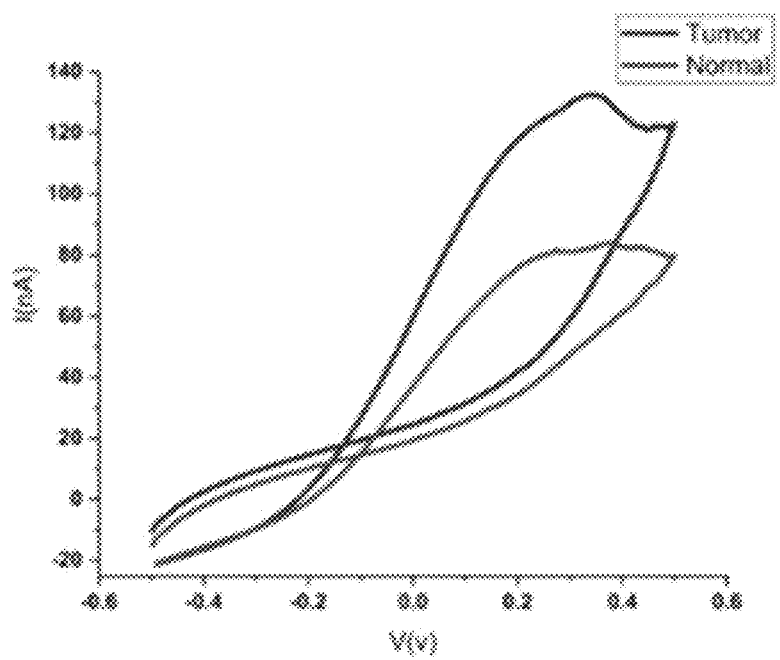
FIG. 11B illustrates CV response of exemplary CDP with only working electrode covered by VAMWCNTs immediately after connection to the tissues, consistent with one or more exemplary embodiments of the present disclosure.

FIG. 11B shows CV response of exemplary CDP with only working electrode covered by VAMWCNTs immediately after connection to the tissues, consistent with one or more exemplary embodiments of the present disclosure. Quality of the peaks were degraded when replacing the RE and CE by steel needle. The intensity and symmetry of the responses were degraded in the sensor with just CNT covered WE (CE and RE were steel needles).

Figure 11C:
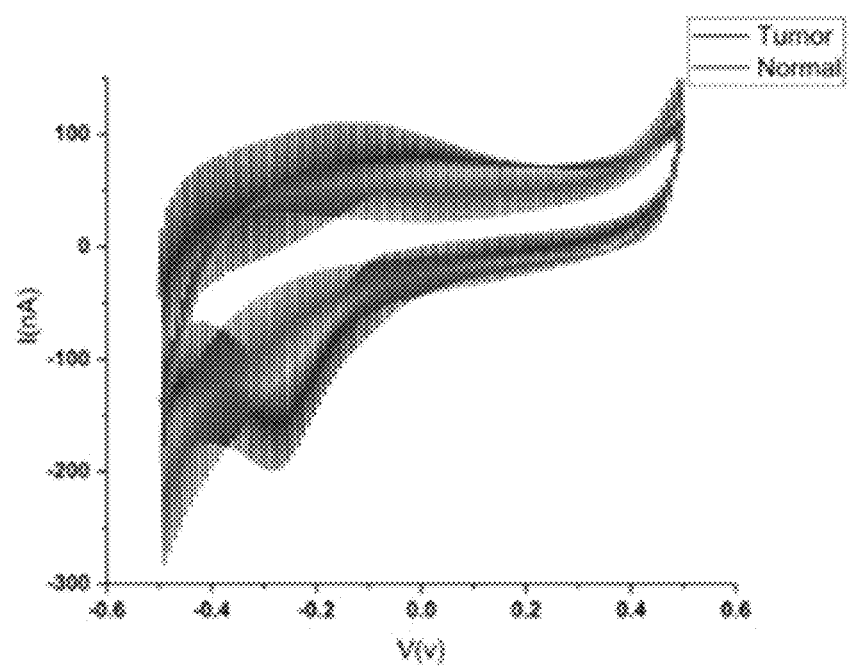
FIG. 11C illustrates CV response of exemplary CDP with non-CNT covered by needles immediately after connection to the tissues, consistent with one or more exemplary embodiments of the present disclosure.

FIG. 11C shows CV response of exemplary CDP with non-CNT covered by needles immediately after connection to the tissues, consistent with one or more exemplary embodiments of the present disclosure. There may be observed a noisy response without any distinguishable electrochemical peak. When all of the electrodes were non CNT covered needles, the responses were completely degraded and not distinguishable between normal and cancer tissues. This revealed the important role of CNT in selective interaction and charge transfer from the $H_2O_2$ released during transformation of lactate to pyruvate.

Figure 12A:
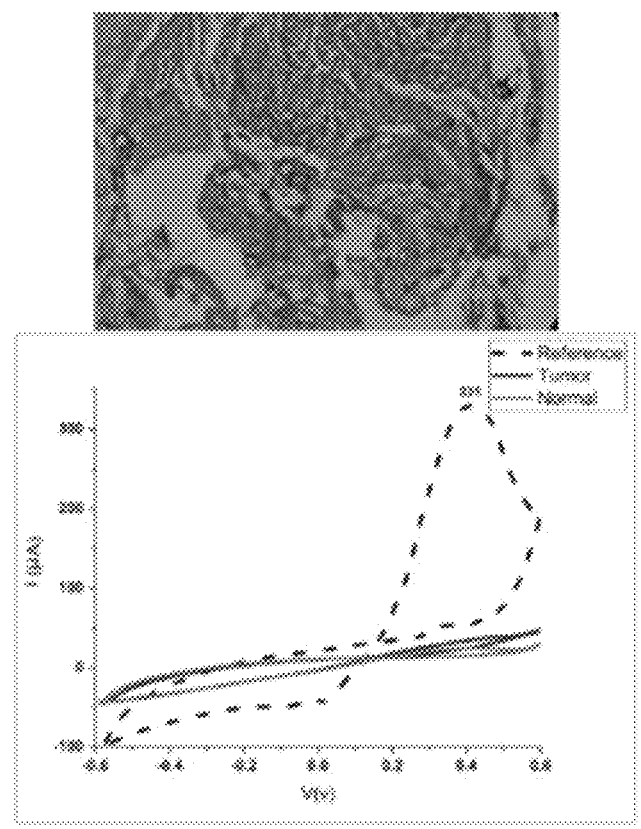
FIGS. 12A-12E illustrate CV responses recorded by exemplary CDP (needle based electrochemical sensor) from the resected tissues from five patients among 50 individual patients suspicious to breast cancer (bottom side) in comparison with images obtained by conventional pathological methods (H&E) (top side), consistent with one or more exemplary embodiments of the present disclosure.
Figure 12B:
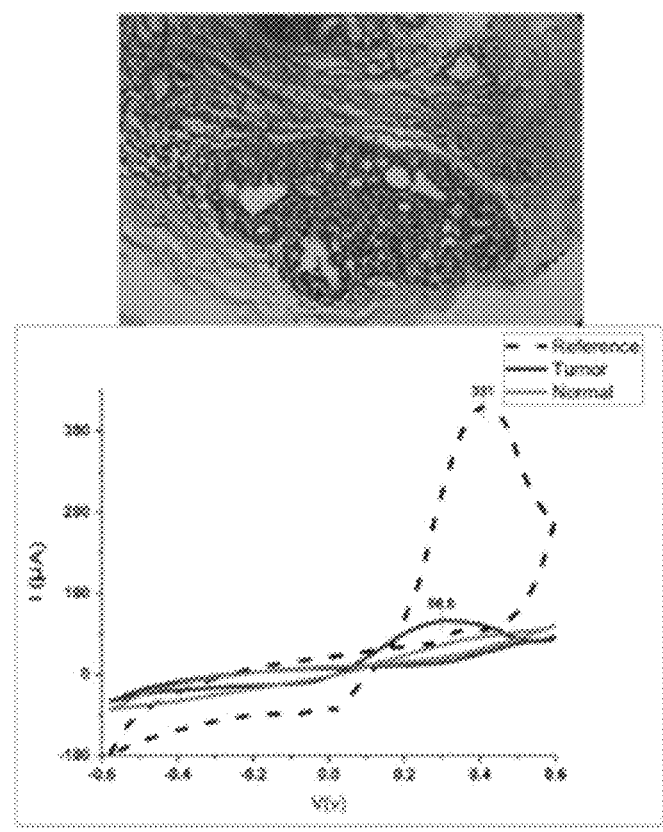
Figure 12C:
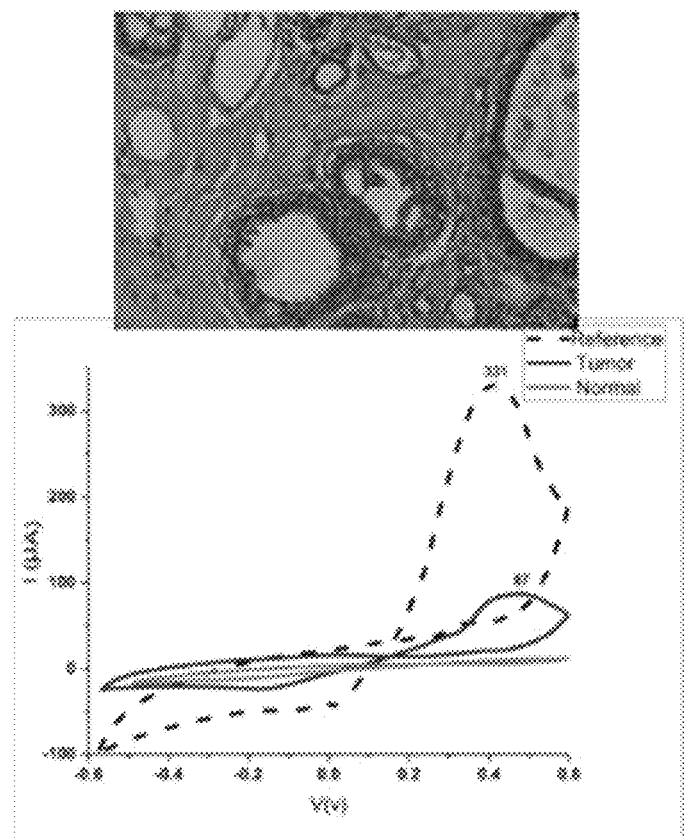
Figure 12D:
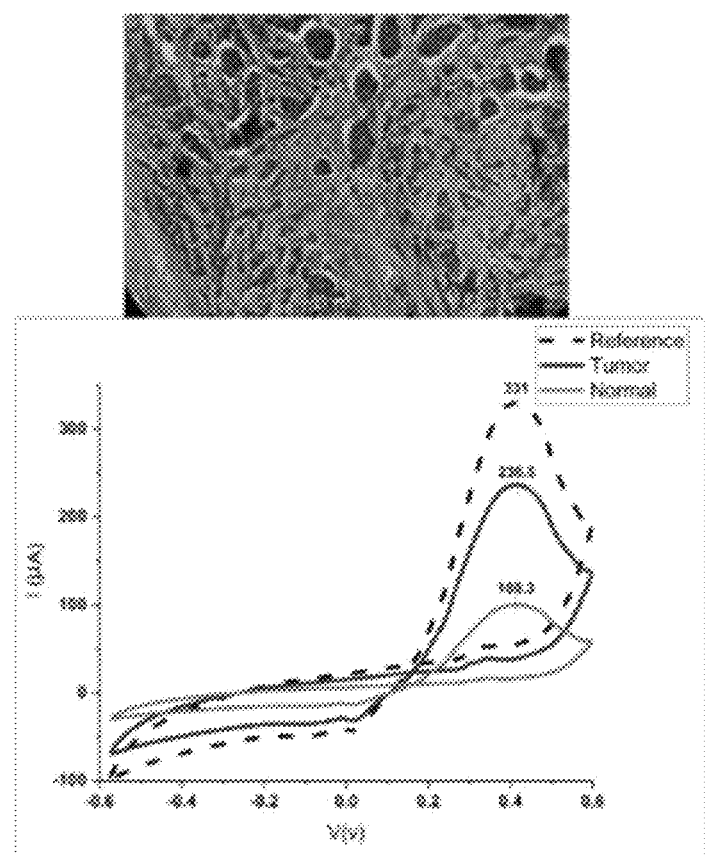
Figure 12E:
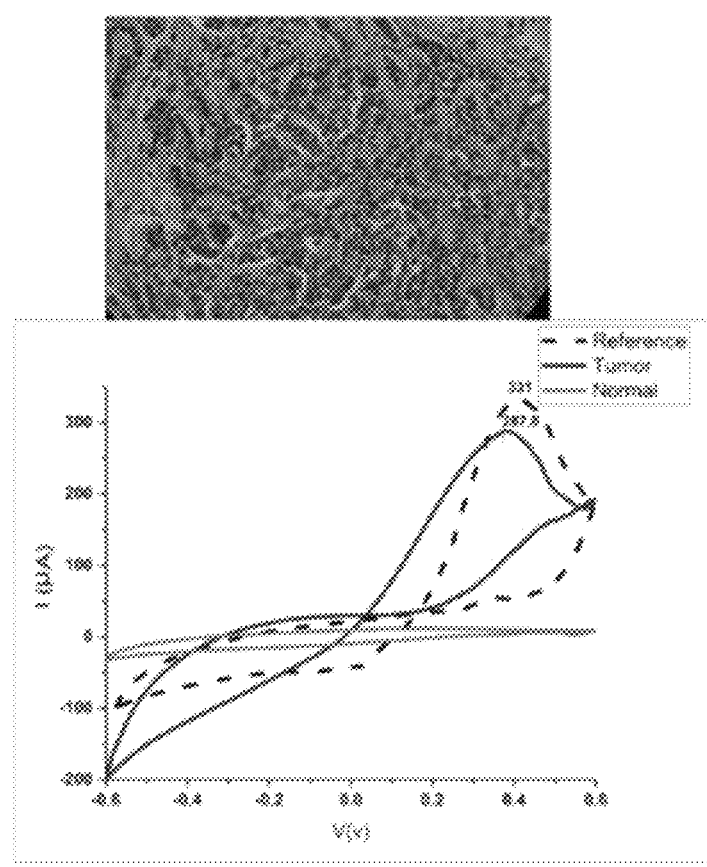

FIGS. 12A-12E show CV responses recorded by exemplary CDP (needle based electrochemical sensor) from the resected tissues from five patients among 50 individual patients suspicious to breast cancer at the bottom side of FIGS. 12A-12E in comparison with images obtained by conventional pathological methods (H&E) at the top side of FIGS. 12A-12E, consistent with one or more exemplary embodiments of the present disclosure. Patients respective to FIGS. 12A-12C have normal/non-cancerous (FIG. 12A), hyperplasic (FIG. 12B), and adenosis glandular proliferative tissues (FIG. 12C). Patients respective to FIGS. 12D and 12E have cancer tissues. Electrochemical current peaks of cancer tissues are sharply (more than about 150 μm) higher than benign ones with a strong correlation by the abundance of distributed cancer cells. The CV responses recorded from the normal and cancer tissues of these 50 individual patients by CNT covered needle sensors (CDP) greatly detected the hypoxic glycolysis just in cancerous samples due to cathodic peaks of $H_2O_2$ (FIGS. 12A-12E). Meanwhile, while the response time of CDP was less than about 1 minute after the tissue resection, diagnosis by conventional pathological methods (H&E) requires at least several hours for sample fixation and staining procedures. The ratio of cathodic peaks of reference $H_2O_2$ contained lactate solution vs. non-cancerous tissues were more than three times (FIGS. 12A-12C) while such ratio was less than one time in cancerous tissues (FIGS. 12D and 12E).

Table 3 shows the results recorded by exemplary CDP in comparison with the results obtained by H&E analysis from live resected tissues of 50 patients suspicious to breast cancer. They exhibited great correlations with the pathological results of the samples assayed by H&E method.

TABLE 3

Results recorded by exemplary CDP in comparison with the results obtained by H&E analysis from live resected tissues of 50 patients suspicious to breast cancer.

| Patient | Oxidation Current CDP Peaks (µA) | CDP (Cancer) | H&E (Cancer) |
|---|---|---|---|
| 1 | 0 | Negative | NO |
| 2 | 46.6 | Negative | NO |
| 3 | 87 | Negative | NO |
| 4 | 316.5 | Positive | YES (Cancer 90%, Normal 10%) |
| 5 | 287.8 | Positive | YES (Cancer 90%, Normal 10%) |
| 6 | 22 | Negative | NO |
| 7 | 142.3 | Positive | YES (Cancer 30%, Normal 70%) |
| 8 | 150 | Positive | YES (Cancer 30%, Normal 70%) |
| 9 | 300 | Positive | YES (Cancer 90%, Normal 10%) |
| 10 | 13 | Negative | NO |
| 11 | 0 | Negative | NO |
| 12 | 101.5 | Positive | YES (Cancer 30%, Normal 70%) |
| 13 | 180.2 | Positive | YES (Cancer 60%, Normal 40%) |
| 14 | 289.4 | Positive | YES (Cancer 90%, Normal 10%) |
| 15 | 302 | Positive | YES (Cancer 90%, Normal 10%) |
| 16 | 274.2 | Positive | YES (Cancer 90%, Normal 10%) |
| 17 | 0 | Negative | NO |
| 18 | 142.8 | Positive | YES (Cancer 30%, Normal 70%) |
| 19 | 80 | Negative | NO |
| 20 | 32.5 | Negative | NO |
| 21 | 200 | Positive | YES (Cancer 60%, Normal 40%) |
| 22 | 188.2 | Positive | YES (Cancer 60%, Normal 40%) |
| 23 | 264.5 | Positive | YES (Cancer 90%, Normal 10%) |
| 24 | 23 | Negative | NO |
| 25 | 179.5 | Positive | YES (Cancer 60%, Normal 40%) |
| 26 | 55.2 | Negative | NO |
| 27 | 52 | Negative | NO |
| 28 | 77 | Negative | NO |
| 29 | 0 | Negative | NO |
| 30 | 201 | Positive | YES (Cancer 60%, Normal 40%) |
| 31 | 75.6 | Negative | NO |
| 32 | 155.8 | Positive | YES (Cancer 30%, Normal 70%) |
| 33 | 99.5 | Positive | YES (Cancer 30%, Normal 70%) |
| 34 | 303.5 | Positive | YES (Cancer 90%, Normal 10%) |
| 35 | 297.7 | Positive | YES (Cancer 90%, Normal 10%) |
| 36 | 112 | Positive | YES (Cancer 30%, Normal 70%) |
| 37 | 17.8 | Negative | NO |
| 38 | 40 | Negative | NO |
| 39 | 73 | Negative | NO |
| 40 | 290 | Positive | YES (Cancer 90%, Normal 10%) |
| 41 | 90 | Positive | YES (Cancer 30%, Normal 70%) |
| 42 | 330 | Positive | YES (Cancer 90%, Normal 10%) |
| 43 | 197.5 | Positive | YES (Cancer 30%, Normal 70%) |
| 44 | 77.5 | Negative | NO |
| 45 | 25 | Negative | NO |
| 46 | 266.2 | Positive | YES (Cancer 90%, Normal 10%) |
| 47 | 0 | Negative | NO |
| 48 | 102.5 | Positive | YES (Cancer 30%, Normal 70%) |
| 49 | 310 | Positive | YES (Cancer 90%, Normal 10%) |
| 50 | 259.3 | Positive | YES (Cancer 90%, Normal 10%) |

Figure 13:
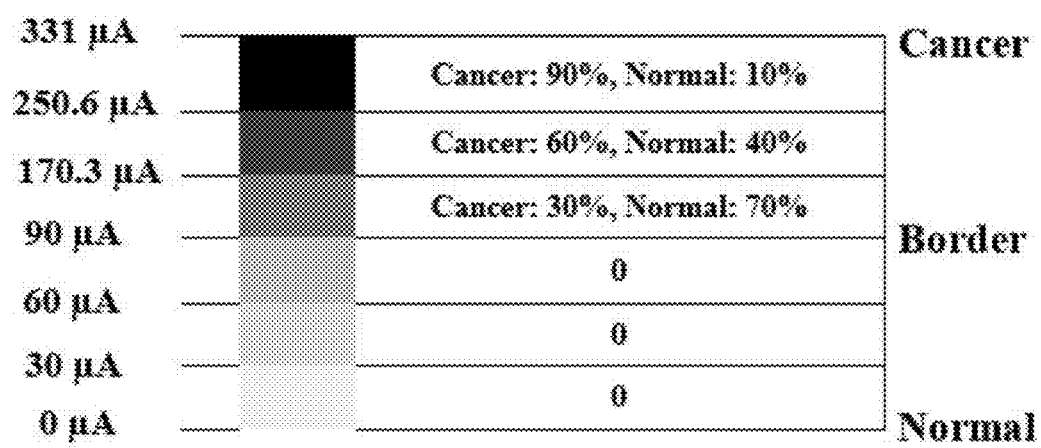
FIG. 13 illustrates a summary of categorized regimes of CV responses recorded by exemplary CDP from the resected tissues from five patients among 50 individual patients suspicious to breast cancer representing CV regimes along a spectrum from a completely non-cancerous state to cancerous state, consistent with one or more exemplary embodiments of the present disclosure.

FIG. 13 shows a summary of categorized regimes of CV responses recorded by exemplary CDP from the resected tissues from five patients among 50 individual patients suspicious to breast cancer that were presented in Table 3. It represents CV regimes along a spectrum from a completely non-cancerous state to cancerous state, consistent with one or more exemplary embodiments of the present disclosure. It may be seen that if the $H_2O_2$ cathodic peak (equal to oxidation current peak) of exemplary CV response recorded by exemplary CDP from a patient is less than 90 µA, the tissue is in non-cancerous state. On the other hand, if the CV response recorded by exemplary CDP from the tissue is in a range more than about 95 µA, there exists a cancerous state which may be more intensified by increasing the oxidation current peak. A range of oxidation current peak between 90 µA and 95 µA is the border range.

Example 8: In Vivo Analysis of Observable Tumor with Histologically Distinct Cancer Margin Before any Mastectomy To determine if CDP would in real time identify an observable tumor in vivo, about $2.3 \times 10^6$ 4T1-derived cancer cells were implanted into the back of 10 female BALB/C mice, and the mice were maintained in individual groups with similar size of formed tumors with sharp histologically distinct patterns. After about 10 days, individual CDPs were externally squeezed into their cancerous and normal regions had been specified by sonography. The space between each assayed regions was about 3 mm. Also the mice under body were connected to ground potential such as done for any patient in surgery room.

Figure 14A:
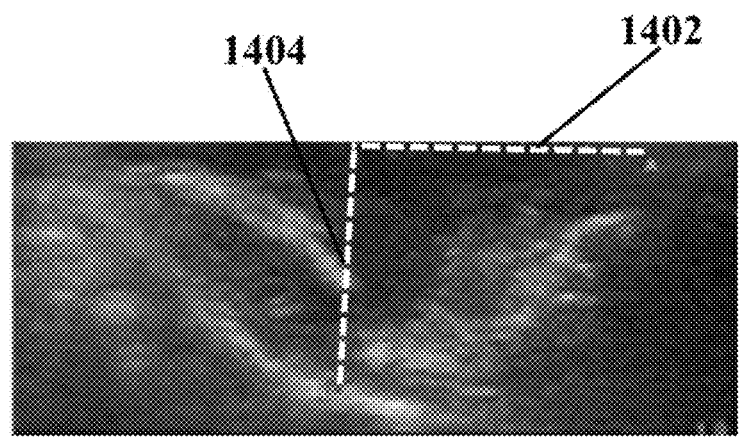
FIG. 14A illustrates a sonography image from a tumor side taken from an exemplary mouse tumorized by 4T1 breast cancer cell lines, consistent with one or more exemplary embodiments of the present disclosure.

FIG. 14A shows a sonography image from a tumor side taken from an exemplary mouse tumorized by 4T1 breast cancer cell lines, consistent with one or more exemplary embodiments of the present disclosure. A tumor with average sizes with a length 1402 of about 2.24 cm and another length 1404 of about 1.60 cm could be observed in sonography image.

Figure 14B:
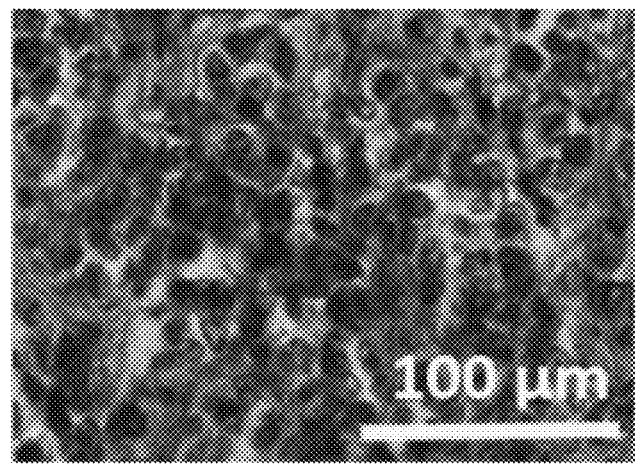
FIG. 14B illustrates H&E image from the tumor side taken from exemplary tumorized mouse by 4T1 breast cancer cell lines, consistent with one or more exemplary embodiments of the present disclosure.
Figure 14C:
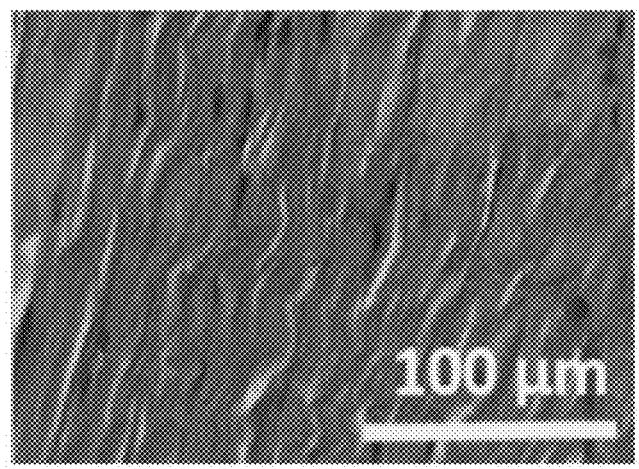
FIG. 14C illustrates H&E image from a normal/healthy side taken from exemplary tumorized mouse by 4T1 breast cancer cell lines, consistent with one or more exemplary embodiments of the present disclosure.

FIG. 14B shows H&E image from the tumor side taken from exemplary tumorized mouse by 4T1 breast cancer cell lines, consistent with one or more exemplary embodiments of the present disclosure. FIG. 14C shows H&E image from a normal/healthy side taken from exemplary tumorized mouse by 4T1 breast cancer cell lines, consistent with one or more exemplary embodiments of the present disclosure.

Figure 14D:
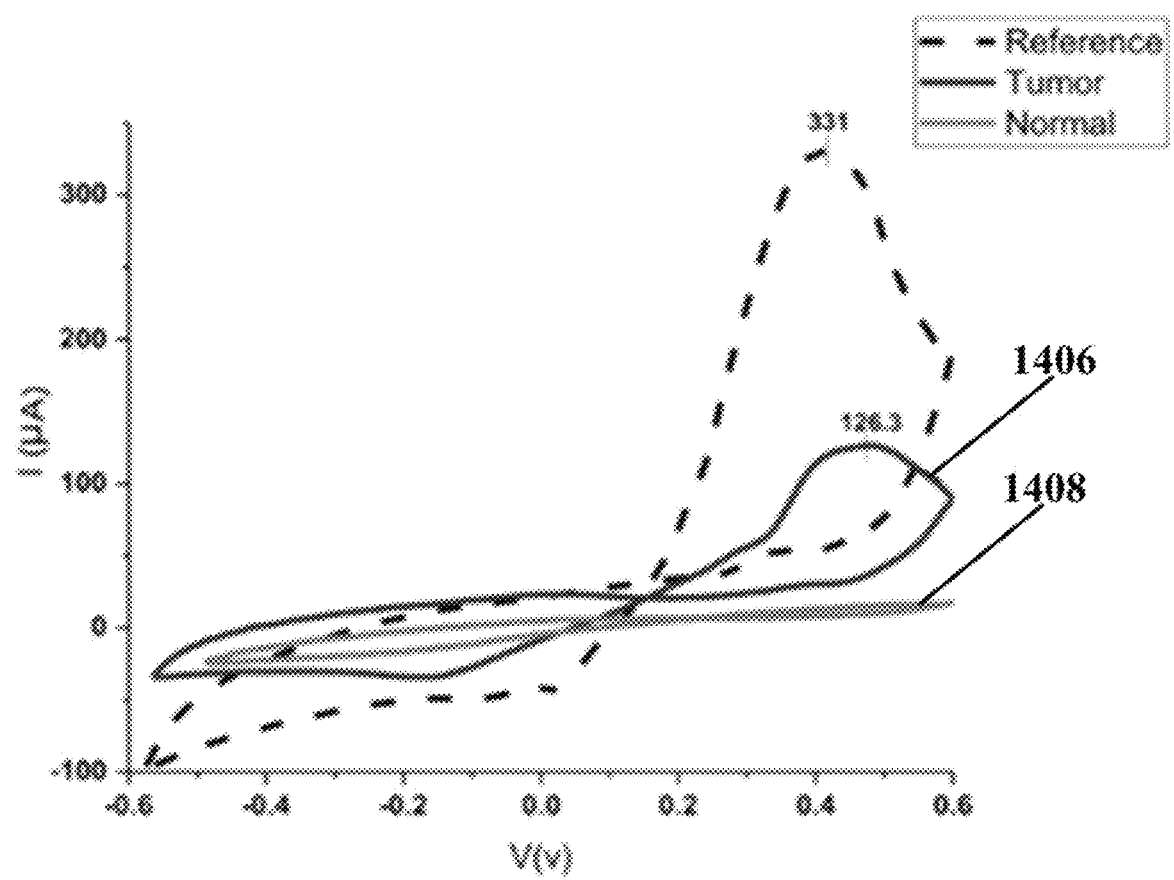
FIG. 14D illustrates CV diagrams of normal and tumor regions/sides of exemplary tumorized mouse by 4T1 breast cancer cell lines calibrated by a Reference CV diagram from $H_2O_2$ contained lactate solution with a lactate concentration of about 0.3 mM obtained using exemplary CDP, consistent with one or more exemplary embodiments of the present disclosure.

FIG. 14D shows CV diagrams of normal and tumor regions/sides of exemplary tumorized mouse by 4T1 breast cancer cell lines calibrated by a Reference CV diagram from $H_2O_2$ contained lactate solution with a lactate concentration of about 0.3 mM obtained using exemplary CDP, consistent with one or more exemplary embodiments of the present disclosure. It may be observed that the lactate related peaks were about 3 times higher in cancer region (CV diagram 1406 and FIGS. 14A and 14B) versus normal ones (CV diagram 1408 and FIG. 14C). Sharp lactate electrochemical peaks were observed in tumor locations by about three times higher current than that recorded from their normal regions To more clearly clarify the impact of $H_2O_2$ monitoring in tumor growth and progression, tumor size effects on $H_2O_2$ related electrochemical peaks recorded by CDP were compared. A distinguishable increasing regime was observed in the intensity of current peak through increment in the tumor size. Moreover, Histopathological images taken from the normal and cancer regions detected by CDP confirmed this result. Hyper chromatic and irregular nucleus with increased nucleus/cytoplasm ratio may be observable in H&E images of cancer region.

Example 9: In Vivo Analyses of Suspicious Regions Before and During the Surgery

In this example, the ability of the CDP to distinguish suspicious regions to cancer in mice model was analyzed by the resolution of about 3 mm which could be translated to human model. Tissue samples that contained regions of invasive breast cancer adjacent to normal stroma were experimented.

Figure 15A:
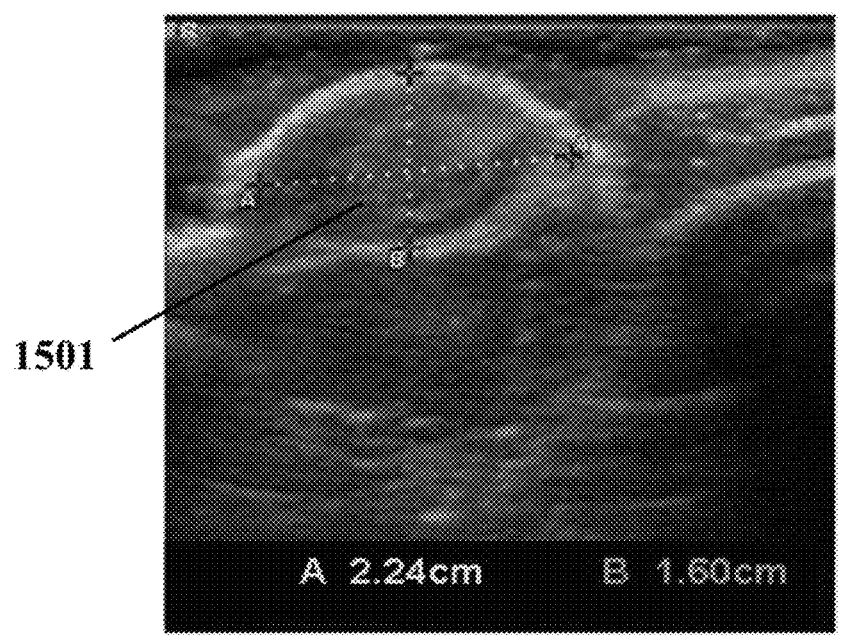
FIG. 15A illustrates a sonography image from a tumor taken from an exemplary mouse tumorized by 4T1 breast cancer cell lines, consistent with one or more exemplary embodiments of the present disclosure.

Five tumorized mice by 4T1 breast cancer cell lines were checked by sonography. FIG. 15A shows a sonography image from a tumor 1501 taken from an exemplary mouse tumorized by 4T1 breast cancer cell lines, consistent with one or more exemplary embodiments of the present disclosure. Approximate dimensions of the tumor could be observed in sonography image of FIG. 15A.

Figure 15B:
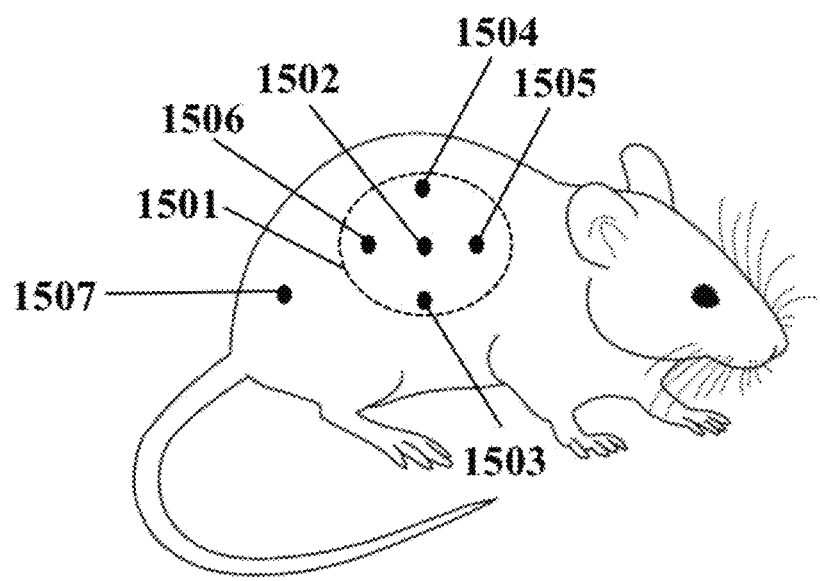
FIG. 15B illustrates exemplary six analyzed regions of an exemplary tumorized mouse among the exemplary five tumorized mice before surgery, consistent with one or more exemplary embodiments of the present disclosure.
Figure 15C:
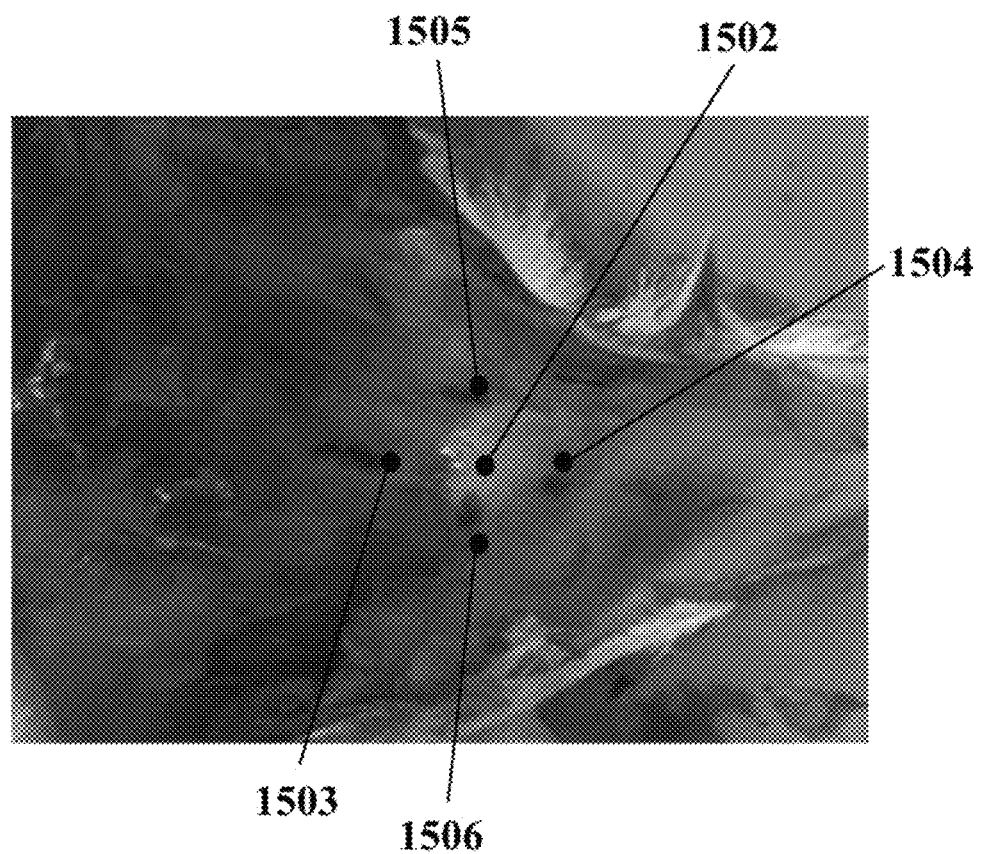
FIG. 15C illustrates exemplary six analyzed regions of an exemplary tumorized mouse among the exemplary five tumorized mice during surgery, consistent with one or more exemplary embodiments of the present disclosure.

Exemplary CDP was tested on tumor and suspicious regions of the five tumorized mice before (by squeezing through skin) and during the surgery on exemplary six regions. FIGS. 15B and 15C show exemplary six analyzed regions 1502-1507 of an exemplary tumorized mouse among the exemplary five tumorized mice before (FIG. 15B) and during surgery (FIG. 15C), consistent with one or more exemplary embodiments of the present disclosure. Six analyzed regions may include center 1562 of tumor 1501, left side 1503 of tumor 1501, right side 1504 of tumor 1541, upside 105 of tumor 1581, bottom side 1506 of tumor 1501, and also an exemplary normal side 1507 far from tumor 1501 all depicted in FIGS. 15B and 15C were analyzed consecutively before and during surgery using a CDP with an about 3 mm distance between needle electrodes.

Moreover, frozen H&E assay was used and rechecked by IHC method to be ensure from the precision of CDP results with respect to standard protocols. A tissue section of the sample including exemplary six regions analyzed by exemplary CDP was subjected to frozen H&E staining processes and evaluated by the pathologist. Exemplary tumor 1501 containing suspicious regions was removed and sent for frozen pathology and the H&E images taken from the center 1502 of tumor 1501 as well as its posterior 1505, anterior 1546, right 1504 and left 1503 laterals with the distance of about 3 mm from the histologically distinct region, were demanded by the CDP results as presented in Table 4. The results of CDP before and during surgery exhibited a perfect correlation. Ki67 based IHC assay confirmed the normal state of R5 and cancer involvement in R3 as classifier reference.

TABLE 4

Results recorded by exemplary CDP before and during surgery in comparison with the results obtained by H&E analysis from six suspicious regions of an exemplary tumorized mouse.

| Region | CDP Before Surgery (Ox Current Peaks (μA)) | CDP During Surgery (Ox Current Peaks (μA) | H&E frozen (Cancer) |
|---|---|---|---|
| 1502 (Center) | Positive (169.104) | Positive (178.621) | Yes (Cancer 90%, Normal 10%) |
| 1503 (Right) | Positive (94.773) | Posisive (96.89) | Yes (Cancer 30%, Normal 70%) |
| 1504 (Left) | Positive (122.643) | Positive (122.8) | Yes (Cancer 60%, Normal 40%) |
| 1505 (Up) | Negative (30.397) | Negative (31.85) | No |
| 1506 (Bottom) | Negative (0) | Negative (0) | No |
| 1507 (Normal) | Negative (0) | Negative (0) | No |

As represented in Table 4, it was distinguished from H&E analyzes that center 1502 was diagnosed by frozen histopathology as cancer tissue, whereas regions 1505 and 1506 were diagnosed as normal stroma. Region 1504 was in the margin between the cancer and normal stroma tissue regions, presenting about 40% tumor tissue and about 60% normal stroma tissue. Region 1503 was a suspicious region without any tumor margins but the trace of distributed cancer cells would be observed between stroma. Tumoral cells would be distinguished due to their hyper chromic nuclei (triangular arrows in H&E images of regions 1503 and 1504). Tabled result shows the CDP obtained for regions 1502 and 1504 presented significant hypoxic lactate peaks meanwhile lower but detectable meaningful levels of the $H_2O_2$ was recorded for region 1503. No detectable trace of any peak was measured for region 1506. The CDP response obtained for 1507, diagnosed as reference normal stroma tissue, presented no $H_2O_2$ peak similar to that observed for 1506.

The CDP response obtained for regions 1504 and 1506 were then evaluated by Ki67 IHC as an independent validation set. The expression of Ki67 has been reported to be correlated with tumor cell proliferation and growth in routine pathological investigation and used as a diagnostic marker. Ki67 based IHC classifier identified no trace of cancer proliferation in region 1506 (as the normal stroma) and showed different intensities of filtrated cancer cells in region 1504. Similar results were obtained for 5 other animal models with suspicious regions in anterior, posterior, right and left laterals of their tumors.

In addition, exemplary CDP exhibited a fine distinguishable response in interaction with another type of cancer tumors (MC4L2) as cancer cells with lower invasive grades than 4T1 as experimented on mice models. Tumors formed by the injection of about $5 \times 10^5$ MC4L2 cells (mice primary breast cancer cell lines) were analyzed by exemplary CDP on 5 mice.

Figure 16:
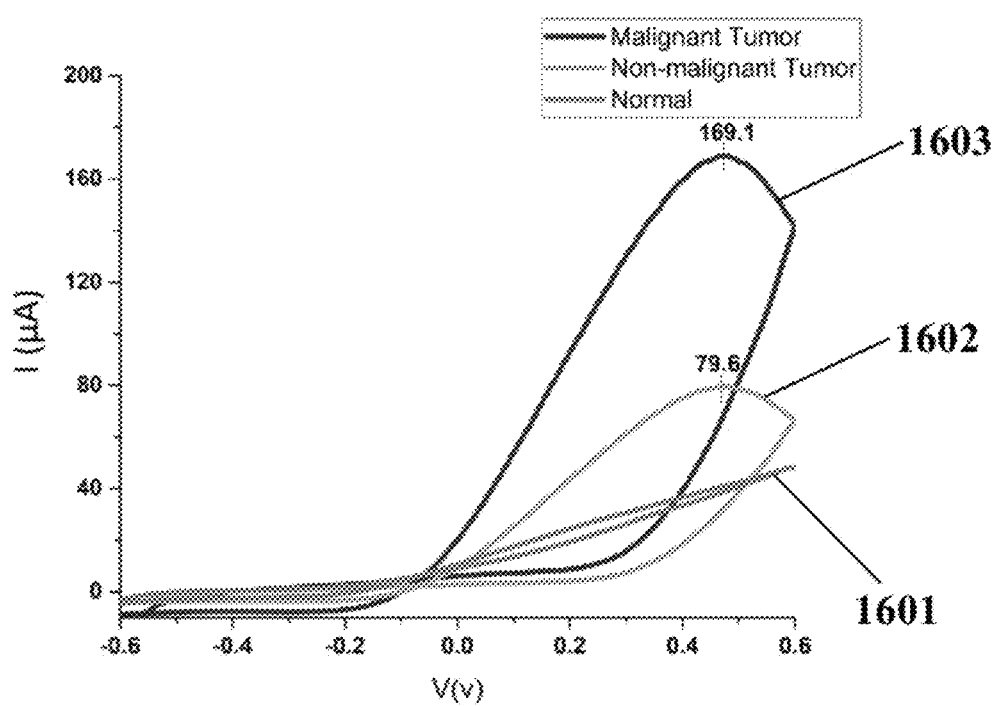
FIG. 16 illustrates comparative diagram of CDP responses in interaction with normal, nonmalignant tumor, and malignant tumor recorded from individual mice, consistent with one or more exemplary embodiments of the present disclosure.

FIG. 16 shows comparative diagram of CDP responses in interaction with normal (curve 1601), non-metastasized tumor (curve 1602) and metastatic tumor (curve 1603) recorded from individual mice, consistent with one or more exemplary embodiments of the present disclosure. Tracing the hypoxia glycolysis exhibited a strong correlation with the invasive state of the tumor. Results revealed sharply distinguishable responses between cancerous and normal regions. However the intensity of the response of MC4L2 tumors is lower than that was recorded for malignant tumor, it is observably higher than the response peak of normal tissue.

Furthermore, in this example, exemplary CDP was applied in finding the suspicious margins during tumor resection surgery in breast cancer patients. Not only the known normal domains were detected and set as reference point, but also suspicious margins of cancer and normal domains were precisely diagnosed in real-time and confirmed by histopathological assays. So, without requirement to frozen pathological process the surgeon can finish the surgery with insurance from precise resection of tumor without any additional mastectomy from the peripheral tissues.

Figure 17A:
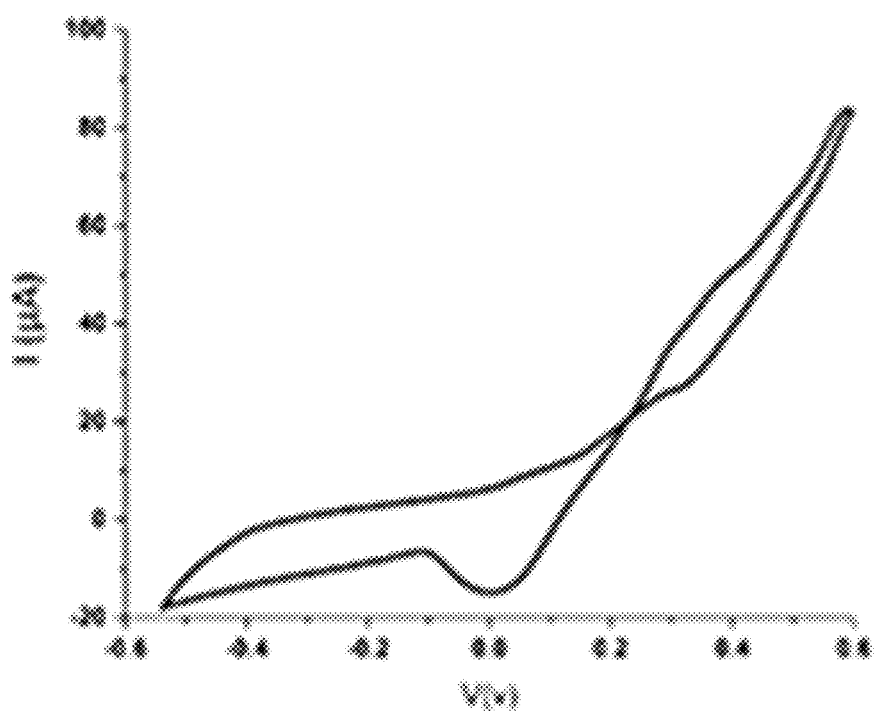
FIG. 17A illustrates CV response diagram obtained by applying exemplary CDP in detection of suspicious margins during breast cancer surgery for a known normal region, consistent with one or more exemplary embodiments of the present disclosure.
Figure 17B:
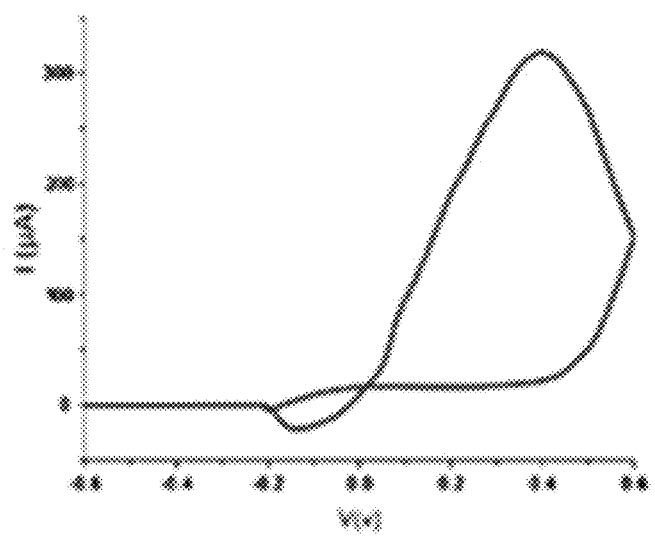
FIG. 17B illustrates CV response diagram obtained by applying exemplary CDP in detection of suspicious margins during breast cancer surgery for a suspicious region, consistent with one or mom exemplary embodiments of the present disclosure.
Figure 17C:
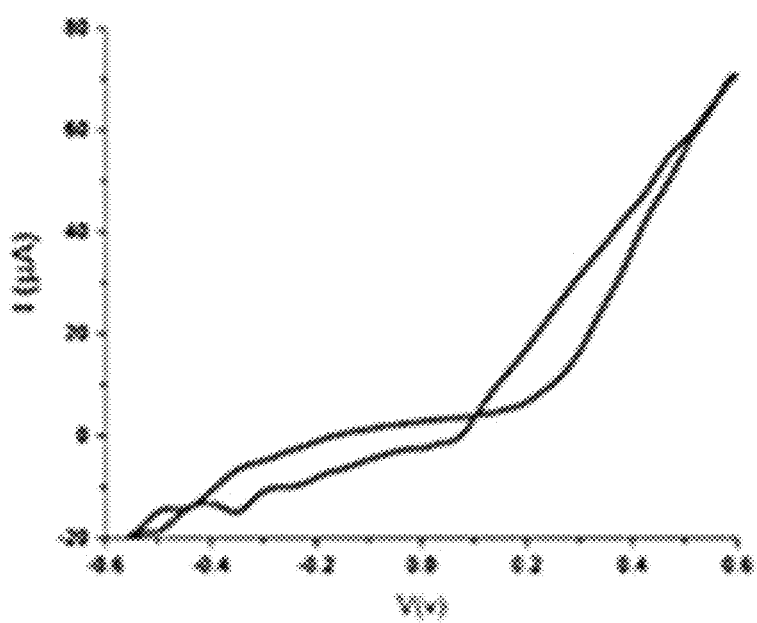
FIG. 17C illustrates CV response diagram obtained by applying exemplary CDP in detection of suspicious margins during breast cancer surgery for another suspicious region, consistent with one or more exemplary embodiments of the present disclosure.
Figure 17D:
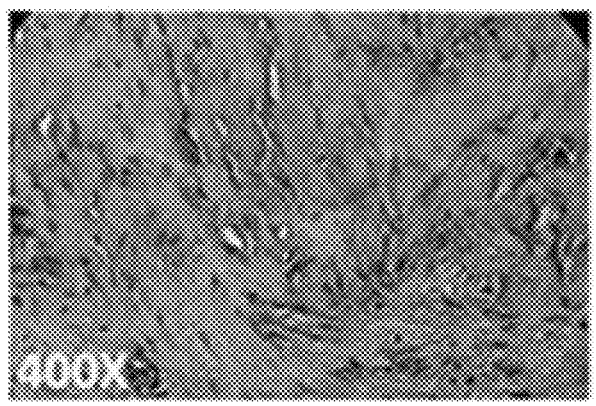
FIG. 17D illustrates an H&E resulted image after the surgery for a known normal region, consistent with one or more exemplary embodiments of the present disclosure.
Figure 17E:
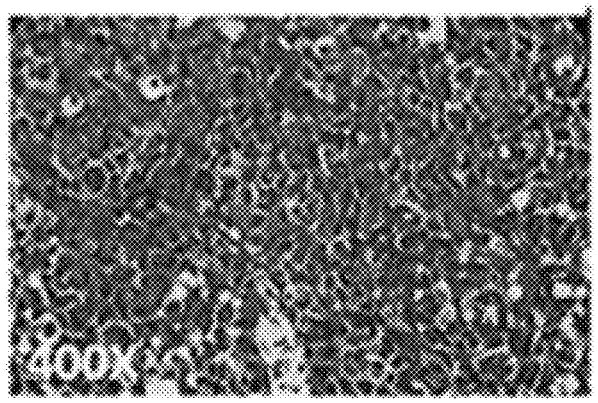
FIG. 17E illustrates an H&E resulted image after the surgery for a suspicious region, consistent with one or more exemplary embodiments of the present disclosure.
Figure 17F:
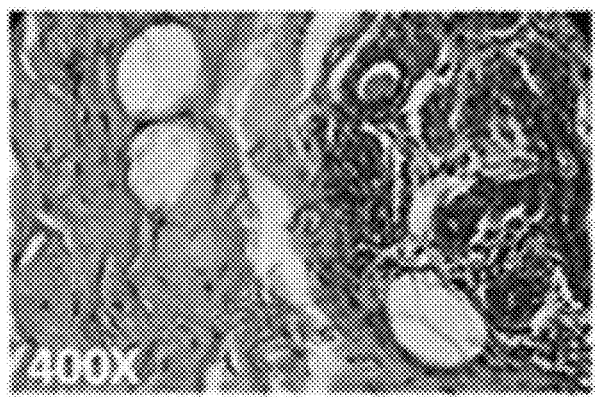
FIG. 17F illustrates an H&E resulted image after the surgery for another suspicious region, consistent with one or more exemplary embodiments of the present disclosure.

FIGS. 17A-17C shows CV responses obtained by applying exemplary CDP in detection of suspicious margins during breast cancer surgery for a known normal region (FIG. 17A) that was checked as calibrating data, and two suspicious margins (FIGS. 17B and 17C) that were precisely diagnosed as cancerous (FIG. 17B) and normal (FIG. 17C) domains by CDP in real-time, consistent with one or more exemplary embodiments of the present disclosure. The results obtained by exemplary CDP were confirmed by H&E analysis. FIGS. 17D-17F shows H&E results after the surgery for the known normal region, and two suspicious margins, consistent with one or more exemplary embodiments of the present disclosure.

These results show that the diagnostic information obtained by exemplary CDP can be used to detect cancer in marginal suspicious regions with rare distribution of cancer cells filtrated between normal stroma in less than about 20 seconds during the surgery or biopsy of live animal as well as human models without any requirement to tissue resection and preparation for frozen pathology. Even it may detect the accurate location of cancer involved regions before surgery in superficial tumors. The precision of this method is as well as reported for H&E from the assayed regions.

Example 10: Pathological Classification of Current Peaks Obtained by the Exemplary Fabricated CDP In this example, current peaks of 258 human fresh samples prepared from 74 breast cancer patients (Biopsied or surgically removed) were recorded utilizing exemplary CDP 102. 258 human fresh samples were tested immediately after dissection from the body (with the non-dehydrated weight of about 15-25 mg and size of up to about 1 cm². All three integrated needle electrodes of exemplary CDP 102, assembled on the head probe (the exemplary sensing part 154), were entered into a target tissue of the 258 human fresh samples at the same time. The whole process which may include replacing a previously used sensing part 154 by removing the previously used sensing part 154 and connecting a new sensing part 154 (about 20 sec), entering exemplary CDP 102 to the target tissue by inserting new sensing part 154 into a target location within the target tissue, and recording a CV response with a current peak from the target location (about 15 sec due to synchronized real-time processing) would take place in less than about 40 seconds. The permanent pathological diagnostic results of the samples which were re-checked by three histological slides from each sample, were a set of reference data in probable scalability of the recorded CV responses.

Figure 18:
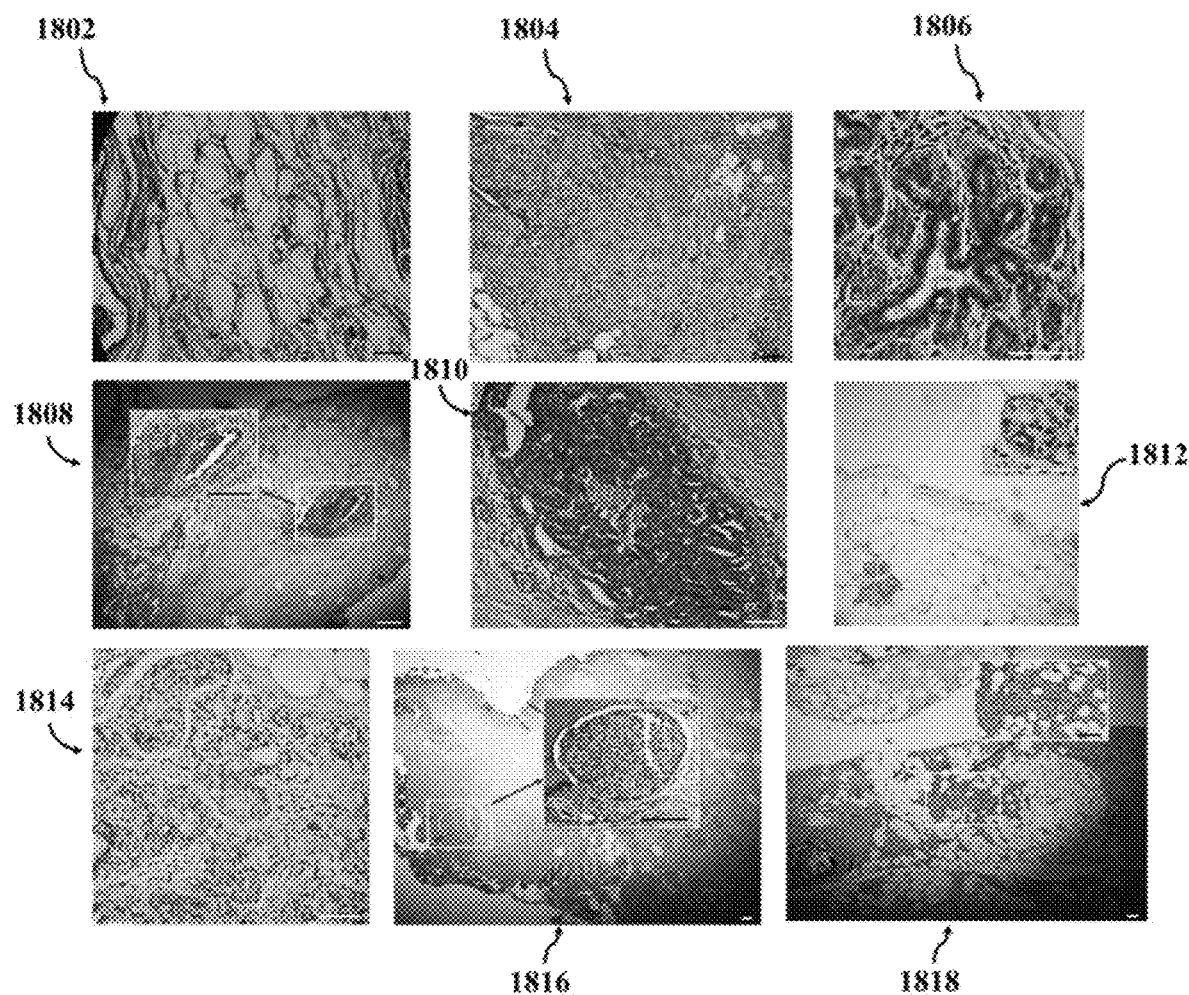
FIG. 18 illustrates H&E images from nine exemplary samples, consistent with one or more exemplary embodiments of the present disclosure.

Meaningful results were observed after comparing an experimental categorization of samples through their CDP recorded current peaks with their categorization through their H&E pathological diagnoses. Table 5 shows CDP current peak results of 258 fresh samples from 74 patients in association with pathological diagnosis based on pathological classification (DIN, LIN and FEL). Additionally. FIG. 18 shows H&E images 1802-1818 from nine exemplary samples associated with nine exemplary categories in Table 5, consistent with one or more exemplary embodiments of the present disclosure.

TABLE 5

CDP current peak results of 258 fresh samples from 74 patients in assoclation with pathological diagnosis based on pathological classification (DIN, LIN and FEL)

| Pathological Diagnosis (classification system) | Pathological scoring for re-excising recommendation (warning state) | Ranges of recorded CDF peak current (μA) | Number of tested samples | Number of the matched samples in CDP ranges |
|---|---|---|---|---|
| Fatty breast tissue (FEL) | Negative | 0-40 | 15 | 14 |
| Sclerosing adenosis (DIN) | Negative | 83-115 | 11 | 8 |
| FCC with CCC (DIN) | Negative | 110-117 | 19 | 17 |
| Moderate usual ductal hyperplasia (DIN) | Negative | 117-137 | 12 | 10 |
| Florid ductal hyperplasia (DIN) | Negative (moderate risk) | 150-170 | 10 | 8 |
| Stroma + one focus of ADH (DIN) | Negative (moderate risk) | 175-196 | 5 | 4 |
| Stroma + two of more foci of ADH; DIN1b (DIN) | positive | 203-260 | 31 | 28 |
| Stroma + one foci of DCIS; DIN1c (DIN) | positive | 231-290 | 24 | 21 |
| IDC >5% | positive | 360 and more | 19 | 19 |

It was observed that 26 samples among 258 samples were normal breast stroma, including fatty breast tissues and simple fibroadenoma, which all showed current peaks in a range of about 0-83 μA as shown in Table 5. Image 1802 of FIG. 18 shows H&E image from an exemplary sample including fatty breast tissue (FEL) as a normal breast tissue with a current peak between about 0 μA and about 40 μA, consistent with one or more exemplary embodiments of the present disclosure. 18 samples were non proliferative fibrocystic changes (FCC) which all of them showed current peaks in a range of about 53-11 μA. 10 samples were mild usual ductal hyperplasia (UDH) which all of them showed current peaks in a range of about 83-110 μA. 11 samples were sclerosis adenosis (SA) which 8 of them showed current peaks in a range of about 86-115 μA. Image 1804 of FIG. 18 shows H&E image from an exemplary sample including sclerosis adenosis (SA) with a current peak between about 83 μA and about 115 μA, consistent with one or more exemplary embodiments of the present disclosure. 12 samples were moderate UDH which 10 of them showed current peaks in a range of about 120-137 μA. 19 samples were FCC with columnar cell changes (CCC)(some of them also had one foci suspicious to atypical ductal hyperplasia (ADH)) which 17 of them showed current peaks in a range of about 110-173 μA. Image 1866 of FIG. 18 shows H&E image from an exemplary sample including fibrocystic changes (FCC) with columnar cell changes (CCC) with a current peak between about 110 μA and about 117 μA, consistent with one or more exemplary embodiments of the present disclosure. Image 1808 of FIG. 18 shows H&E image from an exemplary sample including Moderate usual ductal hyperplasia (DIN) with a current peak between about 117 μA and about 137 μA, consistent with one or more exemplary embodiments of the present disclosure. Image 1810 of FIG. 18 shows H&E image from an exemplary sample including Florid ductal hyperplasia (DIN) with a current peak between about 150 μA and about 170 μA, consistent with one or more exemplary embodiments of the present disclosure. Image 112 of FIG. 18 shows H&E image from an exemplary sample including stroma with one focus of atypical ductal hyperplasia (ADH) with a current peak between about 175 μA and about 196 μA, consistent with one or more exemplary embodiments of the present disclosure. In summary, normal breast (e.g. breast fatty tissue), UDH (e.g. FCC lesions) and DIN1a (e.g. FCC with CCC and a small foci of ADH) showed response peak ranges from about 0 μA to about 196 μA which were negatively scored by CDP.

Moreover, 31 samples showed involvement to two or more foci of ADH which 28 of them showed peak currents in a range of about 203-250 μA. Image 1814 of FIG. 18 shows H&E image from an exemplary sample including stroma with two or more foci of ADH (DIN1b) with a current peak between about 203 μA and about 260 μA, consistent with one or more exemplary embodiments of the present disclosure. 24 samples showed involvement to low grade ductal carcinoma in-situ (DCIS), from about 10% to about 45% of the histological pattern, which 21 of those samples showed current peaks in a range of about 250-360 μA. Image 1816 of FIG. 18 shows H&E image from an exemplary sample including stroma with one foci of ductal carcinoma in-situ (DCIS) (DIN1c) with a current peak between about 231 μA and about 290 μA, consistent with one or more exemplary embodiments of the present disclosure. 12 samples were invasive ductal carcinoma (IDCs) with distributions between 5-55% of histological pattern, which all of them showed current peaks in a range of about 610-800 μA. 2 samples were phylloids tumor which both showed peak currents more than about 260 μA. Just 10 samples were found with lobular based atypia/neoplasia; 4 of those samples were invasive lobular carcinoma (ILC) with extensive distribution which all showed current peaks in a range of about 380-465 μA. 4 samples were atypical lobular hyperplasia (ALH) which showed current peaks between in a range of about 257-270 μA. 2 other samples were lobular carcinoma in-situ (LCIS) which both showed current peaks of about 290 μA. Image 1818 of FIG. 18 shows H&E image from an exemplary sample including invasive ductal carcinoma (IDC) with a current peak more than about 360 μA, consistent with one or more exemplary embodiments of the present disclosure.

Figure 19:
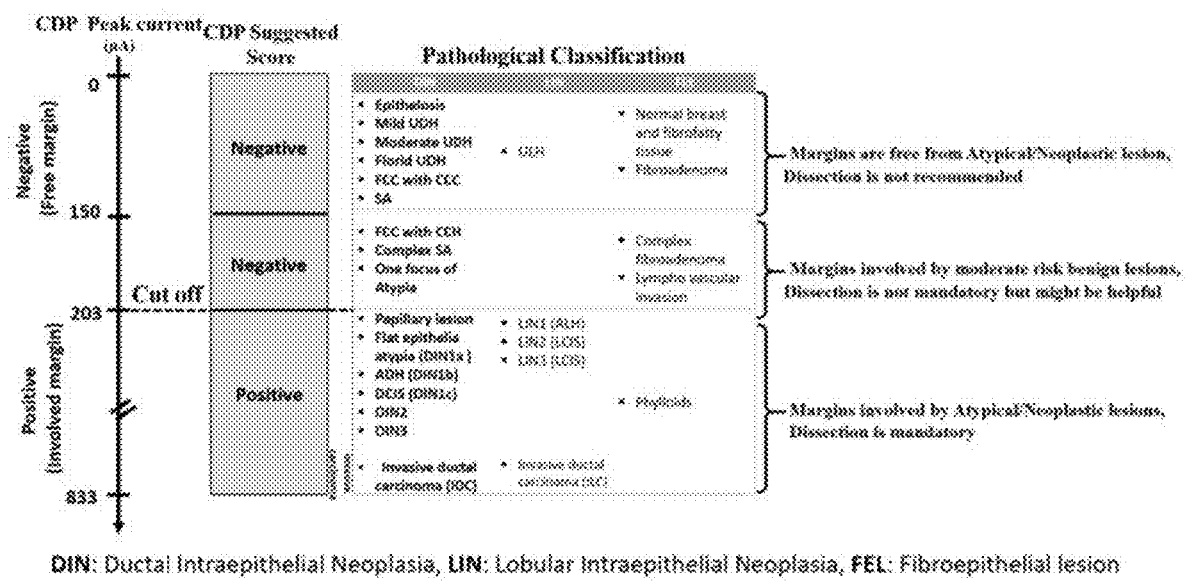
FIG. 19 illustrates classification of current peaks recorded by exemplary CDP after examining more than 250 samples in consistence with pathological diagnosis, consistent with one or more exemplary embodiments of the present disclosure.

Considering the above pathological results and current peaks of the samples together, a classification on CV responses recorded by exemplary CDP 102 was proposed based on pathological diagnosis. The lowest cut-off for pathologists on diagnosing a margin as positive (dissection is mandatory) is presence of at least two foci of ADH. Therefore, a border line at about 203 μA was proposed as a cut-off current for positive scoring exemplary CDP 102. Samples consisting of ADH with more than two foci, DCIS and IDCs most often showed peak currents higher than about 203 μA while other samples consisting of one foci of ADH, UDH and FCC lesions showed peak currents lower than about 196 μA. Hence, the responses of exemplary CDP 102 were found to be classifiable based on newest edition of ductal intraepithelial neoplasia (DIN), lobular intraepithelial neoplasia (LIN) and fibro-epithelial lesion (FEL) systems reported by world health organization (WHO). FIG. 19 shows classification of current peaks recorded by exemplary CDP 102 after examining more than 250 samples in consistence with pathological diagnosis, consistent with one or more exemplary embodiments of the present disclosure. It may be observed that samples with positively scored levels of glycolytic related $H_2O_2$ peaks were verified as ADH, DCIS, IDC and metastatic lymph nodes in their H&E assays showed more than about 203 μA (as the cut-off) in CDP response peaks. Samples with current peaks lower than about 196 μA were negatively scored by CDP as neither cancerous nor pre-cancerous tissue with different types of benign states such as usual ductal hyperplasia, adenosis, fibrosis and non-proliferative fibrocystic changes. Most of the abnormal samples were found in DIN classification (as the mostly occurred types of breast diseases such as IDC, DCIS, ADH and UDH). CDP peak responses were scored with a defined cut-off between free and involved margins (at 203 μA), respectively assigned as "Negative" and "positive". Such scoring would consider any pathological involvement to atypical, pre-invasive and invasive lesions in margin checking. Also, a warning regime in negative regions was defined in this classification. These samples with current peaks between about 137 μA and about 196 μA may be classified in this region. Surgeons need to be aware on these lesions through presence of complex fibroadenoma, complex SA or single focus of atypia. Although these lesions are not pathologically high risk pre-neoplasia, they ought to be reported and considered through some guidelines. DIN1b (e.g. two or more foci of ADH), DIN1c (e.g. low grade-DCIS), DIN2 (e.g. intermediate DCIS), DIN3 (e.g. high grade DCIS) and IDC lesions showed response peaks in the ranges between 203 to more than 600 μA which were positively scored by CDP. Based on this example, pathologically validated diagnostic scores of exemplary CDP 102 were defined for 258 breast tissue samples with sensitivity of about 95% and specificity of about 92% respectively. Such results may be achieved by CNT covered sensing needles of exemplary CDP 102 which may provide selective interaction with released $H_2O_2$ from abnormal tissues with no post recording perturbation on morphology and distributions of the sterilized CNT-covered needles.

Example 11: Real-Time In-Vivo Scoring of External Margins (EMs) and Internal Margins (IMs) by CDP During Breast Cancer Surgery in Human Models In this example, exemplary prepared CDP 102 was utilized through exemplary method 200 as a real-time diagnostic tool to find involved body side margins (named IMs) during human cancer surgery. In this regard, exemplary prepared CDP 102 was applied in real-time finding of suspicious IMs and EMs during lumpectomy and/or mastectomy of 127 patients with different types of breast tumors in different steps of treatment. 14 patients were excluded from the survey and 113 patients (107 female and 6 male) were included. All of the tests were done under the license of Ethics Committee with the informed consent of candidate patients. The sensing needles (i.e., exemplary working electrode 158, counter electrode 160 and reference electrode 162) were entered into the margins up to a depth of about 4 mm and a stopping specimen was embedded on exemplary head 166 to prevent from further entrance of the needles. A distance between the exemplary three electrodes was about 3 mm. Hence, more than about 30 mm³ of exemplary portion of breast tissue was exposed to exemplary CDP 102 during each test. Depending on a surgeon's opinion, up to 12 breast margins (6 EMs on dissected tumor and 6 IMs in cavity side of a patient (including posterior, anterior, superior, inferior, medial and lateral) were intraoperatively checked by exemplary CDP 102 for each patient. The EMs on dissected tumor were diagnosed (scored) by CDP and the tested lesions were sent for frozen pathology. Subsequently, the IMs in cavity side (in the body of the patient) were checked by exemplary CDP 102 and similarly the tested lesions were considered by standard frozen pathology. Finally, all of EMs and IMs were diagnosed (scored) by exemplary CDP 102 and tested by frozen pathology, were individually evaluated by permanent pathology as reference standard diagnosis based on pathological classifications of breast tumors. Also, when a permanent histological pattern was suspicious for pathologist between two different diagnoses (e.g. UDH and ADH), IHC would be recommended by her/him. Totally, 895 individual EMs and IMs were intra operatively scored by CDP and diagnosed by pathology.

Figure 20A:
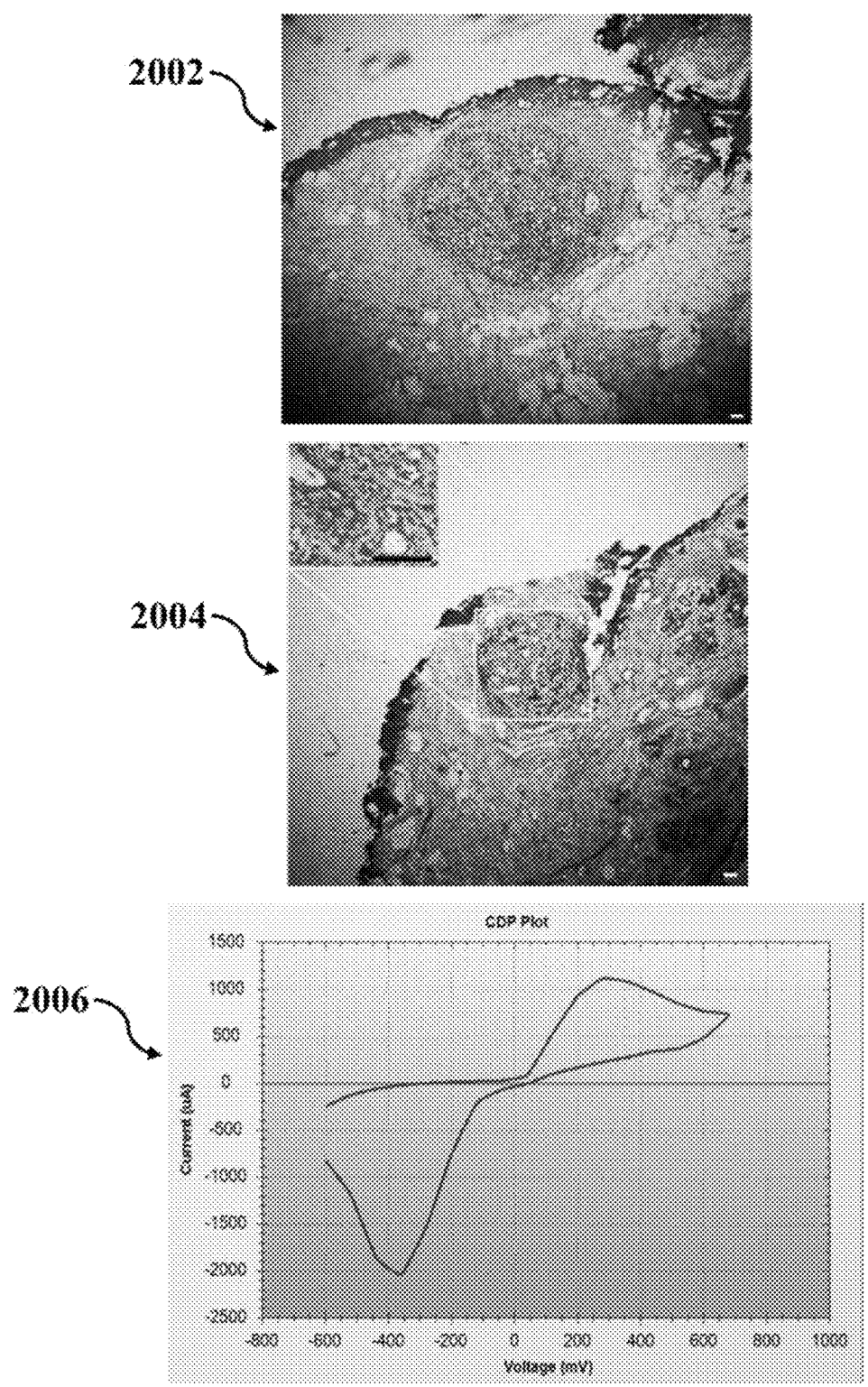
FIG. 20A illustrates an image resulted from frozen H&E (top-side image), an image resulted from permanent H&E (middle-side image), and a CV response recorded by exemplary CDP (bottom-side image) for the anterior IM of a patient (ID 18), consistent with one or more exemplary embodiments of the present disclosure.

FIG. 20A shows an image resulted from frozen H&E (top-side image 2082), an image resulted from permanent H&E (middle-side image 2004), and a CV response recorded by exemplary CDP 102 (bottom-side image 206) for the anterior IM of a patient (ID 18), consistent with one or more exemplary embodiments of the present disclosure. It may be observed that real-time CV response recorded by exemplary CDP 102 positively scored the margin, and both frozen and permanent H&E confirmed involvement of invasive ductal carcinoma for this patient.

Figure 20B:
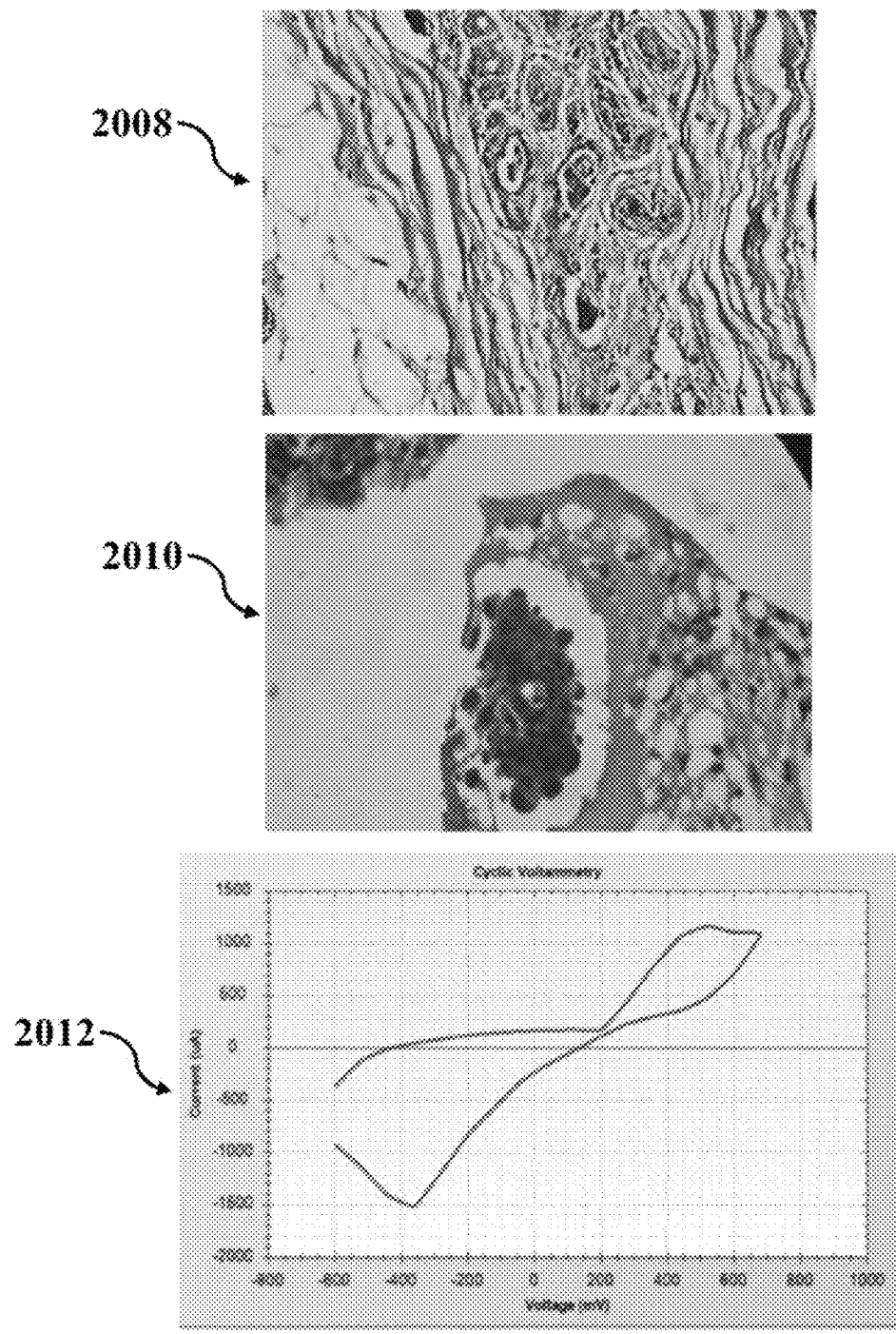
FIG. 20B illustrates an image resulted from frozen H&E (top-side image), an image resulted from permanent H&E (middle-side image), and a CV response recorded by exemplary CDP (bottom-side image) for a suspicious margin inside the body of the patient (anterior margin of patient ID 46), consistent with one or more exemplary embodiments of the present disclosure.

FIG. 20B shows an image resulted from frozen H&E (top-side image 2008), an image resulted from permanent H&E (middle-side image 2010), and a CV response recorded by exemplary CDP 102 (bottom-side image 2012) for a suspicious margin inside the body of the patient (anterior margin of patient ID 46), consistent with one or more exemplary embodiments of the present disclosure. It may be observed that real-time CV response recorded by exemplary CDP 102 positively scored the margin, and the removed specimen showed negative result for malignancy in frozen analyses meanwhile the permanent H&E showed the papillary lesion with Atypia region, which must be removed by surgeon. This example may show the significant role of using exemplary CDP 102 for high-accurate cancer diagnosis.

Figure 20C:
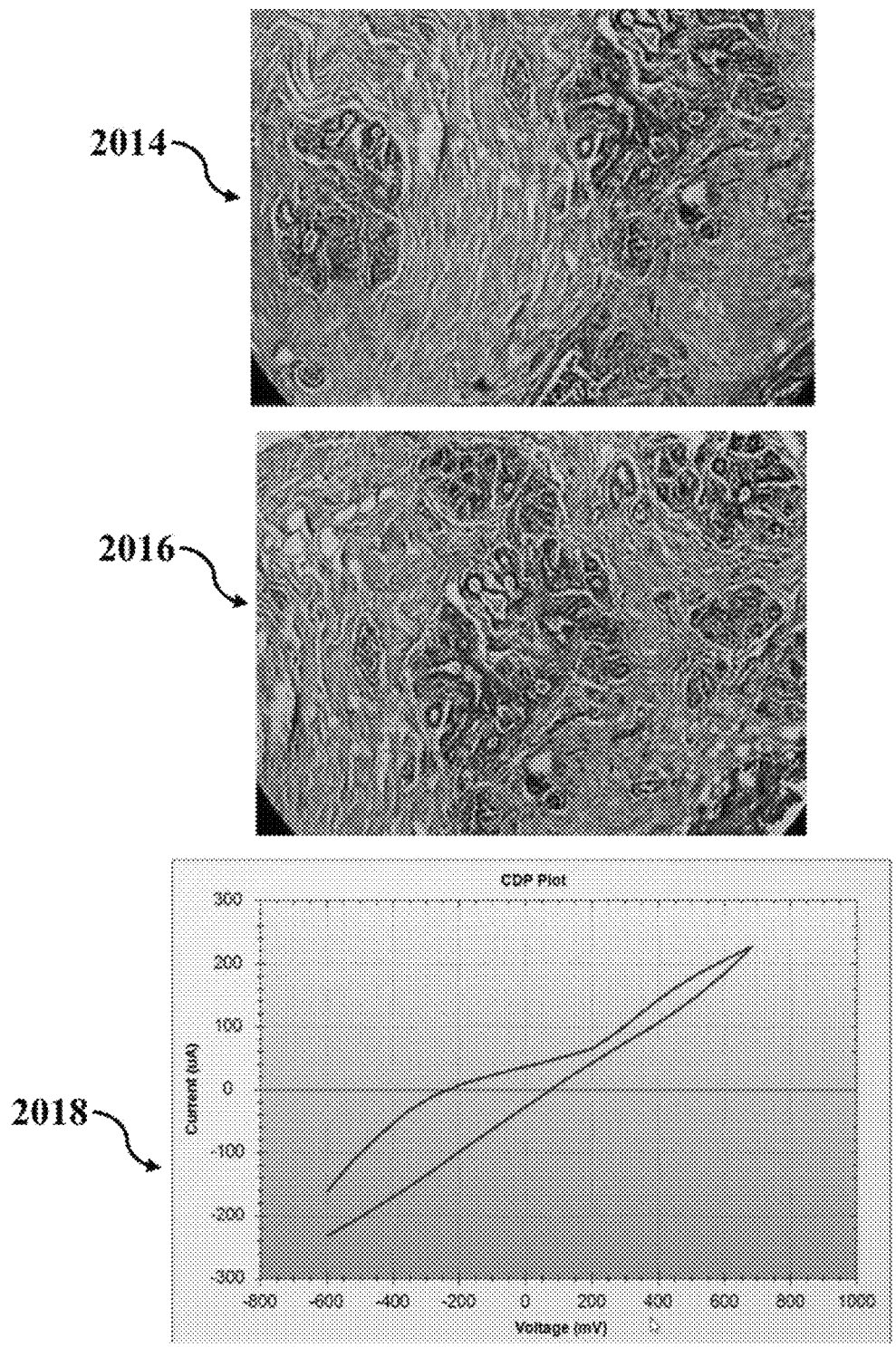
FIG. 20C illustrates an image resulted from frozen H&E (top-side image), an image resulted from permanent H&E (middle-side image), and a CV response recorded by exemplary CDP (bottom-side image) for a suspicious margin inside the body of the patient (posterior IM of patient ID 46), consistent with one or more exemplary embodiments of the present disclosure.

FIG. 20C shows an image resulted from frozen H&E (top-side image 2014), an image resulted from permanent H&E (middle-side image 2016), and a CV response recorded by exemplary CDP 102 (bottom-side image 2018) for a suspicious margin inside the body of the patient (posterior IM of the same patient ID 46), consistent with one or more exemplary embodiments of the present disclosure. It may be observed that real-time CV response recorded by exemplary CDP 102 negatively scored the margin, which was confirmed by both frozen and permanent H&E as usual hyperplasia.

Figure 20D:
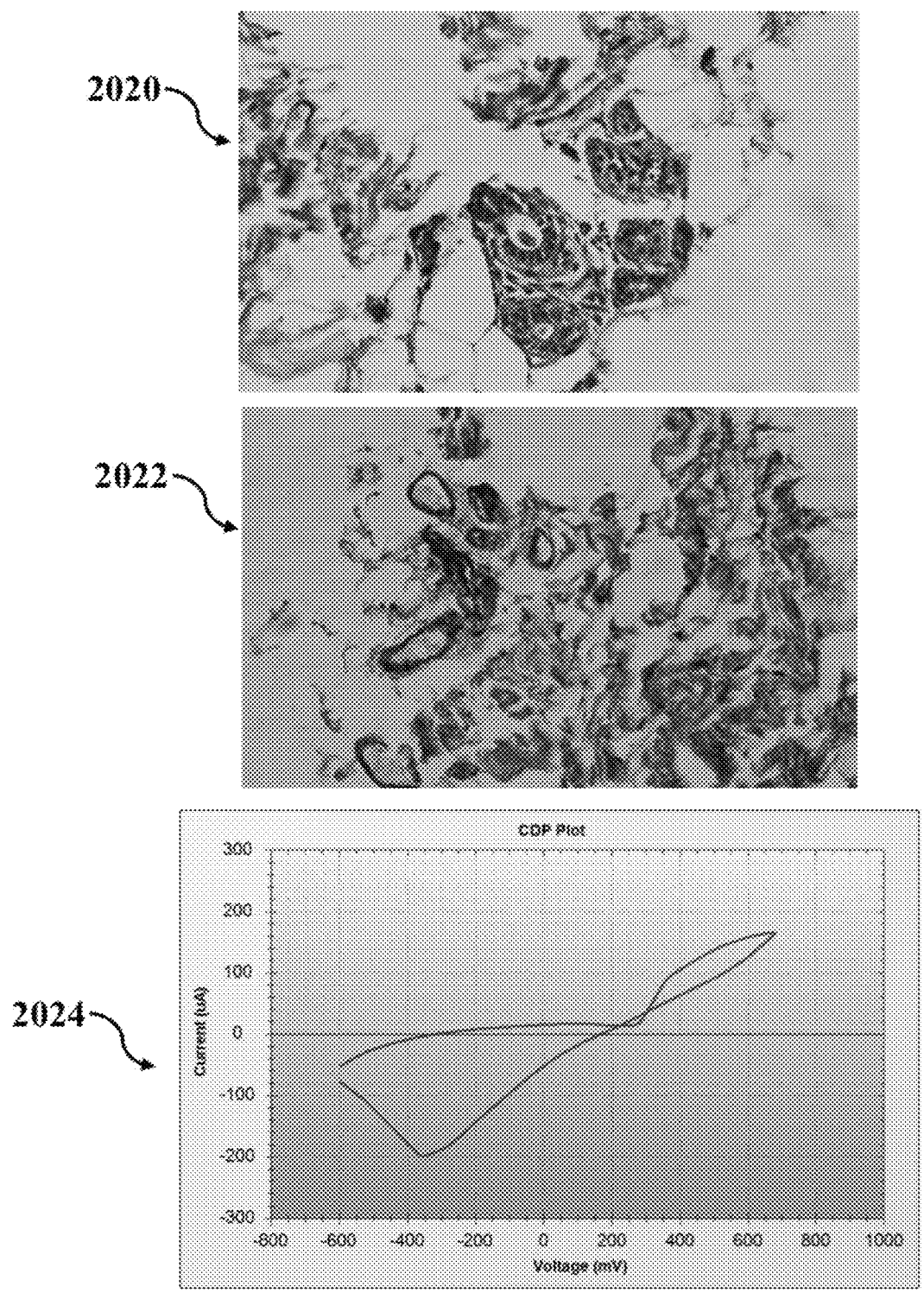
FIG. 20D illustrates an image resulted from frozen H&E (top-side image), an image resulted from permanent H&E (middle-side image), and a CV response recorded by exemplary CDP (bottom-side image) for Sentinel Lymph Node (SLN) of patient ID 18, consistent with one or more exemplary embodiments of the present disclosure.

FIG. 20D shows an image resulted from frozen H&E (top-side image 2020), an image resulted from permanent H&E (middle-side image 2022), and a CV response recorded by exemplary CDP 102 (bottom-side image 2024) for Sentinel Lymph Node (SLN) of patient ID 18, consistent with one or more exemplary embodiments of the present disclosure. It may be observed that real-time CV response recorded by exemplary CDP 102 negatively scored the margin, whereas it was diagnosed as reactive lymphoid hyperplasia by both H&E assays.

Regarding EXAMPLEs 10 and 11 described hereinabove, a matched clinical diagnostic categorization between the pathological results of the tested tissues and response peaks obtained by exemplary CDP 102 was proposed based on pathological classification (ductal intraepithelial neoplasia (DIN), lobular intraepithelial neoplasia (LIN) and fibro epithelial lesion (FEL)) with the latest reported modifications. CDP scoring ability in intra-operative margin detection was verified on more than 890 human in-vivo clinical breast samples with sensitivity of about 97% and selectivity of about 94%. The ability of exemplary CDP 102 and exemplary method 200 in non-invasive and real-time diagnosis of internal margins with pathological values (from high-risk benign to pre-invasive and invasive cancer lesions) may make exemplary CDP 102 a distinct intra-operative tool with simple and small handheld equipment to increase the prognostic factor of the cancer patients.

Example 12: Real-Time Tracking of Hypoxia Glycolysis in Conization Samples for Cervical Intraepithelial Neoplasia (CIN) Detection In this example, exemplary methods 200 and 220 utilizing exemplary CDP 102 were applied to precisely diagnose the cervical intraepithelial neoplasia (CIN) cells in cone biopsy samples in real-time in order to improve pathological evaluations to find any missed CIN (I to III) or other high-risk dysplasia in cone biopsy samples. Electrochemical assays according to method 220 utilizing CDP 102 were carried out on in-vitro human fresh cervical samples prepared from 30 patients' candidate for conization through the history of abnormal cells present in their pap smear results. CV studies were done using DC voltage, and no AC frequency was applied. The potential was swept in the range from about $-0.8$ to about $+0.8$ V using a scan rate of about 100 mV s$^{-1}$. Hematoxylin and Eosin (H&E) staining was used as staining procedure in histopathology assays. Hypoxia related $H_2O_2$ ionic currents from the in-vitro human fresh cervical samples prepared from 30 patients were recorded. Hypoxia glycolysis metabolism of fresh cervical tissues was monitored immediately after dissection from the body (with a non-dehydrated size of up to 6 cm$^2$). In each sample, at least three points on all over the tissue were recorded and inked the measured locations. Next, the tissues held in formalin and sent for standard pathological evaluation (dehydration, block preparation from the tissues, preparing a thin layer slide from the block, and H&E staining of the slides). The permanent pathological diagnostic results of samples were carried out independently from considering the inked locations. After the declaration of pathological results, the block of samples was re-molded and re-blocked from the surface in which the trace of inked points (points tested by exemplary CDP 102) could be observable. Again, the H&E slide preparation processes were carried out, and the pathological diagnosis of inked regions was declared. This second pathological evaluation was assumed as the reference for responses recorded by exemplary CDP 102.

Figure 21:
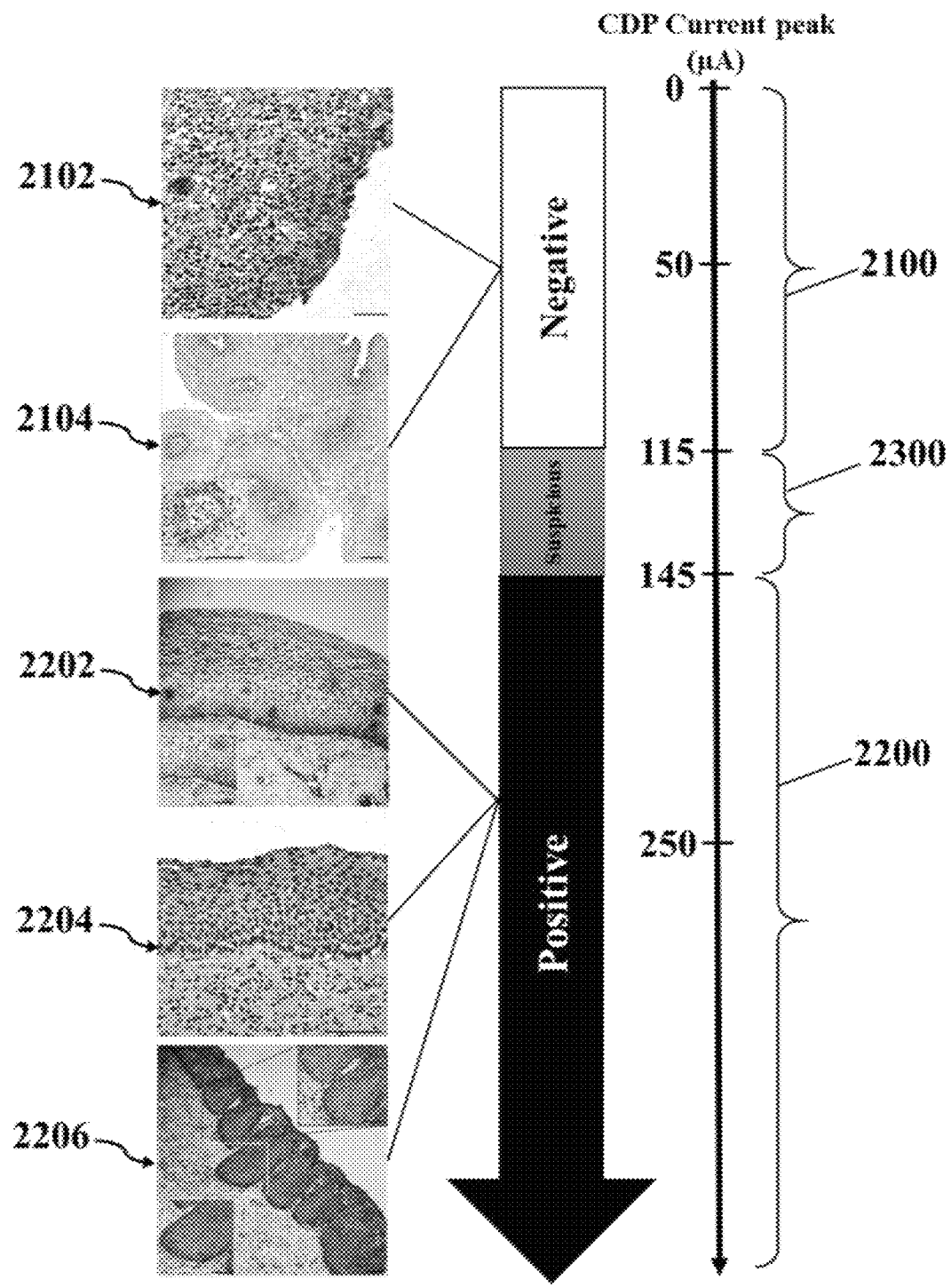
FIG. 21 illustrates a visually summarized comparison between current peak values of recorded CV responses utilizing the exemplary CDP via exemplary methods for in-vivo cancer diagnosis within a living tissue, and CIN pathological classification, consistent with one or more exemplary embodiments of the present disclosure.

FIG. 2I shows a visually summarized comparison between current peak values of recorded CV responses utilizing exemplary CDP 102 via exemplary methods 200, and 220 for in-vivo cancer diagnosis within a living tissue, and CIN pathological classification, consistent with one or more exemplary embodiments of the present disclosure. Coherent results were achieved after categorizing the values of recorded current peaks from the samples and comparing them with the H&E diagnosis of the inked samples. As may be observed from FIG. 21, current peak values of the recorded CV diagrams from the samples were categorized in three ranges of a first range 2190 assigned as being at healthy state, a second range 2200 assigned as being at cancerous state, and a third range 2300 assigned as being at a suspicious state. Among 30 samples, 9 samples were non-CIN tissues (healthy tissues) including chronic cervicitis and benign flat condyloma tissues, which all showed current peaks in the first range 2100 as being between about 0 µA and about 115 µA, and their healthy state was confirmed by H&E results as is exemplary shown in images 2102 (Chronic cervicitis) and 2104 (flat condyloma). Nineteen samples were low grade cancerous and high-grade cancerous, including CIN I (image 2202), CIN II (image 2204), and CIN III (image 2206) with neoplastic mitotic cells, in which all samples showed current peaks above about 145 µA within the second range 2200. By considering the pathology reports of tested regions utilizing exemplary CDP 102, a CIN based scoring of CV responses was proposed. The lowest cut-off for pathologists to declare a positive diagnosis of a cone biopsied sample may be the presence of low-grade CIN 1 or neoplastic mitotic cells in upper layers of basal cells. The current peak of about 115 µA was the lowest value recorded for an involved sample. Hence, it was proposed as a cut-off current for positive scoring of CV recorded responses. Samples with current peaks in the third range 2300 between about 115 µA and about 145 µA were assigned as suspicious samples to be cancerous being at a gray zone, for which re-evaluation by pathology is recommended.

As described and shown hereinabove, exemplary methods 200, and 220, and exemplary CDP 102 may be utilized to lively and selectively determine a value of $H_2O_2$ released from cancer or atypical cells, through reverse Warburg effect and hypoxia assisted glycolysis pathways. The determined value of released $H_2O_2$ may be a high-accurate parameter for cancer detection in any solid or liquid suspicious mass that may be cancerous. Although the pathology method may be a gold standard of cancer diagnosis, it needs to prepare a lot of H&E slides to reach a perfect diagnosis without any false negatives as well as time consuming pathology procedures. Accordingly, exemplary methods 200, and 220 and exemplary CDP 102 may be applied as a more accurate and faster diagnostic tool in comparison with pathology assays, or as a complementary diagnostic tool for pathology assays in order to reach fast and accurate cancer detection.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure, and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in light of the attached claims and their equivalents. Also, various modifications and changes may be made within the scope of the attached claims.

What is claimed is:

1. A potentiostat circuit for measuring an electrochemical response from a three-electrode array, the potentiostat circuit comprising:
a control amplifier comprising a first control input, a second control input coupled to a reference electrode of the three-electrode array, and a control output coupled to a counter electrode of the three-electrode array, the control amplifier configured to generate a control voltage at the control output by amplifying a voltage difference between the first control input and the second control input;

a transimpedance amplifier comprising a transimpedance output and a transimpedance input connected to a working electrode of the three-electrode array, the transimpedance amplifier configured to generate a transimpedance voltage at the transimpedance output by amplifying a voltage of the transimpedance input;

a peak detector circuit comprising a detector output and a detector input, the detector input coupled to the transimpedance output, the peak detector circuit configured to:
  detect a maximum voltage at the detector input in a given period of time; and
  transmit the maximum voltage to the detector output;

a feedback network connected between the detector input and the transimpedance input;

a periodic wave generator configured to:
  generate a periodic wave at the first control input responsive to becoming active; and
  couple the first control input to ground responsive to becoming inactive; and a comparator circuit configured to:
  activate the periodic wave generator by providing an activation voltage to an activation input of the periodic wave generator responsive to a voltage of the detector output being smaller than a reference voltage; and
  deactivate the periodic wave generator by providing a deactivation voltage to the activation input responsive to a voltage of the detector output being equal to or greater than the reference voltage.

2. The potentiostat circuit of claim 1, wherein the comparator circuit comprises:
a first comparator input connected to the detector output;
a second comparator input comprising the reference voltage, the second comparator input coupled to a DC voltage supply comprising a DC voltage; and
a comparator output connected to the activation input, wherein the comparator circuit is configured to:
  provide the activation voltage to the comparator output responsive to a voltage of the first comparator input being smaller than a voltage of the second comparator input; and
  provide the deactivation voltage to the comparator output responsive to the voltage of the first comparator input being equal to or greater than the voltage of the second comparator input.

3. The potentiostat circuit of claim 2, wherein the second comparator input is coupled to the DC voltage supply via a variable resistor configured to provide the reference voltage to the second comparator input by transmitting a fraction of the DC voltage to the second comparator input.

4. The potentiostat circuit of claim 2, wherein the periodic wave generator comprises:
a pulse wave generator configured to generate a periodic rectangular wave;
an operational amplifier (op-amp) coupled to the pulse wave generator, the op-amp comprising:
  a positive input connected to ground;
  a negative input coupled to an output of the pulse wave generator; and
  an op-amp output connected to the first control input;
an RC circuit connected between the op-amp output and the negative input, the RC circuit comprising a first resistor $R_1$ and a first capacitor $C_1$ connected in parallel;
a second resistor $R_2$ connected to the negative input;
a third resistor $R_3$ connected between the second resistor $R_2$ and the output of the pulse wave generator; and
a field effect transistor (FET) comprising:
  a source connected to ground;
  a drain connected between the second resistor $R_2$ and the third resistor $R_3$; and
  a gate connected to the activation input.

5. The potentiostat circuit of claim 4, wherein the first resistor $R_1$, the first capacitor $C_1$, the second resistor $R_2$, and the third resistor $R_3$ satisfy a set of conditions defined by the following:

$$R_1 C_1 > 100/f_{pw}$$

$$R_2 = R_3 < 0.1 R_1$$

where $f_{pw}$ is a frequency of the periodic rectangular wave.

6. The potentiostat circuit of claim 1, wherein the potentiostat circuit further comprises a unity gain amplifier connected between the reference electrode and the second control input, the unity gain amplifier comprising:
a first unity gain input connected to the reference electrode;
a unity gain output connected to the second control input; and
a second unity gain input connected to the unity gain output;
wherein the unity gain amplifier is configured to transmit a voltage at the reference electrode to the unity gain output by amplifying a voltage difference between the first unity gain input and the second unity gain input.

7. The potentiostat circuit of claim 6, wherein each of the control amplifier, the transimpedance amplifier, and the unity gain amplifier comprises a respective operational amplifier (op-amp).

8. The potentiostat circuit of claim 1, wherein the potentiostat circuit further comprises a first current buffer amplifier (CBA) connected between the control amplifier and the counter electrode, the first CBA configured to transfer an electric current flowing through the control output to the counter electrode.

9. The potentiostat circuit of claim 8, wherein the potentiostat circuit further comprises a second current buffer amplifier (CBA) connected between the transimpedance amplifier and the peak detector circuit, the second CBA configured to transfer an electric current flowing through the transimpedance output to the detector input.

10. The potentiostat circuit of claim 1, wherein the potentiostat circuit further comprises a first analog compensator connected between the counter electrode and the first control input, the first analog compensator configured to compensate voltage variations at the counter electrode responsive to voltage variations at the first control input.

11. The potentiostat circuit of claim 10, wherein the potentiostat circuit further comprises a second analog compensator connected between the second control input and ground, the second analog compensator configured to compensate voltage variations at the second control input.

12. The potentiostat circuit of claim 11, wherein:
the first analog compensator comprises a first compensation capacitor; and
the second analog compensator comprises a second compensation capacitor and a compensation resistor connected in series.

13. The potentiostat circuit of claim 1, wherein the feedback network comprises a feedback resistor, a resistance $R_f$ of the feedback resistor equal to $$\frac{V_{ref}}{I_{max}},$$

where $V_{ref}$ is the reference voltage and $I_{max}$ is an upper limit of an electric current flowing through the detector input.

* * * * *